(12) United States Patent
Gill et al.

(10) Patent No.: US 8,592,399 B2
(45) Date of Patent: Nov. 26, 2013

(54) S1P RECEPTORS MODULATORS AND THEIR USE THEREOF

(75) Inventors: Gurmit S. Gill, Craigieburn (AU); Damian W. Grobelny, Watsonia North (AU)

(73) Assignee: Akaal Pharma Pty Ltd., Bundoora (AU)

( * ) Notice: Subject to any disclaimer, the term of this patent is extended or adjusted under 35 U.S.C. 154(b) by 0 days.

(21) Appl. No.: 13/124,549

(22) PCT Filed: Oct. 19, 2009

(86) PCT No.: PCT/AU2009/001371
§ 371 (c)(1),
(2), (4) Date: Sep. 16, 2011

(87) PCT Pub. No.: WO2010/043000
PCT Pub. Date: Apr. 22, 2010

(65) Prior Publication Data
US 2011/0318388 A1 Dec. 29, 2011

(30) Foreign Application Priority Data

Oct. 17, 2008 (AU) ............................... 2008905369
Aug. 5, 2009 (AU) ............................... 2009903644

(51) Int. Cl.
A61K 31/675 (2006.01)
A61K 31/66 (2006.01)
A61K 31/00 (2006.01)
A61K 31/41 (2006.01)

(52) U.S. Cl.
USPC ......... 514/128; 514/210.18; 514/364; 514/91

(58) Field of Classification Search
None
See application file for complete search history.

(56) References Cited

U.S. PATENT DOCUMENTS

| 2,550,646 | A | 4/1951 | Murray |
| 5,643,932 | A | 7/1997 | Chihiro et al. |
| 5,798,354 | A | 8/1998 | Bernardon et al. |
| 5,877,342 | A | 3/1999 | Bernardon et al. |
| 5,883,106 | A | 3/1999 | Stevens et al. |
| 6,221,865 | B1 | 4/2001 | Sebti et al. |
| 6,228,868 | B1 | 5/2001 | Gwaltney, II et al. |
| 6,258,811 | B1 | 7/2001 | Yamauchi et al. |
| 6,376,491 | B1 | 4/2002 | Aoki et al. |
| 2002/0103234 | A1 | 8/2002 | Kikuchi et al. |
| 2007/0149561 | A1 | 6/2007 | Dhanak et al. |
| 2008/0176874 | A1 | 7/2008 | Bourrie et al. |
| 2008/0200535 | A1 | 8/2008 | Ohmori et al. |
| 2009/0118349 | A1 | 5/2009 | Szekely et al. |
| 2012/0034270 | A1 | 2/2012 | Grobelny et al. |

FOREIGN PATENT DOCUMENTS

| EP | 1661881 A2 | 5/2006 |
| EP | 1864980 A1 | 12/2007 |
| JP | 2007169194 A | 7/2007 |
| WO | WO-9509159 A1 | 4/1995 |
| WO | WO-0144223 A1 | 6/2001 |
| WO | WO-02074758 A2 | 9/2002 |
| WO | WO-03050098 A1 | 6/2003 |
| WO | WO-2004011418 A1 | 2/2004 |
| WO | WO-2004047724 A2 | 6/2004 |
| WO | WO-2004058762 A1 | 7/2004 |
| WO | WO-2005032471 A2 | 4/2005 |
| WO | WO-2005082089 A2 | 9/2005 |
| WO | WO-2005123673 A1 | 12/2005 |
| WO | WO-2006055625 A2 | 5/2006 |
| WO | WO-2007024922 A1 | 3/2007 |
| WO | WO-2007076055 A2 | 7/2007 |
| WO | WO-2007092638 A1 | 8/2007 |
| WO | WO-2007127183 A1 | 11/2007 |
| WO | WO-2008021532 A2 | 2/2008 |
| WO | WO-2008064320 A2 | 5/2008 |
| WO | WO-2008070740 A1 | 6/2008 |
| WO | WO-2008073785 A2 | 6/2008 |
| WO | WO-2008073942 A2 | 6/2008 |
| WO | WO-2008079382 A1 | 7/2008 |
| WO | WO-2008098857 A1 | 8/2008 |
| WO | WO-2008099781 A1 | 8/2008 |
| WO | WO-2008152149 A1 | 12/2008 |
| WO | WO-2009153307 A1 | 12/2009 |
| WO | WO-2010065760 A1 | 6/2010 |
| WO | WO-2010069949 A1 | 6/2010 |

OTHER PUBLICATIONS

Anderson (Chem and Biol 10:787-797, 2003).*
Thiel (Nature Biotechnol 2:513-519, 2004).*
Trofimov et al. "Synthesis of Isotryptamines and Tetrahydro-γ-Carbolines From 2-Indolylacetic Acid Derivatives." Chemistry of Heterocyclic Compounds. (1979):538-541.
Cowart et al., "Achievement of Behavioral Efficacy and Improved Potency in New Heterocyclic Analogs of Bezofuran H3 Antagonists", *Inflamm. Res..*, 54(Supplement 1): S25-S26 (2005).
Dawson et al., "An Adamantyl-Substituted Retinoid-Derived Molecule That Inhibits Cancer Cell Growth and Angiogenesis by Inducing Apoptosis and Binds to Small Heterodimer Partner Nuclear Receptor: Effects of Modifying Its Carboxylate Group on Apoptosis, Proliferation, and Protein-Tyrosine Phosphatase Activity", *J. Med. Chem.*, 50: 2622-2639 (2007).

(Continued)

Primary Examiner — Craig Ricci
(74) Attorney, Agent, or Firm — Mintz Levin Cohn Ferris Glovsky and Popeo, P.C.; Heidi A. Erlacher; Lian Ouyang

(57) ABSTRACT

The invention relates to novel compounds that have S1P receptor modulating activity. Further, the invention relates to a pharmaceutical comprising at least one compound of the invention for the treatment of diseases and/or conditions caused by or associated with inappropriate S1P receptor modulating activity or expression, for example, autoimmune response. A further aspect of the invention relates to the use of a pharmaceutical comprising at least one compound of the invention for the manufacture of a medicament for the treatment of diseases and/or conditions caused by or associated with inappropriate S1P receptor modulating activity or expression such as autoimmune response.

4 Claims, 1 Drawing Sheet

(56) References Cited

OTHER PUBLICATIONS

Li et al., "Synthesis and Biological Evaluation of 2-Indolyloxazolines as a New Class of Tubulin Polymerization Inhibitors. Discovery of A-289099 as an Orally Active Antitumor Agent", *Bioorganic & Medical Chemistry Letters*, 12: 465-469 (2002).

Clemens et al. "Synthesis of 4(5)-phenylimidazole-Based Analogues of Sphingosine-1-Phosphate and FTY720: Discovery of Potent S1P1 Receptor Agonists." *Bioorg. Med. Chem. Lett*. 15.15(2005):3568-3572.

de Mauny. Some Aminonitro Alcohols and Polyamino Alchohols. *Bulletin de la Societe Chimique de France*. 11(1944):281-283. (French Original and English Abstract).

Fancelli et al. "Solid Phase Synthesis of 2-Substituted Benzofurans via the Palladium-catalysed Heteroannulation of Acetylenes." *Tetrahed. Lett*. 38.13(1997):2311-2314.

Villanueva et al. "A Trapped Intermediate in the Copper(II)-Mediated Template Synthesis of an Amino Acid-Containing Ligand." *Inorg. Chem*. 36(1997):4585-4592.

\* cited by examiner

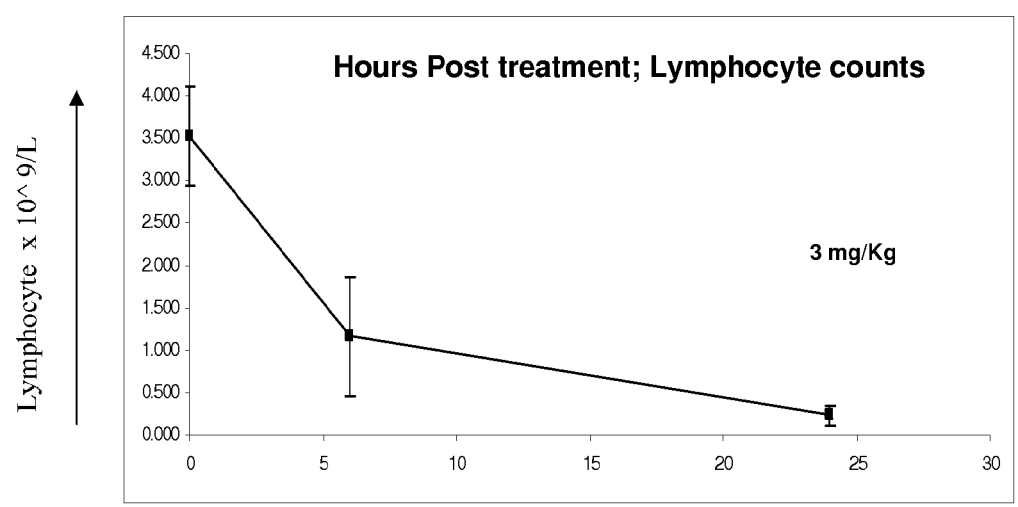

S1P RECEPTORS MODULATORS AND THEIR USE THEREOF

RELATED APPLICATIONS

This application is a national stage application, filed under 35 U.S.C. §371, of International Application No. PCT/AU2009/001371, filed on Oct. 19, 2009 which claims the benefit of and priority to Australian Application No. 2008905369 filed Oct. 17, 2008 and Australian Application No. 2009903644 filed on Aug. 5, 2009, the disclosure of each is incorporated herein by reference in its entirety.

FIELD OF INVENTION

This invention relates to novel compounds having S1P receptors modulating activity and the use of such compounds to treat diseases associated with inappropriate S1P receptor/s activity.

BACKGROUND

Sphingosine 1-phosphate (S1P) is a natural sphingolipid that functions as an intramolecular messenger in many types of cells and as an extracellular signalling molecule (for a recent review see Cooke et al, Annual Reports in Medicinal Chemistry, 2007, 42, pp 245-263 and references therein). The cellular effects induced by S1P are associated with platelet aggregation, cell morphology and proliferation, tumour cell invasion, endothelial cell chemotaxis and in vitro angiogenesis. The extracellular signalling occurs through interaction of S1P with G-protein-coupled receptors S1P1, S1P2, S1P3, S1P4 and S1P5. The intracellular activity of S1P and modulators has not been fully explored. S1P and its target have an essential role in lymphocyte migration through secondary lymphoid organs such the spleen, lymph nodes and mucosa-associated tissues such as the tonsils and Peyer's patches. The lymphocytes move from the peripheral circulation into the lymph nodes and mucosa associated tissues in order to generate immune responses. T and B lymphocytes are effectively sequestered within the thymus and secondary lymphoid tissue. Essentially, S1P and its receptor subtype −1 are required for lymphocytes to move out of the thymus and secondary lymphoid organs.

S1P type molecular modulators have been shown to be effective in multiple animal disease models. The S1P signalling, mainly through its receptor subtype-1, is important in halting the $T_{reg}$ response and has been recommended for immunotherapy of cancer and infectious disease (Liu, G., et al, Nature Immunology, 2009, 10, 769-777; Wolf, A. M., et al, J. Immunology, 2009, 183, 3751-60). The S1P mediated trans-activation of insulin receptor has been reported to help treating insulin resistance and type 2 diabetes (Rapizzi E. et al, Cell Mol Life Sci, 2009, 66, 3207-18). S1P1 receptor axis has a role in the migration of neural stem cells toward the site of spinal cord injury (Kimura, A., et al, Stem Cells, 2007, 25, 115-24). The S1P and its modulators supports the trafficking of hematopoietic progenitor cells and are helpful in tissue repair in myocardial infarction (Seitz, G., et al, Ann. N.Y. Acad. Sci., 2005, 1044, 84-89; Kimura, et al, Blood, 2004, 103, 4478-86) and a have great potential applications in regenerative medicines. S1P receptors play critical role in endothelial barrier enhancement and vasculature maturation (McVerry, B. J., et al, Journal of Cellular Biochemistry, 2004, 1075-85; Allende, M. L., et al, Blood, 2003, 102, pp 3665-7; Paik, J., et al, Genes and Development, 2004, 18, 2392-2403; Garcia, J. G. N., et al, J. Clinical Investigation, 2001, 689-701). The vasculature normalization helps the cytotoxic T cells to access the remote and inner part of the tumour (Hamzah J. et al, Nature, 2008, 453, pp 410-414). The lymphocyte egress and endothelial barrier function is mediated through S1P1 receptor (Brinkmann, et al, American J. of transplantation, 2004, 4, 1019-25; McVerry B. J. et al, Cellular Signalling, 2005, 17, pp 131-39). S1P type modulation reduces ischemia reperfusion injuries (Lein, Y. H., et al, Kidney International, 2006, 69, 1601-8; Tsukada, Y. T. et al, J Cardiovascular Pharmocol, 2007, 50, 660-9). S1P1 signalling is critical in preventing inflammation induced vascular leakage (Niessen, F. et al; Blood, 2009, 113, 2859-66; Wang L et al, Microvascular Research, 2009, 77, 39-45; Lee, J. F., et al, Am. J. Physiol Heart Circ Physiol, 2009, 296, H33-H42). It also reduces a vascular leakage in models of acute lung injury (McVerry, B. J., et al, Am J of Respiratory and Critical Care Medicine, 2004, 170, 987-93). The S1P vasculo-protection effect, mediated by nitric oxide and prostacyclin (Rodriguez C et al, Thromb Haemost, 2009, 101, 66-73), prevents the development of atherosclerotic lesions (Nofer, J. R. et al, Circulation, 2007, 115, 501-8; Tolle, M., et al, European J Clin Inv, 2007, 37, 17-9; Keul, P., et al, Arterioscler. Thromb. Vasc. Biol, 2007, 27, 607-13). S1P prevents tumour necrosis factor alpha mediated monocyte adhesion to endothelial cells, implicated in the pathology of arthrosclerosis and inflammatory diseases (Bolick, D. T. et al, Arterioscler. Thromb. Vasc. Biol., 2005, 25, 976-81). Recently reported target of S1P includes the family of Histone Deacylases (HDACs) (Hait, N. C., et al, Science, 2009, 325, 125-7), which are known for their role in epigenetic. The S1P has been reported to help treatment of the latent *mycobacterium tuberculosis* infection by promoting the processing and presentation of antigens (Santucci, M. B. et al, Biochem Biophys Res Comm, 2007, 361, 687-93). Additionally, the S1P and its modulators have cardio protective effects (Means, C. K., et al, Cardiovascular Research; 2009, 82, 193-200; Hofmann, U., et al, Cardiovascular Research, 2009, 83, 285-93; Tao, R., et al, J Cardiovasc Pharmacol, 2009, 53, 486-94) and the signalling axis of S1P are important in the treatment of myocardial infarction (Yeh, C. C., et al, Am J Physiol Heart Circ Physiol; 2009, 296, H1193-9). Thus S1P like molecular modulators have a great developmental potential in wide range of cardiovascular medicines. Role of S1P receptor subtype-1 in modulating nociception have recently been described (Selley S M J et al, Journal of Neurochemistry, 2009, 110, pp 1191-1202).

Fingolimod (2-amino-2-(2-[4-octylphenyl]ethyl)-1,3-propanediol) (FTY-720) is metabolised to a structural analogue of S1P and has been found to effect S1P receptors. The discovery of FTY-720 and its efficiency in animal models and clinical studies, related to many autoimmune diseases and cancer treatment, has resulted in research efforts into S1P receptors.

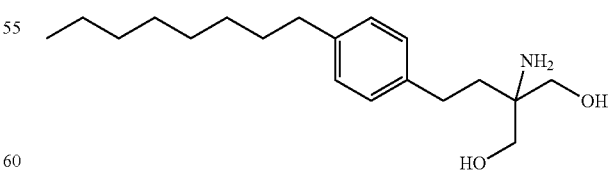

FTY-20

FTY-720 decreases peripheral blood lymphocyte counts (lymphopenia) reversibly, without impairing the effector function of the immune cells (Pinschewer, D. et al, J. Immunology, 2000, 164, 5761-70). FTY-720 is an emerging novel drug for Multiple Sclerosis (MS) (Kieseier, B. C., et al, Pharmacological Research, 2009, 60, 207-11; Brown, B. A., The Annals of Pharmacotherapy, 2007, 41, 1660-8) and has a direct cyto-protective and process extension effect in oligodendrocyte progenitors (Coelho, R. P. et al, J. Pharmacology and Experimental Therapeutics, 2007, 323, 626-35; Miron, V. E. et al, Ann Neurol, 2008, 63, 61-71). It is effective against autoimmune related pathologies such as type-1 diabetes (Yang, Z., et al, Clin Immunology, 2003, 107, 30-5), arthritis (Matsuura, et al, Inflamm Res, 2000, 49, 404-10) and oxazolone stimulated colitis (Daniel, et al, Molecular Immunology, 2007, 44, 3305-16). FTY-720 interaction with cytosolic Phospholipase A2 and modulation the eicosanoids synthesis (Payne S. G. et al; Blood, 2007, 109, pp 1077-1085) indicates its potential as anti-inflammatory and antinociceptive agents and a safe pain killer (Coste, O., et al, J. Cell Mol. Med., 2008, Vol 12, 995-1004). The anticancer activity of FTY-720 is well documented by in vitro apoptotic activity studies as well as numerous animal model studies. The apoptotic mechanism observed in hepatocellular carcinoma cell lines is linked to the activation of protein kinase C delta (PKC-δ) (Hung, J. H., et al, 2008, 68, 1204-12). The apoptotic activity of FTY-720 against chronic myelogenous leukaemia and Philadelphia chromosome positive acute lymphocytic leukaemia was reported to be due to its control of Protein Phosphates 2A (PP2A) (Neviani et al, J of Clinical Investigation, 2007, 117, 24-21). Phosphorylated form of FTY-720 is speculated to be an anti-metastasis drug (Meeteren, et al, Cancer Lett., 2008, 266, 203-8). FTY-720 inhibits vascular endothelial cell growth factor induced vascular permeability (Sanchez, T., et al, J. Biological Chem., 2003, 278, 47281-90), linked to an anticancer and anti-metastatic effect in animal models (Azuma, H., et al, Cancer Res, 2002, 1410-19; Chua, C-W., at al, Int. J. Cancer, 2005, 117, 1039-48; LaMontange, K. et al, 2006, 66, 221-31). The anti-angiogenic effect of FTY-720 through its interaction with S1P receptor subtype –1, was described recently (Schmid, G., et al, J Cellular Biochem, 2007, 101, 259-70). FTY-720 helps favourable central nervous system (CNS) gene expression and improves the blood brain barrier function (Foster, C. A., et al, Brain Pathology, 2009, 19, 254-66). Few days of treatment with FTY-720 leads to complete eradication of chronic viral infection of lymphocytic choriomeningitis (Lanier, et al, Nature, 2008, 894-899). Its anti-fibrotic activity was reported recently (Brunati, A. M., et al, Biochem Biophys Acta, 2008, 1783, 347-59; Delbridge, M. S., et al, Transplantation Proceedings, 2007, 39, 2992-6). FTY 720 inhibits development of atherosclerosis in low density lipoprotein receptor deficient mice (Nofer, J. R., et al, Circulation, 2007, 115, 501-8; Tolle, M. et al, European J Clinical Investigation, 2007, 37, 171-79). FTY720 was effective in the treatment of cerebral ischemia in the mouse model (Czech, B., et al, Biochem Biophys Res Comm, 2009, online), indicating the great potential of S1P receptors modulators in the wide range of cardiovascular medicine. The derivatives of FTY-720 were reported as pulmonary barrier enhancers and thus potential agents for the development of critical care medicines (Camp, S. M., et al, J Pharmacol Experimental Therapeutics, 2009, online).

Of the classical mimics of S1P, the amino alcohols and their respective monophosphates, amino phosphonates, amino acids, alkoxyamino alcohols, alkyl carboxylates appear to be the most effective S1P receptors modulators. While an in vivo phosphorylation of the hydroxyl group of FTY 720 appears to be necessary for the most effective extracellular signalling and agonistic effect upon binding to S1P1-5, the apoptotic effect is limited to its non-phosphorylated form.

It is desirable to provide alternatives to FTY-720 and in particular alternative compounds with improved properties and/or activity. For example, this could include compounds with greater range of activity, altered or enhanced specificity, improved pharmacological properties or reduction in side effects.

Throughout this specification, use of the terms "comprises" or "comprising" or grammatical variations thereon shall be taken to specify the presence of stated features, integers, steps or components but does not preclude the presence or addition of one or more other features, integers, steps, components or groups thereof not specifically mentioned.

SUMMARY OF INVENTION

In one aspect of the present invention there is provided a compound of formula (I)

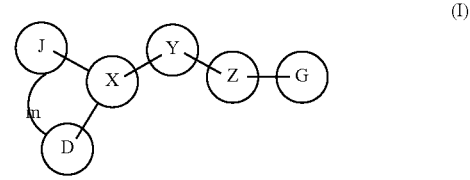

(I)

wherein G represents an organic substituent comprising in any combination one or more nitrogen, oxygen or sulphur atom(s). In one embodiment of this aspect of the invention, G is a group selected from the following:

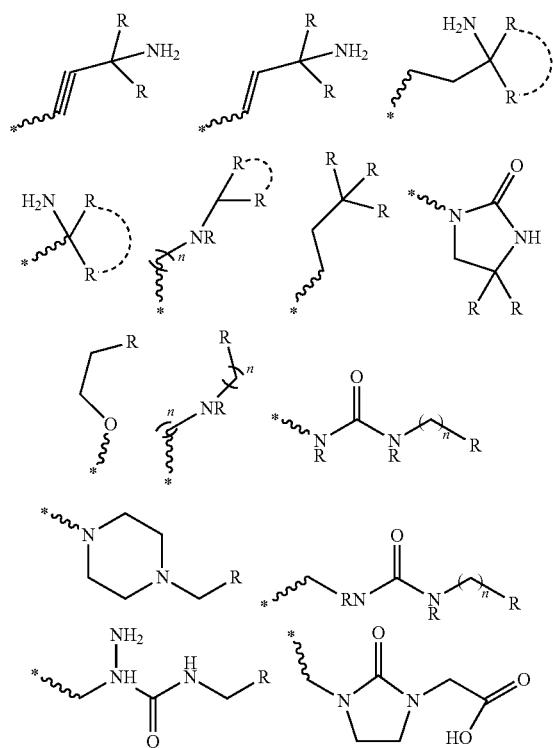

-continued

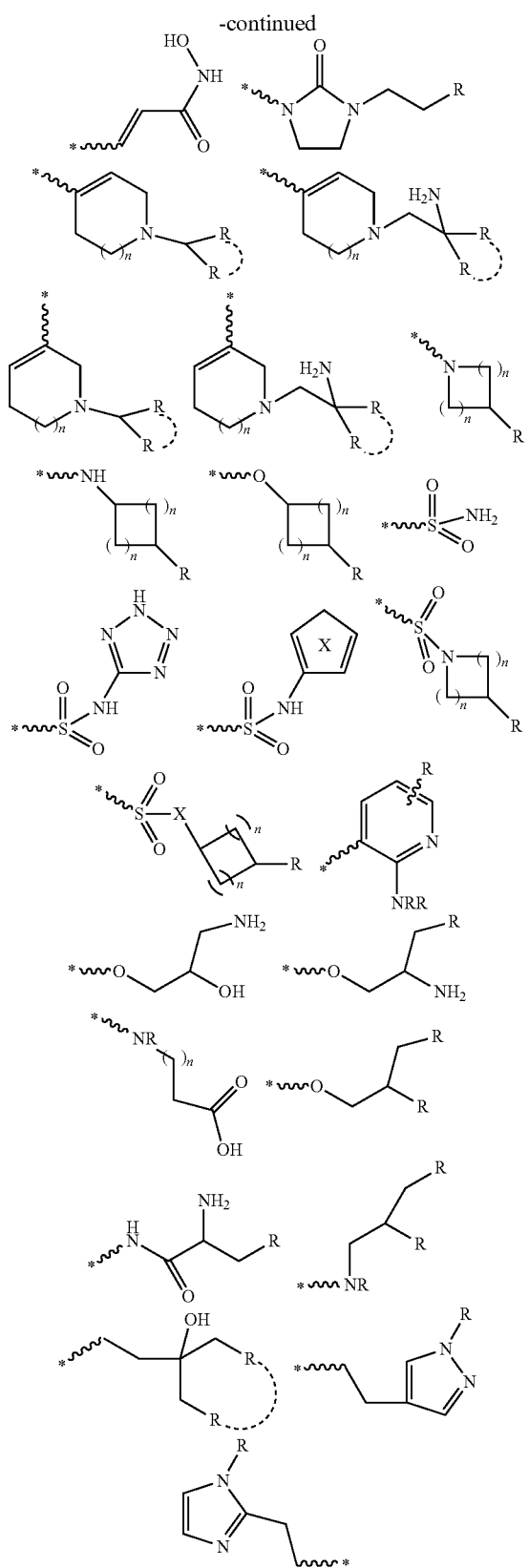

wherein R is independently selected from H, deuterium, CN, amino, alkylamino, CH$_2$OH, alkoxy, CF$_3$, an alkyl chain optionally containing one or more of deuterium, O, NR'R'' (wherein R' and R'' are independently selected from alkyl, substituted alkyl, cycloalkyl, substituted cycloalkyl, aryl, substituted aryl, heterocycle and substituted heterocycle) S, SO, SO2, halogen, a carbon-carbon double bond, a carbon-carbon triple bond, a carbon-heteroatom double bond or a carbon-hetero atom triple bond, carbocycle, heterocycle, amide, sulphonamide, hydroxyl, —CH$_2$COOH, —COOH, —OPO$_3$H$_2$, —PO$_3$H$_2$, cyclic phosphate, cyclic phosphonates and/or salts, tetrazole, and n is 0-4, with the proviso that if an amino group is present on the same carbon atom as R in group G, R is not hydroxyl,

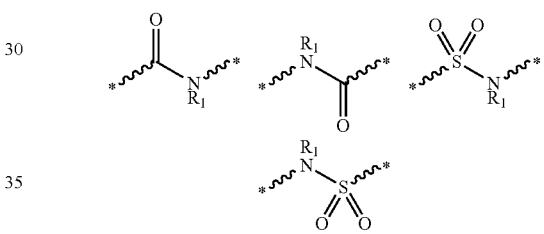

represents an optional bridging group;
the asterisks indicating the attachment within formula (I).

In the compound of formula (I), Z represents an organic moiety comprising at least one aromatic centre. X and Y separately, or in combination, are alkyl, alkyl-amino, alkoxy, an alkyl chain containing one or more of O, N, S, SO, SO$_2$, halogen, a carbon-carbon double bond, a carbon-carbon triple bond, a carbon-heteroatom double bond, carbocycle, heterocycle or a group selected from the following:

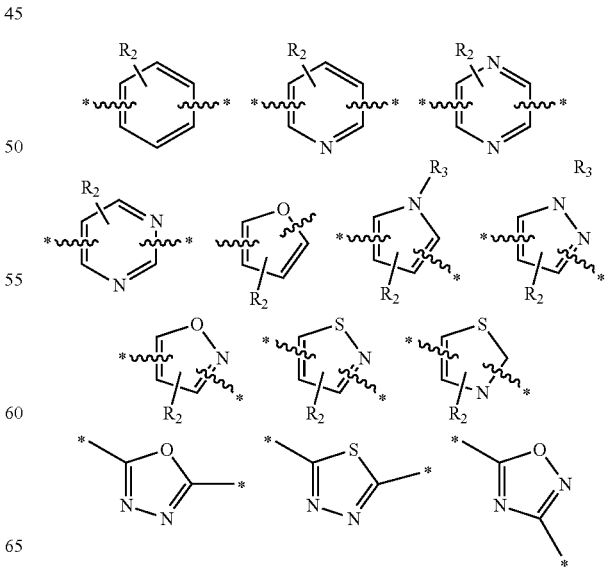

wherein R$_1$ is selected from H or alkyl, the asterisks indicating the attachment within formula (I).

In an alternative or further preferred embodiment of this aspect of the invention, X, Y and Z separately, or in any combination, are selected from the following

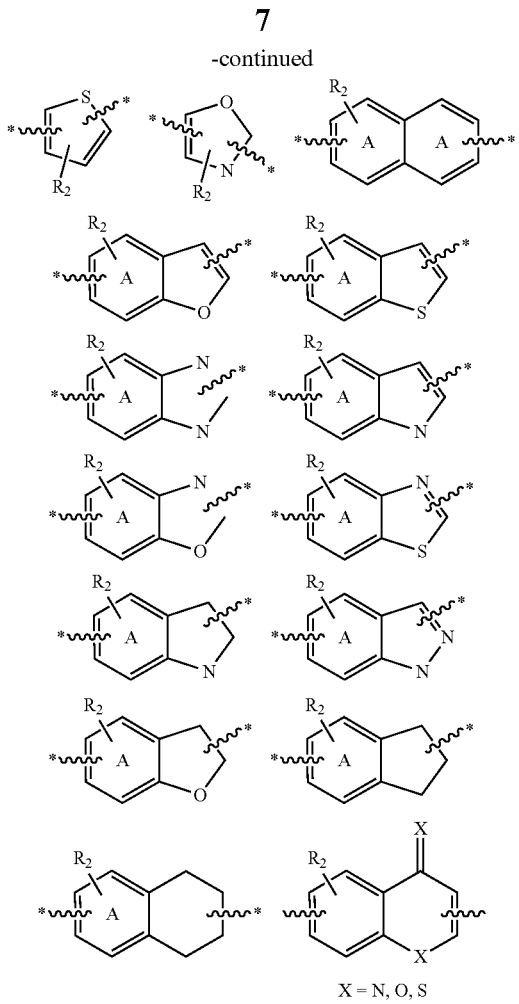

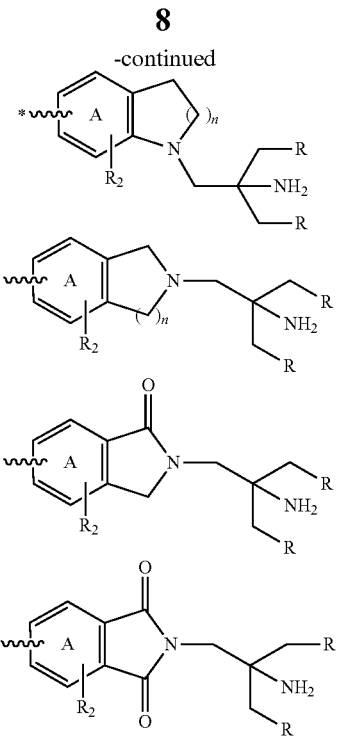

wherein R is as defined for group G, wherein A is defined as above and X is independently selected from the group consisting of heteroatom or heteroatom containing species such as O, N, S, SO, SO2, CO or C=NR and $R_2$ is as defined above, the asterisks indicating the attachment within formula (I).

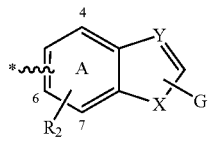

wherein A is defined as above, X and Y are independently selected from the group consisting of heteroatom or heteroatom containing species such as O, N, S, SO, SO2, CO or C=NR and $R_2$ is as defined above, the asterisks indicating the attachment within formula (I).

In the compound of Formula (I), the groups J, m and D separately, or in any combination, are selected from hydrogen, deuterium, alkyl, alkoxy, alkylamino, halogen, amino, hydroxy, oxo (=O), imino (=NR), cyano, aryl, variously substituted aryl, variously substituted heterocycle, variously substituted carbocycle, alkyl chain of 1-15 carbon atom optionally containing carbon-carbon multiple bond, carbon-hetero multiple bond wherein one or more carbon atoms can be independently replaced with oxygen, sulphur, SO, $SO_2$, NR (wherein R is a substituent), aryl, carbocycle and heterocycle.

In one embodiment the group D, when present, is selected from H, deuterium, alkyl, aryl, heterocycle or cycloalkyl. In a further embodiment the group m, when present, is selected from unsubstituted or substituted aryl, carbocycle or heterocycle. In a yet further embodiment, the group J, when present, is selected from H, alkyl or one of the following groups:

X = N, O, S wherein the asterisks indicate the attachment within formula (I), $R_2$ is selected from halogen, H, deuterium, CN, amino, alkylamino, alkoxy, $CF_3$, an alkyl chain (up to 20 carbon atom) optionally containing one or more of deuterium, OH, NR'R'' (wherein R' and R'' are independently selected from alkyl, substituted alkyl, cycloalkyl, substituted cycloalkyl, aryl, substituted aryl, heterocycle and substituted heterocycle) O, N, S, SO, $SO_2$, halogen, a carbon-carbon double bond, a carbon-carbon triple bond, a carbon-heteroatom double bond or a carbon-hetero atom triple bond, carbocycle, heterocycle, amide, sulphonamide and A represents one or more ring atoms or groups independently selected from the group consisting of C, N, O, S, CO, C=NR, SO or $SO_2$, $R_3$ may be a linking group or alkyl, aryl, heterocycle or an optionally substituted alkyl chain.

In a further alternative embodiment of this aspect of the invention Z and G, in combination, are selected from the following groups:

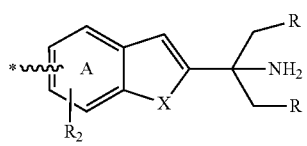

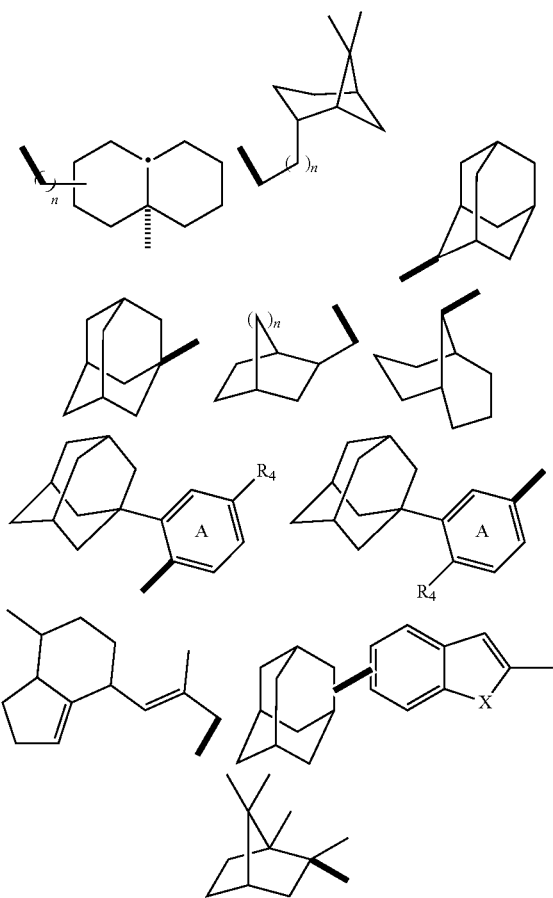

wherein n is 0-10, A is as defined above, $R_4$ is halogen, CN, amino, alkylamino, alkoxy, $CF_3$, an alkyl chain containing one or more of O, N, S, SO, $SO_2$, a carbon-carbon double bond, a carbon-carbon triple bond, a carbon-heteroatom double bond or a carbon-hetero atom triple bond.

In a further aspect of the invention there is provided compounds having S1P receptor modulating activity and/or expression against target cells.

A yet further aspect of the invention provides a pharmaceutical preparation comprising at least one compound described herein in any of its stereoisomeric and/or isotopic forms or physiologically tolerable and/or therapeutically effective salts or mixtures thereof in any ratio together with a pharmaceutically acceptable carrier(s) and/or excipient(s).

In a further aspect the invention provides the use of a compound of the invention in any one of its stereoisomeric and/or isotopic forms or physiologically tolerable and/or therapeutically effective salts or mixtures thereof in any ratio, for the production of a pharmaceutical for modulation of S1P receptor activity and/or expression against target cells.

In a further aspect the invention provides the use of a compound of the invention in any one of its stereoisomeric and/or isotopic forms and mixtures thereof in any ratio and/or physiologically tolerable and/or therapeutically effective salts for the production of a pharmaceutical for modulation of S1P receptor (extracellular and/or intracellular binders) activity and/or expression.

S1P receptors are cell surface receptors which include known receptor subtypes 1, 2, 3, 4, 5 and are regarded herein as S1P receptors. These extracellular S1P receptors may be present inside the cell on Golgi bodies, etc. There are other intracellular receptor/s, target/s, protein/s, enzyme/s where S1P interacts and are regarded as S1P receptor/s. The compounds of the invention could function as substrates of Sphingosine Kinases like SK1 and SK2 which are responsible for phosphorylation of S1P and are regarded as S1P receptor/s. Histone Deacylase/s (HDACs) are known intra-nuclear receptors of S1P and thus are regarded as S1P receptors. In broad terms, the invention includes any receptor binder, agonists or antagonists, or inverse agonists of the S1P receptor family including S1P1, S1P2, S1P3, S1P4 and S1P5, which is responsible for direct and or indirect effect of S1P and regards them as S1P receptor/s.

Further, the invention relates to the use of a pharmaceutical comprising at least one compound of the invention in any of its stereoisomeric and/or isotopic forms or physiologically tolerable and/or therapeutically effective salts or mixtures thereof in any ratio.

Further, the invention relates to the use of a pharmaceutical comprising at least one compound of the invention in any of its stereoisomeric and/or isotopic forms or physiologically tolerable and/or therapeutically effective salts or mixtures thereof in any ratio for the treatment of diseases and/or conditions caused by or associated with inappropriate S1P receptor modulating activity or expression, for example, autoimmune disease.

A further aspect of the invention relates to the use of a pharmaceutical comprising at least one compound of the invention in any of its stereoisomeric or isotopic forms or physiologically tolerable and/or therapeutically effective salts or mixtures thereof in any ratio for the manufacture of a medicament for the treatment of diseases and/or conditions caused by or associated with inappropriate S1P receptor modulating activity or expression such as autoimmune disease.

In yet a further aspect of the invention, the compounds of the invention can be used for the prevention and/or prophylaxis and/or treatment and/or immunotherapy of infectious diseases including any infection caused by viruses, bacteria, fungi, parasites, prions and/or any other pathogens.

Viral infections including but not limited to human immunodeficiency virus, Hepatitis (HAV, HBV, HCV), H1N1 influenza, chickenpox, cytomegalovirus infection, dengue fever, Ebola hemorrhagic fever, hand foot and mouth disease, herpes simplex, herpes zoster, HPV, influenza (Flu), Lassa fever, measles, Marburg Hemorrhagic fever, infectious mononucleosis, mumps, norovirus, poliomyelitis, progressive multifocal Leu-encephalopathy, rabies, rubella, SARS, smallpox (Variola), viral encephalitis, viral gastroenteritis, viral meningitis, viral pneumonia, west Nile disease and yellow fever.

Bacterial Infections including but not limited to actinomycosis, anaplasmosis, anthrax, bacterial meningitis, botulism, brucellosis, burkholderia infections, campylobacteriosis, cellulitis, chlamydiaceae infections, cholera, clostridium infections, coccidiomycosis, diphtheria, ehrlichiosis, empyema, gonorrhea, impetigomelioidosis legionellosis, leprosy (Hansen's Diseases), leptospirosis, listeriosis, lyme disease, bacterial endocarditis, endophthalmitis, pseudomembranous enterocolitis, erysipelas, *Escherichia coli* infections, necrotizing fasciitis, Fournier gangrene, furunculosis, fusobacterium infections, gram negative bacterial infections, gram positive bacterial infections, granuloma inguinale, hidradenitis suppurativa, histoplasmosis, hordeolum, impetigo, Klebsiella infections, ludwig's angina, lymphogranuloma venereum, maduromycosis, mycobacterium infections, MRSA infection, Mycoplasma infections, nocardia infections, onychomycosis, osteomyelitis, paronychia, pelvic inflammatory disease, plague pneumococcal infections, pseudomonas infections, psittacosis, puerperal infection, respiratory tract infections, retropharyngeal abscess, rheumatic fever, rhinoscleroma, rickettsia infections, rocky mountain disease, salmonella infections, scarlet fever, scrub typhus, sinusitis, shigellosis, spotted fever, bacterial skin disease, staphylococcal infections, streptococcal infections, syphilis, tetanus, trachoma, tick borne disease, epidemic typhus, tuberculosis, tularaemia, typhoid fever, urinary tract infections, whipple disease, whooping cough, vibrio infections, Yersinia infections, zoonoses, and zygomycosis, Fungal infections including but not limited to aspergillosis, blastomycosis, candidiasis, coccidioidomycosis, cryptococcosis, tinea pedis and histoplasmosis.

Prion infections including but not limited to transmissible spongiform encephalopathy, bovine spongiform encephalopathy, Creutzfeldt-Jakob disease, Kuru fatal Familial insomnia and Alpers Syndrome.

In a further aspect of the invention, the compounds of the invention can be used for the prevention and/or prophylaxis and/or treatment and/or immunotherapy of cancer and immune mediated diseases which include immune related and inflammatory diseases; autoimmune diseases; allergic conditions; pain; central nervous system diseases; neurodegenerative diseases, cardiovascular diseases; haematological pathologies. For example, Multiple Sclerosis, Alzheimer's, dementia, Parkinson's, Huntington's, Amyotrophic Lateral Sclerosis, Coeliac, inflammatory bowel, Crohn's, ulcerative colitis, Lupus Erythematosus, Lupus Nehritis, osteoarthritis, psoriasis, pruritus, arthritis, rheumatoid arthritis, osteoporosis, Sjogren Syndrome, uveitis, asthma, hay fever, sleep disorders, macular degeneration, glaucoma, type1 and 2 diabetes, myasthenia gravis, non-glomerular nephrosis, autoimmune hepatitis, Behcet's, glomerulonephritis, chronic thrombocytopenia purpure, haemolytic anaemia, Wegner's granuloma and fibrosis, nervous system (spasticity), spinal cord injury, spinocerebellar ataxia, tardive dyskinesia, cognitive disorders.

The compounds of the invention can be used for the prevention and/or prophylaxis and/or treatment and/or immunotherapy of or in, Down's syndrome, schizophrenia, bipolar disorder, drug dependence, Wernicke-Korsakoff syndrome, eating disorders, depression resulting from infection, hepatic encephalopathy, lung diseases such as grain handler's, Hermansky-Pudlak Syndrome, and adult respiratory distress syndrome (ARDS, obesity, digestive tract disease, anxiety, hyperalgesia, migraine, epilepsy and neuromuscular disorder.

In another embodiment the compounds of the invention can be used for prevention and/or treatment of vascular and/or cardiovascular diseases including, but not limited to, hypoxia, atherosclerosis, diabetic blood vessel disease like inflammation, hyper vascularisation related disorders such as cancer and neoplasm, heart failure, myocardial infarction, myocarditis, ischemia, hypotension, hypertension, reperfusion injury, angina pectoris, coronary artery disease, stroke, thrombosis, artery/vein blockage or obstruction, diabetic retinopathy, sepsis and kidney failure, reperfusion or injury.

In another embodiment the compounds of the invention can be used for prevention and/or prophylaxis and/or treatment and/or immunotherapy of liver diseases including but not limited to liver cirrhosis, viral liver infections, autoimmune hepatitis, liver failure, portal hypertension, hemochromatosis, Wilson's diseases, Gaucher disease, hepatoma, primary biliary cirrhosis, primary sclerosing cholangitis, sarcoidosis and Zwellweger syndrome.

In another embodiment the compounds of the invention can be used for the prevention and/or treatment and/or immunotherapy of solid and/or haematological cancers and tumor metastasis, including but not limited to acute B-cell leukaemia, lymphoma, chronic lymphocytic leukaemia, chronic myeloid leukaemia, hairy cell leukaemia, multiple myeloma, acute lymphocytic leukaemia, acute granulocytic leukaemia, acute myelogenous leukaemia, lung cancer, adrenal gland cancer, astrocytoma, glioma, brain cancer, bile duct cancer, bladder cancer, bone cancer, bowel cancer, colorectal cancer, breast cancer, cervical cancer, endometrial cancer, oesophageal cancer, melanoma, gallbladder cancer, Kaposi sarcoma, renal cancer, laryngeal cancer, liver cancer, mesothelioma, prostate cancer, sarcoma, skin cancer, stomach cancer, testicular cancer, uterine cancer, thyroid cancer, and pancreatic cancer.

In another embodiment the compounds of the invention can be used for prevention and/or treatment and/or immunotherapy of pain including chronic pain, which could either be somatogenic (organic) or psychogenic. The somatogenic pain may be of nociceptive, inflammatory and or neuropathic origin. The pain related to nociceptive pain, peripheral neuropathy, central neuropathy, neuralgia, migraine, psychotic, inflammatory and or neurological disorders.

In another embodiment the compounds of the invention can be used for organ transplant and/or allograft and/or autograft, for example, kidney, liver, lung, heart, skin, stem cell or bone marrow transplant and in the treatment of graft versus host disease.

In another embodiment the disclosed molecules can be used for prevention and/or treatment and/or immunotherapy for the pathologies caused by bioterrorism agents.

In another embodiment the compounds of the invention can be used as a vaccine adjuvant to boost and/or enhance the action of a vaccine and/or immune agent and/or for immunization; for example antigen, tumour cell lysate, B cell vaccine, T cell vaccine, dendritic cell vaccine boosting the immune response of cytotoxic cells, helper T cells and dendritic cells and for eradication and immunotherapy of immune related diseases and other preventable diseases such as chickenpox, cholera, diphtheria, whooping cough, meningococcal disease, hepatitis, Hemophilus influenzae type B (HIB), measles, mumps, rubella, poliomyelitis and tetanus.

In another embodiment the compounds of the invention can be used to mobilize the progenitor/stem cells preferably towards the site of injury, ischemia, stroke etc. The compounds can be used as cyto-protective agents, cardioprotective agent, neuro-protective agents and regenerative agents that may help host/patient to repair any organ damage, grow organs like muscle, nerve, blood vessel etc and to increase immune cells number.

As used herein, "treatment" includes any effect such as lessening, reducing, modulating and/or eliminating resulting in the improvement of the condition, disease or disorder to be treated.

An appropriate concentration level in treatment is from 0.01 nM to 1 Molar.

The compounds and compositions of the invention may be administered in combination with a variety of pharmaceutical excipients, including stabilizing agents carriers and/or encapsulation formulations known in the art.

In case of treatment of autoimmune and inflammatory diseases, the compounds of the present invention can be used alone or in combination with any suitable adjuvant, non limiting examples of which include, known immunosuppressants such as cyclosporine, tecrolimus, rapamycin, azathioprine, cyclophosphamide, dexamethasone, flunisolide, prednisolone, prednisone, amcinomide desonide, methylprednisolone, triamcinolone and alclometasone.

In case of treatment of infection and or cancer the compounds of the present invention can be administered alone or in any combination with any suitable adjuvant, non limiting examples of which include, other anticancer, antiviral, antibacterial, antifungal, and/or any anti-pathogen agent, a compound which could make a delayed type hypersensitivity response.

During vaccination/s and or immunization/s the molecule/s or compounds of the present invention may be used with T cell, B cell, dendritic cell, antigen, protein, protein conjugate and or like which could be used for such immunization purpose.

BRIEF DESCRIPTION OF THE FIGURES

FIG. 1 illustrates post-treatment lymophocyte counts

DETAILED DESCRIPTION OF THE INVENTION

The terms "compound", "agent", "active agent", "chemical agent", "pharmacologically active agent", "medicament", "active", "molecule" and "drug" are used interchangeably herein to refer to a chemical compound that induces a desired pharmacological and/or physiological effect. The terms also encompasses pharmaceutically acceptable and pharmacologically active ingredients of those active agents/compounds specifically mentioned herein and compounds of the invention including but not limited to salts, esters, amides, prodrugs, active metabolites, analogs and the like. When the terms "compound", "agent", "active agent", "chemical agent" "pharmacologically active agent", "medicament", "active" and "drug" are used, then it is to be understood that this includes the active agent per se as well as pharmaceutically acceptable and/or, pharmacologically active salt/s, esters, amides, prodrug/s, metabolites, analogs and the like.

The terms "effective amount" and "therapeutically effective amount" of an agent/s/compounds and compounds of the invention as used herein mean a sufficient amount of the compound to provide the desired therapeutic or physiological effect or outcome. A practitioner balances the potential benefits against the potential risks in determining what an appropriate "effective amount" is. The exact amount required will vary from subject to subject, depending on the species, age and general condition of the subject, mode of administration and the like.

A "pharmaceutically acceptable" carrier, excipient or diluent may include a pharmaceutical vehicle comprised of a material that may not be biologically active or otherwise undesirable, i.e. the material may be administered to a subject along with the selected active agent without causing any and/or a substantial adverse reaction. Carriers may include excipients and other additives such as diluents, detergents, colouring agents, wetting or emulsifying agents, pH buffering agents, preservatives, and the like.

The compositions and combination therapies of the invention may be administered in combination with a variety of pharmaceutical excipients, including stabilizing agents, carriers or encapsulation formulations. Effective combinations are those which provide favourable synergistic effect which assist in treatment and/or prevention and/or immunotherapy better than the agents alone.

As used herein, the term "optionally substituted" means that one or more hydrogen atoms may be replaced by a group or groups selected from: -D, —F, —Cl, —Br, —I, —CF3, —OH, —OR7, —NH2, —NHR7, —NR7R8, —CN, —NO2, —SH, —SR7, —SOR7, —SO2R7, =O, =S, =NOH, =NOR7, —NHOH, —NHOR7, —CHO, where R7 and R8 are independently (C1-C18)alkyl, typically (C1-C12)alkyl; (C3-C18)cycloalkyl, typically (C3-C12)cycloalkyl; (C3-C18)cycloalkyl(C1-C18)alkyl, typically (C3-C12)cycloalkyl(C1-C6)alkyl; (C6-C24)aryl, typically (C6-C16)aryl; (C7-C25)aralkyl, typically (C7-C16)aralkyl; (C2-C18)alkenyl, typically (C2-C12)alkenyl; (C8-C26)aralkenyl, typically (C8-C16)aralkenyl; (C2-C18)alkynyl, typically (C2-C12) alkynyl; (C8-C26)-aralkynyl, typically ($C_8$-$C_{16}$)aralkynyl; or heterocyclic.

As used herein, the term "alkyl" includes within its meaning straight and branched chain alkyl groups. Examples of such groups are methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- or 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5,6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1- or 2-pentylheptyl, and the like.

A used herein, the term "cycloalkyl" refers to mono- or polycyclic alkyl groups, or alkyl substituted cyclic alkyl groups. Examples of such groups include cyclopropyl, methylcyclopropyl, cyclobutyl, methylcyclobutyl, cyclopentyl, methylcyclopentyl, ethylcyclopentyl, cyclohexyl, methylcyclohexyl, ethylcyclohexyl, cycloheptyl, cyclooctyl, cyclononyl, cyclodecyl, cycloundecyl, cyclododecyl, decahydronaphthyl, bicyclo[2.2.1]heptanyl, bicyclo[2.2.2]octanyl, bicyclo[3.3.2]decyl, bicycleo4.4.3]dodecyl, bicyclo [4.4.0]octyl and the like.

As used herein, the term "cycloalkylalkyl" refers to an alkyl group substituted with a cycloalkyl group as defined above.

As used herein, the term "alkenyl" includes within its meaning ethylenically mono-, di- or poly-unsaturated alkyl or cycloalkyl groups as previously defined. Examples of such alkenyl groups are vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-headienyl, 1,4-hexadienyl, 1,3-cyclohexadienyl, 1,4-cyclohexadienyl, 1,3 cycloheptadienyl, 1,3,5-cycloheptatrienyl and 1,3,5,7-cyclooctatetraenyl.

As used herein, the term "alkynyl" includes within its meaning acetylenically unsaturated alkyl groups as previously defined. Examples of such alkynyl groups are ethynyl, propynyl, n-butynyl, n-pentynyl, 3-methyl-1-butynyl, n-hexynyl, methyl-pentynyl, (C7-C12)alkynyl and (C7-C12) cycloalkynyl.

As used herein, the term "alkylidene" refers to optionally unsaturated divalent alkyl radicals. Examples of such radicals are —CH2—, —CH2CH2—, —CH═CH—, —CH2CH2CH2—, —C(═CH2)CH2—, —CH2CH═CH—, —(CH2)4—, —CH2CH2CH═CH—, —CH2CH═CHCH2—, and —(CH2)r- where r is 5-8. The term also refers to such radicals in which one or more of the bonds of the radical from part of a cyclic system. Examples of such radicals are groups of the structures

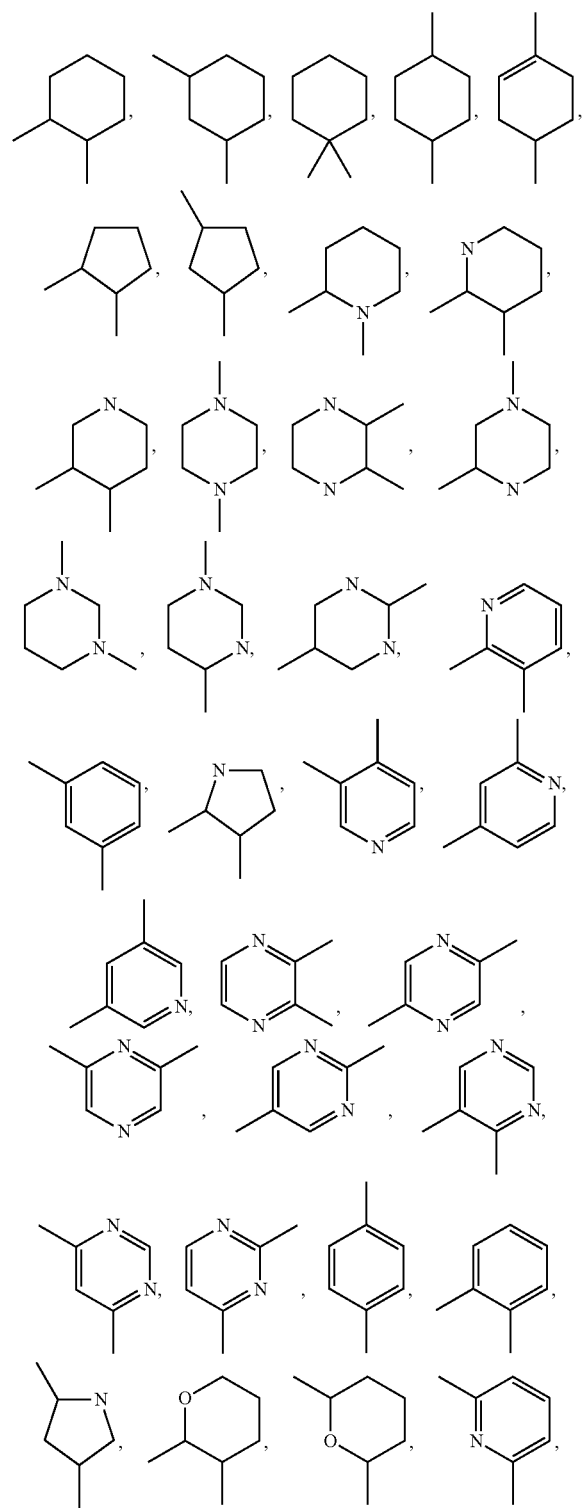

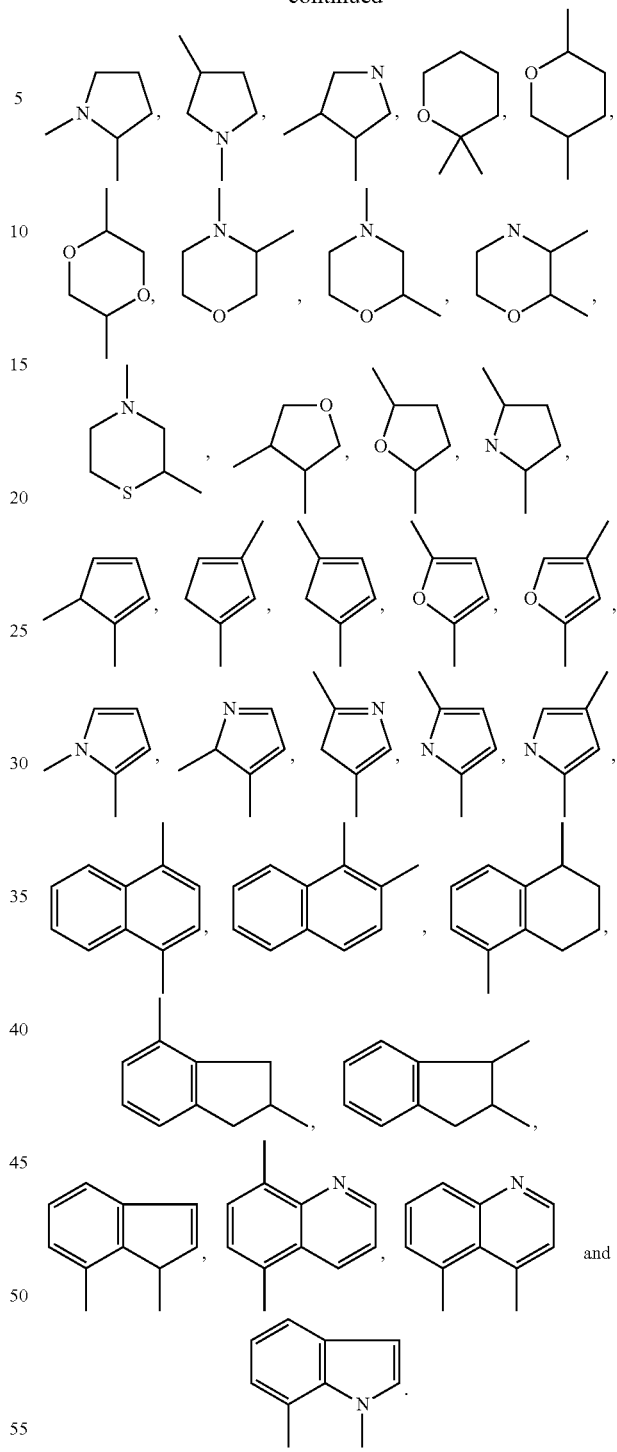

and similar groups wherein any N or O atom is replaced by S or Se.

As used herein, the term "aryl" refers to single, polynuclear, conjugated and fused residues of aromatic hydrocarbons or aromatic heterocyclic ring systems. Examples of such groups are phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, indenyl, azulenyl, chrysenyl, pyridyl, 4-phenylpyridyl, 3-phenylpyridyl, thienyl, furyl, pyrryl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. In all cases, any available position of the fused or conjugated bicyclic system can be used for attachment to the remainder of the molecule of formula (I).

As used herein, the term "aralkyl" refers to alkyl groups substituted with one or more aryl groups as previously defined. Examples of such groups are benzyl, 2-phenylethyl and 1-phenylethyl.

As used herein, the terms "aralkenyl" and "aralkynyl" refer to alkenyl and alkynyl groups respectively, substituted with one or more aryl groups as previously defined. Examples of such groups are styryl, phenylacetylenyl and 2-phenyl-2-butenyl.

As used herein the term "saturated or unsaturated cyclic, bicyclic or fused ring system" refers to a cyclic system of up to 16 carbon atoms, up to 3 of which may be replaced by O, S or N, which ring system may be substituted with one or more of R, —NH2, —NHR, —NR2, —CHO, —C(O)R, —CN, halo, —CF3, —SR, —S(O)R, —S(O)2R, —CONH2, —CONHR, —CONR2, —NHOH, —NHOL, —NO2, =O, =S or —NHNH2; wherein each R are independently as previously defined. Examples of such ring systems are those cyclic alkylidene groups exemplified above and

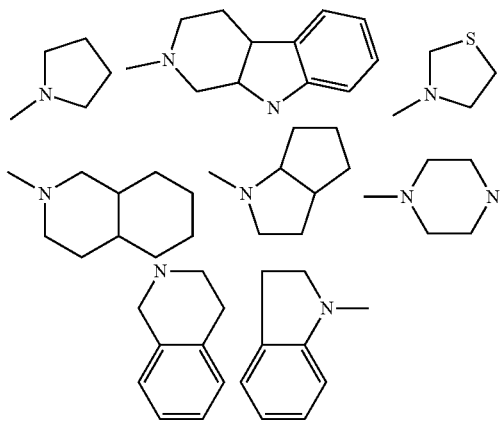

As used herein, the term "heterocyclic" refers to any 3- to 16-membered monocyclic, bicyclic or polycyclic ring containing, for 3- and 4-membered rings, one heteroatom; for 5-membered rings, one or two heteroatoms; for 6- and 7-membered rings, one to three heteroatoms; for 8- and 9-membered rings, from one to four heteroatoms; for 10- and 11-membered rings, from one to five heteroatoms; for 12- and 13-membered rings, from one to six heteroatoms; for 14- and 15-membered rings, from one to seven heteroatoms; and for 16-membered rings, from one to eight heteroatoms; the heteroatom(s) being independently selected from oxygen, nitrogen and sulphur. The term "heterocyclic" includes any group in which a heterocyclic ring is fused to a benzene ring. Examples of heterocyclics are pyrryl, pyrimidinyl, quinolinyl, isoquinolinyl, indolyl, piperidinyl, pyridinyl, furyl, thiophenyl, tetrahydrofuryl, imidazolyl, oxazolyl, thiazolyl, pyrenyl, oxazolidinyl, isoxazolyl, isothiazolyl, isoxazolidinyl, imidazolidinyl, morpholinyl, pyrrolidinyl, pyrazolyl, pyrazolinyl, furfuryl, thienyl, benzothienyl, benzoxazolyl, benzisoxazolyl, benzothiazolyl, benzoisothiazolyl, benzothiadiazolyl, tetrazolyl, triazolyl, thiadiazolyl, benzimidazolyl, pyrrolinyl, quinuclidinyl, azanorbornyl, isoquinuclidi-nyl and the like. Nitrogen-containing heterocyclics may be substituted at nitrogen with an oxygen atom. Sulfur-containing heterocyclics may be substituted at sulfur with one or two oxygen atoms.

Configurations which result in unstable heterocyclics are not included within the scope of the definition of "heterocyclic" or "saturated or unsaturated cyclic, bicyclic or fused ring system".

As used herein, the term "alkylheterocyclic" refers to a heterocyclic group as defined above, which is substituted with an alkyl group as defined above.

As used herein, the term "heterocyclic-oxy-alkyl" refers to a group of the formula heterocyclic-O-alkyl, wherein the heterocyclic and alkyl are as defined above.

As used herein, the term "alkoxy" refers to a group of the formula alkyl-O—, wherein the alkyl group is as defined above.

As used herein, the term "aryloxy" refers to a group of the formula aryl-O—, wherein the aryl group is as defined above.

As used herein, the term "alkanoyloxy" refers to a group of the formula alkyl-C(O)O—, wherein the alkyl group is as defined above.

As used herein, the term group (a) refers to five member saturated or unsaturated cyclic or heterocyclic ring systems. Examples of such ring systems are:

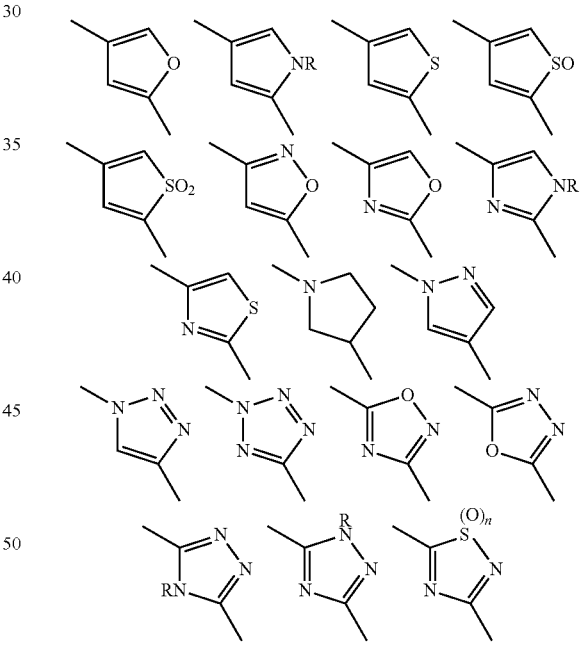

As used herein, the term group (b) refers to five member unsaturated cyclic or heterocyclic ring systems. Examples of such ring systems are:

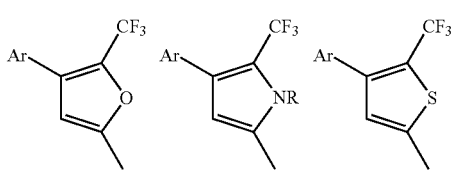

-continued

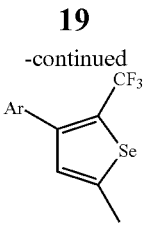

wherein each Ar and R are independently as previously defined and S and Se can be in the oxidized form S(O), S(O)$_2$ and Se(O) and Se(O)$_2$ respectively.

As used herein, the term group (c) refers to five-six bicyclic member ring systems. Examples of such ring systems are:

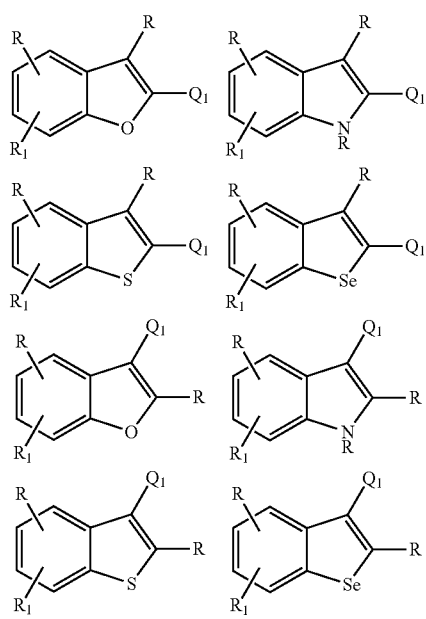

wherein each R, R$_1$ and Q$_1$ are independently as previously defined and S and Se can be in the oxidized form such as S(O), S(O)$_2$ and Se(0) and Se(O)$_2$ respectively.

As used herein, the term group (d) refers to six-six hetero-bicyclic member ring system. Examples of such ring systems are:

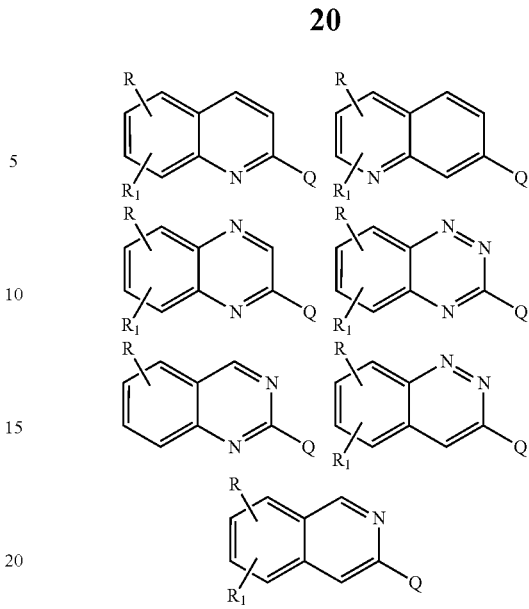

wherein each R, R$_1$ and Q are independently as previously defined.

The compound preparations illustrated can be carried out by generally known methods as exemplified hereinafter. The starting materials and intermediates used in the synthesis of compounds of this invention are generally commercially available or may be prepared by conventional methods of organic chemistry. Suitable methods for the synthesis of compounds of this invention and intermediates thereof are described, for example, in Houben-Weyl, *Methoden der Organischen Chemie*; J. March, *Advanced Organic Chemistry*, 3rd Edition (John Wiley & Sons, New York, 1985); D. C. Liotta and M. Volmer, eds, *Organic Syntheses Reaction Guide* (John Wiley & Sons, Inc., New York, 1991); R. C. Larock, *Comprehensive Organic Transformations* (VCH, New York, 1989), H. O. House, *Modern Synthetic Reactions* 2nd Edition (W. A. Benjamin, Inc., Menlo Park, 1972); N. S. Simpkins, ed. 100 *Modern Reagents* (The Royal Society of Chemistry, London, 1989); A. H. Haines *Methods for the Oxidation of Organic Compounds* (Academic Press, London, 1988) and B. J. Wakefield *Organolithium Methods* (Academic Press, London, 1988).

Representative compounds in accordance with the invention are described in the following Tables.

TABLE 1

Compounds of formula

| S. N. | R | X—Y | G1 | G2 |
|---|---|---|---|---|
| 1 | CF3 | —CH2—CH2— | HN-CH2CH2-COOH | N-azetidine-COOH |
| 2 | Me | —O—(CH2)3— | N-azetidine-COOH | N-piperidine-OH |

TABLE 1-continued

Compounds of formula

| S. N. | R | X—Y | G1 | G2 |
|---|---|---|---|---|
| 3 | CH2CF3 | —CH2—O— | 1-piperidinyl-4-COOH | —HN—CH(CH2OH)2 |
| 4 | Ph | —CH2—O— | 2-amino-pyridin-5-yl-COOH | 1-azetidinyl-3-COOH |
| 5 | pyridin-2-yl | —CH2—CH2— | —HN—CH2CH2—COOH | —HN—C(O)—NH—CH2CH2—COOH |
| 6 | pyridin-3-yl | —CH2—CH2— | —HN—(4-cyclohexyl-COOH) | —HN—C(O)—NH—CH2CH2—COOH |
| 7 | thien-2-yl | —CH2—O— | —HN—CH2CH2—COOH | —HN—C(O)—NH—CH2CH2—COOH |
| 8 | thien-3-yl | —CH2—O— | —HN—CH2CH2—COOH | 1-azetidinyl-3-COOH |
| 9 | furan-3-yl | —CH2—O— | —HN—(4-cyclohexyl-COOH) | —HN—C(O)—NH—CH2CH2—COOH |
| 10 | furan-2-yl | —CH2—O— | —HN—CH2CH2—COOH | —HN—C(O)—NH—CH2CH2—COOH |
| 11 | 1H-pyrrol-3-yl | —CH2—O— | —HN—CH2CH2—COOH | 1-azetidinyl-3-COOH |
| 12 | 1-methyl-pyrrol-3-yl | —CH2—O— | —HN—(4-cyclohexyl-COOH) | —HN—CH2-(tetrazol-5-yl) |

TABLE 1-continued
Compounds of formula
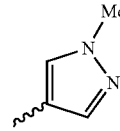
| S. N. | R | X—Y | G1 | G2 |
|---|---|---|---|---|
| 13 | 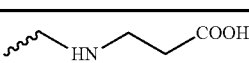 | —CH2—O— | 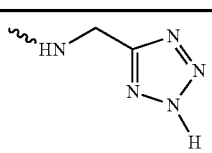 | 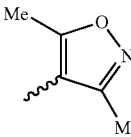 |
| 14 | 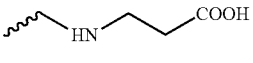 | —CH2—O— |  | 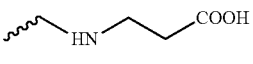 |
| 15 | —CH2—CF3 | —NH—SO2— | 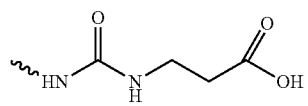 | 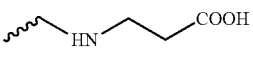 |
| 16 | —CF3 | |  | 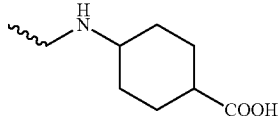 |
| 17 | —CH2—CF3 | —C≡C— |  | 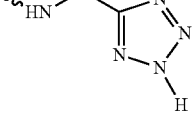 |
| 18 | Me | —CH=CH— | 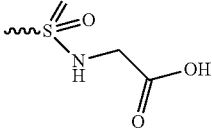 | 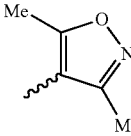 |
| 19 | 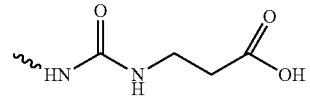 | —C≡C— | 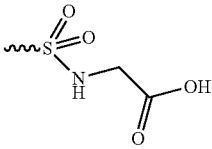 | 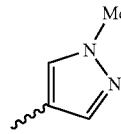 |
| 20 | 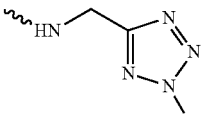 | —C≡C— | 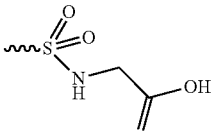 | 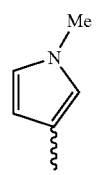 |
| 21 | 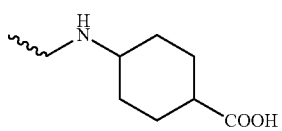 | —C≡C— |  | (see above) |

TABLE 1-continued

Compounds of formula

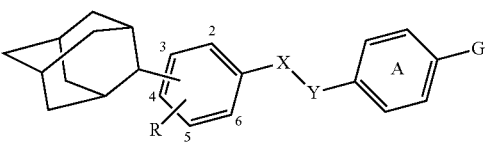

| S. N. | R | X—Y | G1 | G2 |
|---|---|---|---|---|
| 22 | pyrrole (N-H) | —C≡C— | ∼HN-CH2CH2-COOH | ∼HN-CH2-tetrazole(NH) |
| 23 | furan-2-yl | —C≡C— | ∼HN-C(O)-NH-CH2CH2-COOH | ∼S(O)2-NH-CH2-COOH |
| 24 | furan-3-yl | —C≡C— | ∼NH-cyclohexyl-COOH | ∼N-azetidine-COOH |
| 25 | thiophen-2-yl | —C≡C— | ∼HN-C(O)-NH-CH2CH2-COOH | ∼S(O)2-NH-CH2-COOH |
| 26 | thiophen-3-yl | —C≡C— | ∼HN-CH2CH2-COOH | ∼N-azetidine-COOH |
| 27 | pyridin-3-yl | —C≡C— | ∼NH-cyclohexyl-COOH | ∼HN-CH2-tetrazole(NH) |
| 28 | pyridin-2-yl | —C≡C— | ∼HN-C(O)-NH-CH2CH2-COOH | ∼N-azetidine-COOH |
| 29 | OMe | —CH2—O— | ∼HN-C(O)-NH-CH2CH2-COOH | ∼S(O)2-NH-CH2-COOH |
| 30 | OCH2CF3 | —CH2—O— | ∼NH-cyclohexyl-COOH | ∼N-azetidine-COOH |

TABLE 1-continued

Compounds of formula

| S. N. | R | X—Y | G1 | G2 |
|---|---|---|---|---|
| 31 | OMe | 1,3,4-oxadiazole | -HN-CH2-CH2-COOH | -HN-CH2-tetrazole |
| 32 | OCH2CF3 | 1,2,4-oxadiazole | -HN-CH2-tetrazole | -HN-C(O)-NH-CH2CH2-COOH |
| 33 | OMe | isoxazole | -HN-cyclohexyl-COOH | -HN-CH2-tetrazole |
| 34 | OMe | isoxazole | azetidine-COOH | -HN-C(O)-NH-CH2CH2-COOH |
| 35 | OCH2CF3 | -C(O)-CH=CH- | -HN-CH2-CH2-COOH | -HN-C(O)-NH-CH2CH2-COOH |
| 36 | CF3 | —OCH2—CH2O— | azetidine-COOH | -HN-CH2-tetrazole |
| 37 | CN | —CH2O— | -HN-cyclohexyl-COOH | -HN-CH2-tetrazole |
| 38 | N(Me)2 | —CH2—CH2— | azetidine-COOH | -HN-C(O)-NH-CH2CH2-COOH |
| 39 | OEt | —CH2O— | azetidine-COOH | -HN-C(O)-NH-CH2CH2-COOH |
| 40 | OPr | —CH2O— | azetidine-COOH | -HN-C(O)-NH-CH2CH2-COOH |

TABLE 1-continued

Compounds of formula

| S. N. | R | X—Y | G1 | G2 |
|---|---|---|---|---|
| 41 | OPr | —CH2O—, —CH2CH2— | HN–CH(CH2OH)2 (2-amino-1,3-propanediol) | HN–CH2–(2H-tetrazol-5-yl) | and variations thereof.
G1 and G2 represent alternative groups for G

TABLE 2

Compounds of Formula (chromone scaffold: G–phenyl–chromen-4-one with $R_1$ at 2-position)

(chalcone scaffold: G–biphenyl–C(O)–CH=C($R_1$)($R_2$))

| S. N. | R1 | R2 | G |
|---|---|---|---|
| 1 | 4-F-phenyl | —CH3 | —HN–C(O)–NH–CH2CH2–COOH |
| 2 | 4-CF3-phenyl | —CH2CH2CH3 | pyrazol-1-yl–CH2–COOH (linked via 4-position) |
| 3 | 3,5-bis(CF3)-phenyl | —CH3 | HN–CH2–(2H-tetrazol-5-yl) |
| 4 | 2-F-5-CN-phenyl | —CH3 | azetidin-1-yl-3-COOH |

TABLE 2-continued

Compounds of Formula

| S. N. | R1 | R2 | G |
|---|---|---|---|
| 5 | 3,4-difluorophenyl | adamantyl | azetidine-3-carboxylic acid (N-linked) |
| 6 | 4-methoxyphenyl | adamantyl | 2-(1H-imidazol-1-yl)acetic acid, 2-ethyl-linked |
| 7 | —CH2CF3 | Ph | —HN-CH2CH2-COOH |
| 8 | —Me | Ph | —HN-CH2CH2-COOH |
| 9 | 4-fluorophenyl | adamantyl | —HN-CH2-(2H-tetrazol-5-yl) |
| 10 | 4-CF3-phenyl | isobutyl | —HN-CH2-(2H-tetrazol-5-yl) |
| 11 | 3,5-bis(trifluoromethyl)phenyl | isobutyl | azetidine-3-carboxylic acid (N-linked) |
| 12 | adamantyl | isobutyl | —HN-CH2CH2-COOH |
| 13 | 3,4-difluorophenyl | isobutyl | 2-(1H-imidazol-1-yl)acetic acid, 2-ethyl-linked |

TABLE 2-continued

Compounds of Formula

| S. N. | R1 | R2 | G |
|---|---|---|---|
| 14 | 3,4-difluorophenyl | isobutyl | -HN-CH2-(2H-tetrazol-5-yl) |
| 15 | adamantyl | isobutyl | N-azetidinyl-3-COOH |
| 16 | adamantyl | norbornyl | N-azetidinyl-3-COOH |
| 17 | 4-CF3-phenyl | norbornyl | -HN-CH2-(2H-tetrazol-5-yl) |
| 18 | 3,5-bis(CF3)phenyl | norbornyl | -HN-CH2CH2-COOH |
| 19 | 3-CN-4-F-phenyl | norbornyl | 2-(1H-imidazol-1-yl-CH2COOH)ethyl |
| 20 | 4-F-phenyl | adamantylmethyl | N-azetidinyl-3-COOH |

TABLE 2-continued

Compounds of Formula

| S. N. | R1 | R2 | G |
|---|---|---|---|
| 21 | 4-CF₃-phenyl | adamantyl | -HN-CH₂CH₂-COOH |
| 22 | 3,5-bis(CF₃)-phenyl | adamantyl | imidazolyl-CH₂-COOH (2-substituted ethyl linker) |
| 23 | 2-F, 5-CN-phenyl | adamantyl | -HN-CH₂-tetrazole |
| 24 | 3,4-difluorophenyl | norbornyl | -HN-CH₂CH₂-COOH |
| 25 | 4-OMe-phenyl | norbornyl | azetidine-N-, 3-COOH |
| 26 | 4-OMe-phenyl | —CH2CF3 | -HN-CH₂-tetrazole |
| 27 | 3,4-difluorophenyl | —CH2CF3 | -HN-CH₂CH₂-COOH |
| 28 | 4-CF₃-phenyl | —CH2CF3 | azetidine-N-, 3-COOH |

TABLE 2-continued

Compounds of Formula

[Structure: 6-(4-G-phenyl)-2-R₁-4H-chromen-4-one]

[Structure: 4'-G-biphenyl-4-yl C(=O)-CH=C(R₁)(R₂)]

| S. N. | R1 | R2 | G |
|---|---|---|---|
| 29 | 3,5-bis(trifluoromethyl)phenyl | —CH2CF3 | —HN—CH2—(2H-tetrazol-5-yl) |
| 30 | 2-fluoro-6-cyanophenyl | —CH2CF3 | —HN—CH2—(2H-tetrazol-5-yl) |
| 31 | 4-methoxyphenyl | H, Me | —HN—CH(CH2OH)2 |
| 32 | but-1-en-1-yl | H, Me | —HN—CH(CH2OH)2 |
| 33 | 4-propylphenyl | H, Me | —HN—CH(CH2OH)2 | and variations thereof.

TABLE 3

Compounds of formula

[Structure: R₁R₂N—Y—X—C₆H₄—G]

| S. N. | R1 | R2 | X | Y | G |
|---|---|---|---|---|---|
| 1 | 4-fluorophenyl | isobutyl | —CH2— | Ph | —HN—C(=O)—NH—CH2CH2—C(=O)OH |

TABLE 3-continued

Compounds of formula

| S. N. | R1 | R2 | X | Y | G |
|---|---|---|---|---|---|
| 2 | 4-CF3-phenyl | isobutyl | CH2 | Ph | pyrazol-1-yl-CH2-COOH (4-linked) |
| 3 | 3,5-bis(CF3)-phenyl | isobutyl | CH2 | 2,5-thienyl | -HN-CH2-(2H-tetrazol-5-yl) |
| 4 | 3-CN-4-F-phenyl | isobutyl | —SO2— | Ph | azetidin-1-yl-3-COOH |
| 5 | 3,4-difluorophenyl | isobutyl | —CO— | Ph | azetidin-1-yl-3-COOH |
| 6 | 4-OMe-phenyl | isobutyl | —CH2— | —CH2CH2— | imidazol-1-yl-CH2-COOH (2-linked) |
| 7 | —CH2CF3 | 1-adamantyl | —CH2— | Ph | -HN-CH2CH2-COOH |
| 8 | —Me | 1-adamantyl | —CH2— | Ph | -HN-CH2CH2-COOH |
| 9 | 4-F-phenyl | isobutyl | —CH2— | 2,5-thienyl | -HN-CH2-(2H-tetrazol-5-yl) |
| 10 | 4-CF3-phenyl | isobutyl | —CH2— | 2,5-thiazolyl | -HN-CH2-(2H-tetrazol-5-yl) |

TABLE 3-continued

Compounds of formula

R1R2N-Y-X-C6H4-G (para)

| S. N. | R1 | R2 | X | Y | G |
|---|---|---|---|---|---|
| 11 | 3,5-bis(trifluoromethyl)phenyl | isobutyl | —CH2— | 2,5-dimethylthiazole | azetidine-3-COOH (N-linked) |
| 12 | 3-cyano-4-fluorophenyl | isobutyl | —CO— | 2,5-dimethylthiophene | —NH-CH2CH2-COOH |
| 13 | 3,4-difluorophenyl | isobutyl | —CH2— | —CH2CH2— | 2-ethyl-imidazol-1-yl-acetic acid |
| 14 | 2,3-difluorophenyl | isobutyl | —CO— | —CH2CH2— | —NH-CH2-(2H-tetrazol-5-yl) |
| 15 | 4-methoxyphenyl | isobutyl | —CH2— | 2,5-dimethylthiophene | azetidine-3-COOH (N-linked) |
| 16 | 4-methoxyphenyl | norbornyl | —CH2— | —CH2CH2— | azetidine-3-COOH (N-linked) |
| 17 | 4-(trifluoromethyl)phenyl | norbornylmethyl | —CH2— | 2,5-dimethylthiophene | —NH-CH2-(2H-tetrazol-5-yl) |
| 18 | 3,5-bis(trifluoromethyl)phenyl | norbornylmethyl | —CH2— | —CH2CH2— | —NH-CH2CH2-COOH |
| 19 | 3-cyano-4-fluorophenyl | norbornylmethyl | —CH2— | —CH2CH2— | 2-ethyl-imidazol-1-yl-acetic acid |

TABLE 3-continued

Compounds of formula

R1–N(R2)–Y–X–C6H4–G

| S. N. | R1 | R2 | X | Y | G |
|---|---|---|---|---|---|
| 20 | 4-F-phenyl | 1-adamantyl | —CH2— | 2,5-thienyl | N-azetidinyl-3-COOH |
| 21 | 4-CF3-phenyl | 1-adamantyl | —CH2— | 2,5-thienyl | —HN-CH2CH2-COOH |
| 22 | 3,5-(CF3)2-phenyl | 1-adamantyl | —SO2— | Ph | 1-(imidazol-1-yl)-2-CH2COOH (N-CH2COOH imidazole) |
| 23 | 2-F-5-CN-phenyl | 1-adamantyl | —CH2— | —CH2CH2— | —HN-CH2-(tetrazol-5-yl) |
| 24 | 3,4-difluorophenyl | 2-norbornyl | —CH2— | 2,5-thiazolyl | —HN-CH2CH2-COOH |
| 25 | 4-OMe-phenyl | 2-norbornyl | —CH2— | —CH2CH2— | N-azetidinyl-3-COOH |
| 26 | 4-OMe-phenyl | —CH2CF3 | —CO— | —CH2CH2— | —HN-CH2-(tetrazol-5-yl) |
| 27 | 3,4-difluorophenyl | CH2CF3 | —CH2— | 2,5-thiazolyl | —HN-CH2CH2-COOH |
| 28 | 4-CF3-phenyl | —CH2CF3 | —SO2— | Ph | N-azetidinyl-3-COOH |
| 29 | 3,5-(CF3)2-phenyl | —CH2CF3 | —CH2— | 2,5-thiazolyl | —HN-CH2-(tetrazol-5-yl) |

TABLE 3-continued

Compounds of formula

R1\N(R2)-Y-X-C6H4-G

| S. N. | R1 | R2 | X | Y | G |
|---|---|---|---|---|---|
| 30 | 2-F, 5-CN-phenyl | —CH2CF3 | —CH2— | Ph | —HN-CH2-(1H-tetrazol-5-yl) |
| 31 | 3-Cl, 4-OPr-phenyl | Me | —CH2— | —CH2— | —HN-CH(CH2OH)2 |
| 32 | n-Hexyl | Me | CH2— | CH2— | —HN-CH(CH2OH)2 | and variations thereof.

TABLE 4

Compounds of formula

R-CH2-X-C6H3(R1)-G

| Compound No. | R | X | R1 | G |
|---|---|---|---|---|
| 1 | 6-MeO-benzofuran-2-yl | —CH2— | H | piperazin-1-yl-CH2-COOH |
| 2 | 6-MeO-benzofuran-2-yl | —CH2— | Cl | piperazin-1-yl-CH2-COOH |
| 3 | 6-MeO-benzofuran-3-yl | —CH2— | CF3 | piperazin-1-yl-CH2-COOH |
| 4 | 6-MeO-indol-2-yl (N-R) | —CH2— | CF3 | piperazin-1-yl-CH2-COOH |
| 5 | 6-MeO-indol-2-yl (N-R) | —O— | iPr | —NH-C(O)-NH-CH2CH2-COOH |

TABLE 4-continued

Compounds of formula

| Compound No. | R | X | R1 | G |
|---|---|---|---|---|
| 6 | 6-MeO-2-methyl-indole (N-R) | —S— | H | urea-CH2CH2-COOH (—NH-C(O)-NH-CH2CH2-COOH) |
| 7 | 4,6-dichloro-2-methyl-benzofuran | —O— | adamantyl | piperazine-CH2-COOH |
| 8 | 4,6-dichloro-3-methyl-benzofuran | —CH2— | Me | urea-CH2CH2-COOH |
| 9 | 4,6-dichloro-2-methyl-benzothiophene | —O— | H | piperazine-CH2-COOH |
| 10 | 6-MeO-2-methyl-3-(3,4,5-trimethoxybenzoyl)-benzofuran | —CH2— | H | urea-CH2CH2-COOH |
| 11 | 6-iPr-X-2-methyl-benzofuran | —O— | CF3 | piperazine-CH2-COOH |
| 12 | 6-iPr-X-2-methyl-3-CF3-benzofuran | —O—, —CH2—, —S— | H | piperazine-CH2-COOH |
| 13 | 6-CF3-2-methyl-3-CF3-furo[2,3-b]pyridine | —O— | Cl | piperazine-CH2-COOH |

TABLE 4-continued

Compounds of formula

| Compound No. | R | X | R1 | G |
|---|---|---|---|---|
| 14 | F₃C-furan-phenyl | —O— | F | piperazine-CH₂COOH |
| 15 | F₃C-thiophene-phenyl | —O— | CF₃CF₂ | piperazine-CH₂COOH |
| 16 | F₃C-selenophene-phenyl | —O— | F | piperazine-CH₂COOH | and variations thereof.

TABLE 5

Compounds of formula

| Compound No. | ring | R | R1 | R2 | G |
|---|---|---|---|---|---|
| 1 | 1,2,4-oxadiazole | iPrO— | adamantyl | H | piperazine-CH₂COOH |
| 2 | 1,2,4-oxadiazole | iPrO— | adamantyl | H | —NHC(O)NHCH₂CH₂COOH |

TABLE 5-continued

Compounds of formula

| Compound No. | ⬡ | R | R1 | R2 | G |
|---|---|---|---|---|---|
| 3 | 3-methyl-1,2,4-oxadiazol-5-yl | iPrO— | adamantyl | 3-CF3 | piperazinyl-CH2-COOH |
| 4 | 3-methyl-1,2,4-oxadiazol-5-yl | MeO— | Cl | 3-F | piperazinyl-CH2-COOH |
| 5 | 3-methyl-1,2,4-oxadiazol-5-yl | Cl | Cl | 2-Me | piperazinyl-CH2-COOH |
| 6 | 3-methyl-1,2,4-oxadiazol-5-yl | Me | CF3 | CF3 | -NH-C(O)-NH-CH2CH2-COOH |
| 7 | 3-methyl-1,2,4-oxadiazol-5-yl | i-Pr | CF3 | H | -NH-C(O)-NH-CH2CH2-COOH |
| 8 | 3-methyl-1,2,4-oxadiazol-5-yl | n-Bu | F | 3-Cl | piperazinyl-CH2-COOH |
| 9 | 3-methyl-1,2,4-oxadiazol-5-yl | | adamantyl (as R1) Br | H | piperazinyl-CH2-COOH |
| 10 | 5-methyl-1,2,4-oxadiazol-3-yl | iPrO— | adamantyl | H | piperazinyl-CH2-COOH |
| 11 | 3-methyl-1H-1,2,4-triazol-5-yl | Cl | Cl | 2-Me | -NH-C(O)-NH-CH2CH2-COOH |
| 12 | 1-methyl-1H-tetrazol-5-yl | i-Pr | CF3 | 2-Me | -NH-C(O)-NH-CH2CH2-COOH |

TABLE 5-continued

Compounds of formula

[Structure: biphenyl with central ring, R/R1 on left ring, R2 and G on right ring]

| Compound No. | ⟨ring⟩ | R | R1 | R2 | G |
|---|---|---|---|---|---|
| 13 | 3,5-disubstituted-1,2,4-oxadiazole | adamantyl | CF3 | H | piperazinyl-CH2-C(O)OH |
| 14 | 3,5-disubstituted-1,2,4-oxadiazole | n-Pr | CN | 3-Me | —NHC(O)NH—CH2CH2—C(O)OH |
| 15 | 3,5-disubstituted-1,2,4-oxadiazole | nPr | H | 2-isoPr | —NHC(O)NH—CH2CH2—C(O)OH | and variations thereof.

TABLE 6

Compounds of formula

[Structure: substituted phenyl–ring–benzofuran/indole/benzothiophene with CH(NH2)C(CH2OR3)(OH) side chain]

| Compound No. | ⟨ring⟩ | X | R1 | R2 | R3 |
|---|---|---|---|---|---|
| 1 | 3,5-disubstituted-1,2,4-oxadiazole | O | OEt | OEt | H |
| 2 | 3,5-disubstituted-1,2,4-oxadiazole | N | OEt | OEt | H |
| 3 | 3,5-disubstituted-1,2,4-oxadiazole | O | —OEt | —OEt | —OP(O)(OH)$_2$— and or salt of choice |
| 4 | 3,5-disubstituted-1,2,4-oxadiazole | O | —OiPr | —Cl | —H |
| 5 | 3,5-disubstituted-1,2,4-oxadiazole | S | —O—Et | —OEt | —H |

TABLE 6-continued
Compounds of formula
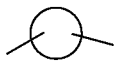
| Compound No. | 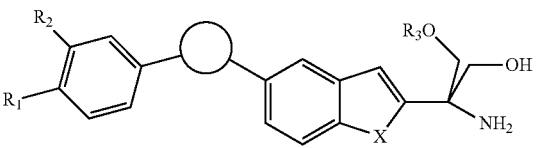 | X | R1 | R2 | R3 |
|---|---|---|---|---|---|
| 6 | 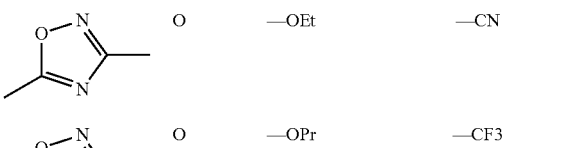 | O | —O—Pr | —OMe | —H |
| 7 | 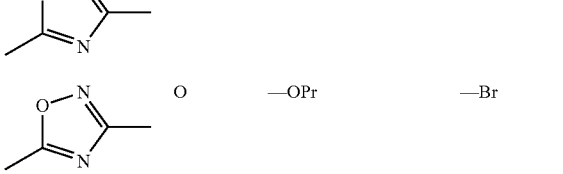 | O | —OEt | —CN | —H |
| 8 | 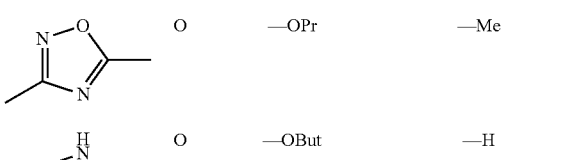 | O | —OPr | —CF3 | —H |
| 9 | 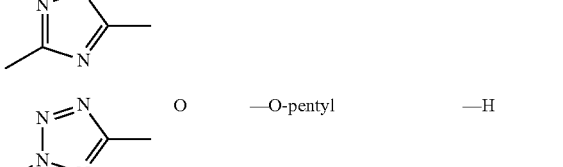 | O | —OPr | —Br | —H |
| 10 | 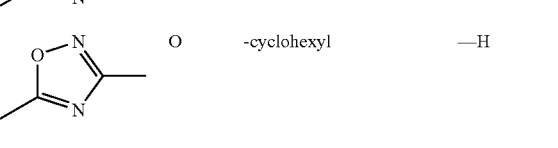 | O | —OPr | —Me | —H |
| 11 |  | O | —OBut | —H | —H |
| 12 |  | O | —O-pentyl | —H | —H |
| 13 |  | O | -cyclohexyl | —H | —H |
| 14 |  | O | —N(Et)2 | —H | —H |
| 15 | 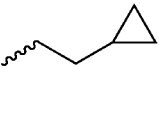 | O | —OEt | 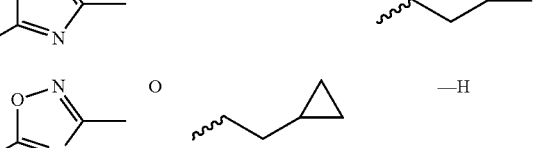 | —H |
| 16 | 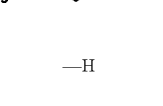 | O | —OMe |  | —H |
| 17 | 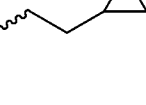 | O | (cyclopropylethyl) | —H | —H |

TABLE 6-continued

Compounds of formula

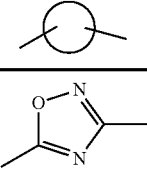

| Compound No. | ⟨circle⟩ | X | R1 | R2 | R3 |
|---|---|---|---|---|---|
| 18 | 3,5-dimethyl-1,2,4-oxadiazole | S | -nPr | —H | —H | and variations thereof.

TABLE 7

Compound of formula

| Compound No. | Ar | X | R3 |
|---|---|---|---|
| 1 | 3-chloro-2-ethoxypyridin-5-yl | O | H |
| 2 | 3-chloro-2-propoxypyridin-5-yl | N | H |
| 3 | 2-ethylbenzofuran-5-yl | O | H |
| 4 | 2-methylbenzoxazol-5-yl | O | H |
| 5 | 2-methylbenzothiazol-5-yl | S | H |
| 6 | quinoxalin-2-yl | O | H |
| 7 | 4-methylstyryl | O | H |
| 8 | adamantyl-vinyl | O | H |
| 9 | 3-chloro-2-ethylaminopyridin-5-yl | O | H |
| 10 | 2-diethylaminopyridin-5-yl | O | H |
| 11 | 3-chloro-2-piperidin-1-ylpyridin-5-yl | O | H |
| 12 | 2-ethyl-1H-benzimidazol-5-yl | O | H |
| 13 | 6-propylpyridin-3-yl | O | H |

TABLE 7-continued

Compound of formula

![Structure: Ar-oxadiazole-benzofuran(X)-C(NH2)(CH2OR3)(CH2OH), X = O, N, S]

| Compound No. | Ar | X | R3 |
|---|---|---|---|
| 14 | 2-pentylpyridin-5-yl | O | H |
| 15 | oct-2-enyl (alkenyl chain) | O | H |
| 16 | 1-butylpyrazol-4-yl | O | H | and variations thereof.

TABLE 8

Compound of formula

![Structure: T-substituted benzofuran/analog(A,X) with R' at 6/7, connected to C(NH2)(CH2OR)(CH2OH)]

| Compound No. | T | R | R' |
|---|---|---|---|
| 1 | 5-(4-EtO-phenyl)-1,2,4-oxadiazol-3-yl | OH | 6-Cl |
| 2 | 5-(4-Pr-phenyl)-1,2,4-oxadiazol-3-yl | OH | 7-isoprpyl |
| 3 | 5-(6-Pr-pyridin-3-yl)-1,2,4-oxadiazol-3-yl | OH | 6-Cl |
| 4 | 5-(5-Pr-pyridin-2-yl)-1,2,4-oxadiazol-3-yl | OH | H |
| 5 | 5-(4-Pr-phenyl)-1,2,4-oxadiazol-3-yl | OH | 7-Me |
| 6 | 5-(4-Pr-phenyl)-1,2,4-oxadiazol-3-yl | OH | 7-Et |

TABLE 8-continued

Compound of formula

![Structure: same as Table 8]

| Compound No. | T | R | R' |
|---|---|---|---|
| 7 | 5-(4-Pr-phenyl)-1,2,4-oxadiazol-3-yl | OH | 7-(2-methylprop-1-enyl) |
| 8 | 5-(4-EtO-3-cyano-phenyl)-1,2,4-oxadiazol-3-yl | OH | 6-Cl |
| 9 | 5-(4-EtO-3-Cl-phenyl)-1,2,4-oxadiazol-3-yl | OH | 6-Cl |
| 10 | 5-Pr-benzofuran-2-yl-CH2-X | OH | H |
| 11 | 2-(s-phenyl)-5-methyl-oxazol-4-yl-CH2CH2-X | OH | H |
| 12 | N-methyl-N-(pyridin-2-yl)aminoethyl-X | OH | H |
| 13 | n-Octyl | OH | n-Octyl |

And variations thereof.
s represents a ring subsituent.

TABLE 9

Compound of formula

![Structure: T-substituted bicyclic (A, X, Y, G) with R' at 6/7]

X, Y and G are as defined for formula (I).

| Compound No. | T | R | R' |
|---|---|---|---|
| 1 | 5-(4-EtO-phenyl)-1,2,4-oxadiazol-3-yl | OH | 6-Cl |

TABLE 9-continued

Compound of formula

[Structure: bicyclic ring A with T at position 5, position 4=Y, X-G, R' at position 7]

X, Y and G are as defined for formula (I).

| Compound No. | T | R | R' |
|---|---|---|---|
| 2 | Pr—[phenyl]—[1,3,4-oxadiazole] | OH | 7-isoprpyl |
| 3 | Pr—[pyridyl]—[1,3,4-oxadiazole] | OH | 6-Cl |
| 4 | Pr—[pyridyl]—[1,3,4-oxadiazole] | OH | H |
| 5 | Pr—[phenyl]—[1,3,4-oxadiazole] | OH | 7-Me |
| 6 | Pr—[phenyl]—[1,3,4-oxadiazole] | OH | 7-Et |
| 7 | Pr—[phenyl]—[1,3,4-oxadiazole] | OH | 7-[isobutenyl] |
| 8 | EtO,NC—[phenyl]—[1,3,4-oxadiazole] | OH | 6-Cl |
| 9 | EtO,Cl—[phenyl]—[1,3,4-oxadiazole] | OH | 6-Cl |
| 10 | Pr—[benzofuran]—CH2— | OH | H |
| 11 | s—[phenyl]—[methyloxazole]—CH2CH2— | OH | H |
| 12 | [pyridyl]-N(Me)-CH2CH2— | OH | H |
| 13 | n-Octyl | OH | n-Octyl |

And variations thereof.

s represents a ring substituent.

Methods of Synthesis:

The examples (28) to (30) were prepared by the use of following procedure as in Scheme-1

Scheme - 1

[Reaction scheme showing:
- Aldehyde (X, R substituted benzaldehyde) + R'-C≡C-MgX → via i(a-b) → α,β-unsaturated ketone → via ii → vinyl bromide intermediate → via iii or iv → chromone (R, X, R' substituted) or chalcone-type product]

X = H, OPr
R = substituent

R = R' = substituent    R = R' = R" = substituent (i a) THF, stirring; (i b) MnO₂/Dioxane reflux; (ii) HBr/AcOH; (iii) Pd(PPh₃)₂, RB(OH)₂, NaHCO₃/Dioxane, H₂O, 80° C. - reflux; (iv) K₂CO₃.

The examples (36) to (52) were prepared by the use of following procedure as in Scheme-2 (a-b).

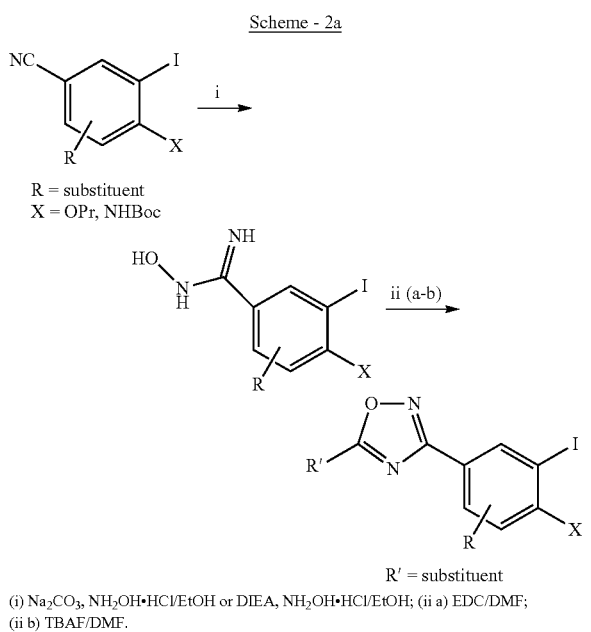

Scheme - 2a

R = substituent
X = OPr, NHBoc

R' = substituent
(i) Na₂CO₃, NH₂OH•HCl/EtOH or DIEA, NH₂OH•HCl/EtOH; (ii a) EDC/DMF; (ii b) TBAF/DMF.

the synthesis of compounds of this invention and intermediates thereof are described, for example, in Houben-Weyl, Methoden der Organischen Chemie; J. March, Advanced Organic Chemistry, 3rd Edition (John Wiley & Sons, New York, 1985); D. C. Liotta and M. Volmer, eds, Organic Syntheses Reaction Guide (John Wiley & Sons, Inc., New York, 1991); R. C. Larock, Comprehensive Organic Transformations (VCH, New York, 1989), H. O. House, Modern Synthetic Reactions 2nd Edition (W. A. Benjamin, Inc., Menlo Park, 1972); N. S. Simpkins, ed. 100 Modern Reagents (The Royal Society of Chemistry, London, 1989); A. H. Haines Methods for the Oxidation of Organic Compounds (Academic Press, London, 1988) and B. J. Wakefield Organolithium Methods (Academic Press, London, 1988). Some important Lit ref are Kim S et al, Synthesis, 2006, 5, 753-755.

EXAMPLES

The following Examples describe the preparation of compounds according to the invention and are intended to illustrate the invention. The Examples are not be construed as limiting in any way the scope of the present invention. Proton NMR spectra were recorded at 300 MHz on a Bruker EM 300 spectrometer in CDCl3 unless otherwise stated. Chemical shifts for proton NMR are ppm downfield from tetramethylsilane.

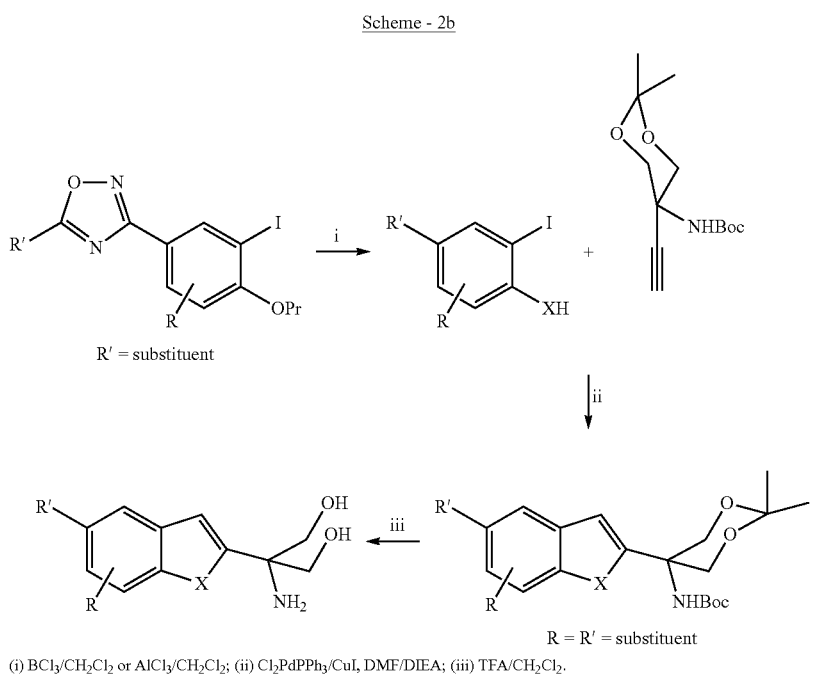

Scheme - 2b

R' = substituent

R = R' = substituent
(i) BCl₃/CH₂Cl₂ or AlCl₃/CH₂Cl₂; (ii) Cl₂PdPPh₃/CuI, DMF/DIEA; (iii) TFA/CH₂Cl₂.

The other compounds of invention including intermediates were prepared by using various known synthesis methods like reductive amination etc. The compound preparations illustrated can be carried out by generally known methods as exemplified hereinafter. The starting materials and intermediates used in the synthesis of compounds of this invention are generally commercially available or may be prepared by conventional methods of organic chemistry. Suitable methods for

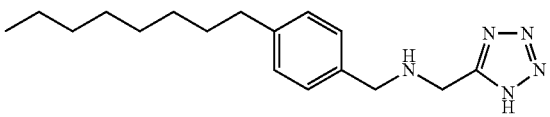

65
-continued
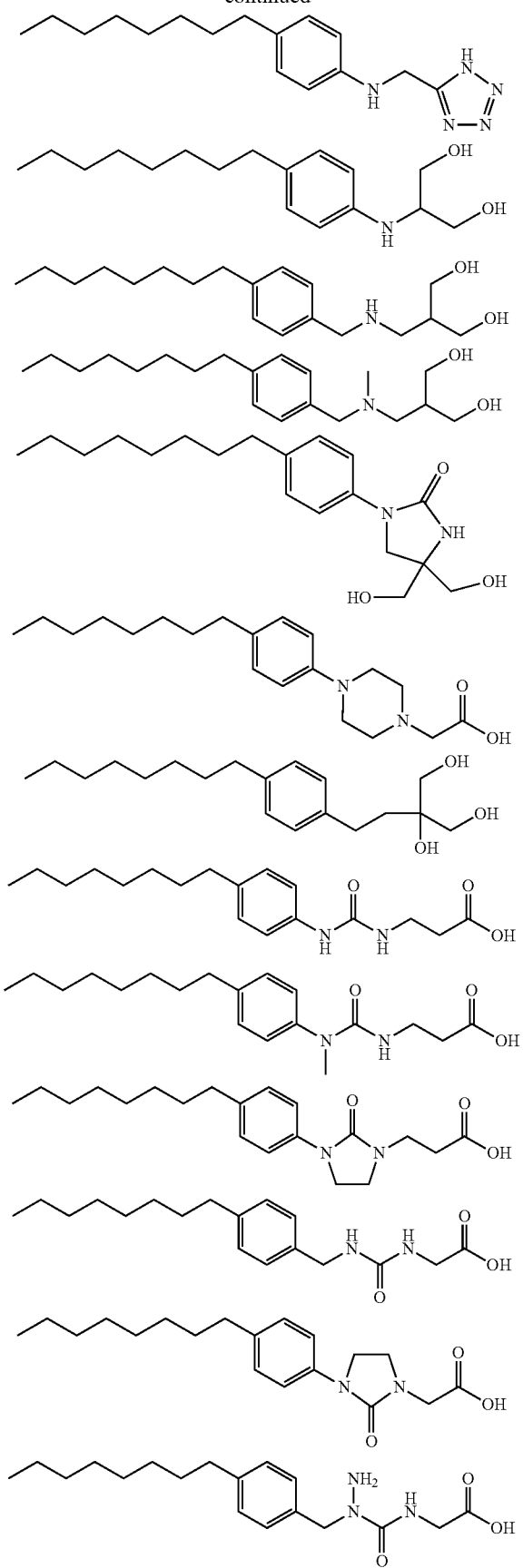
66
-continued
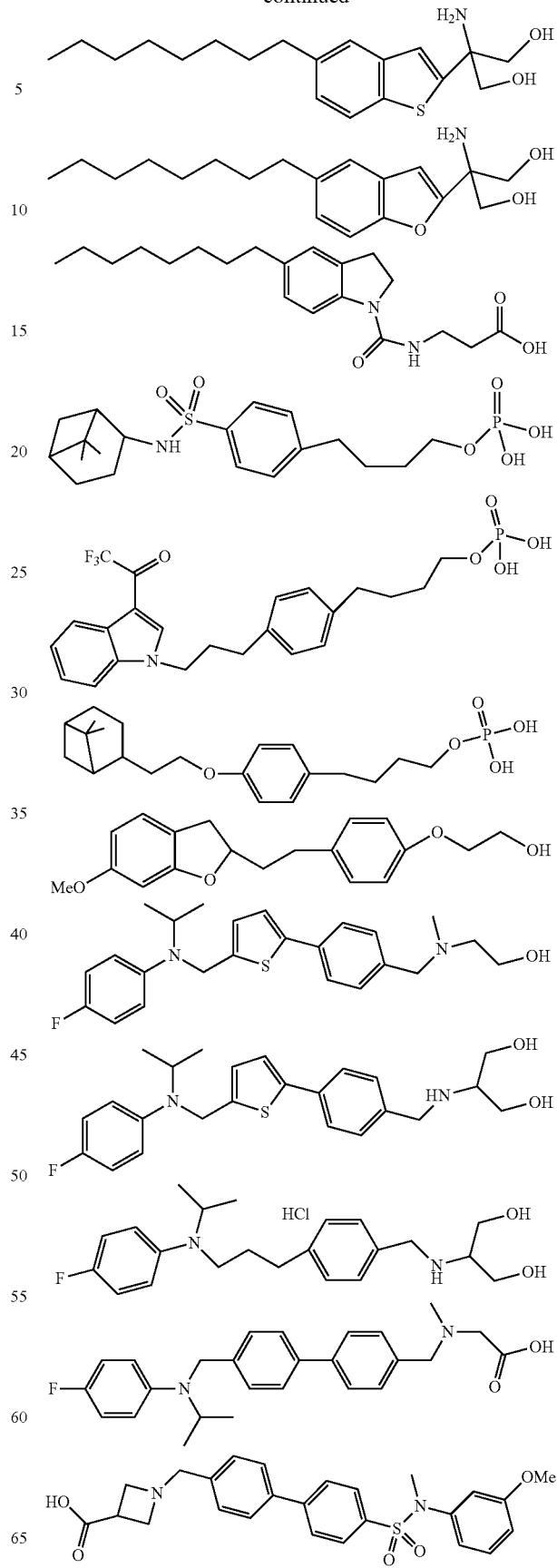

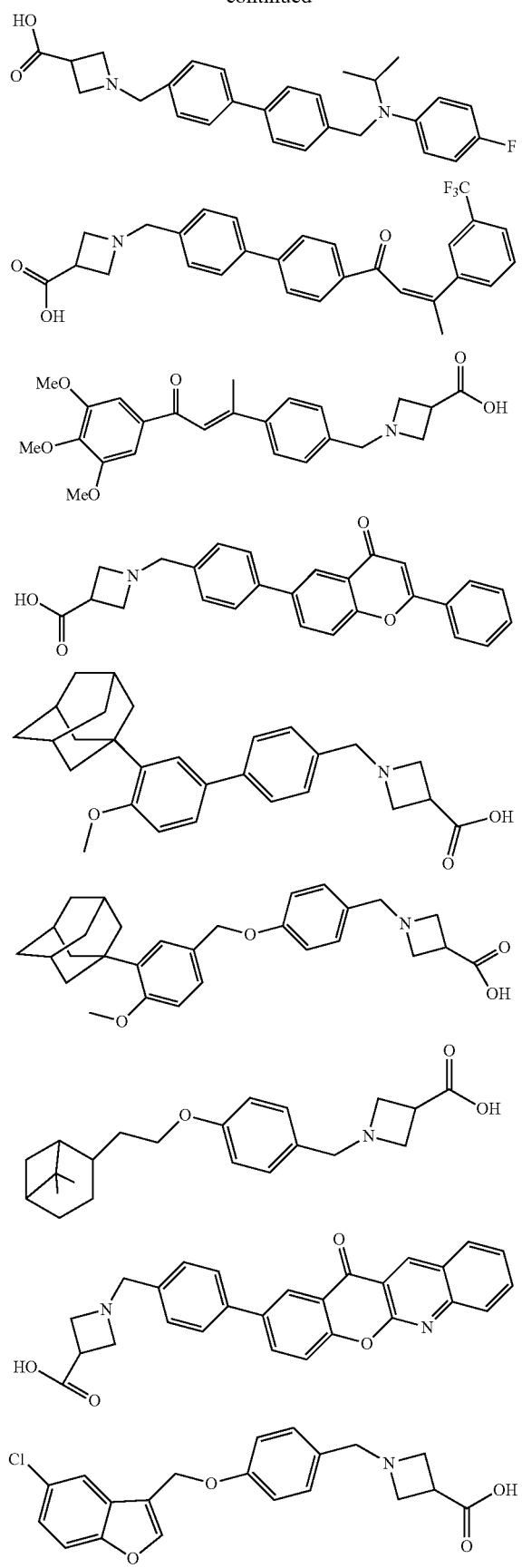
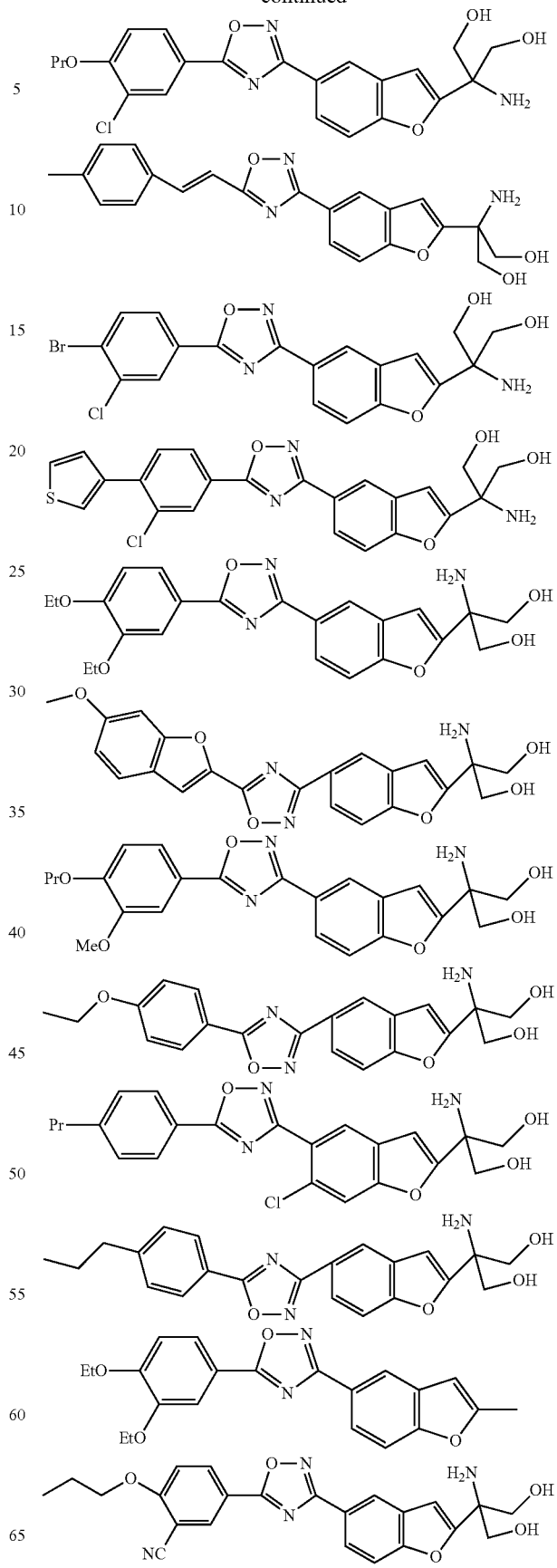

-continued

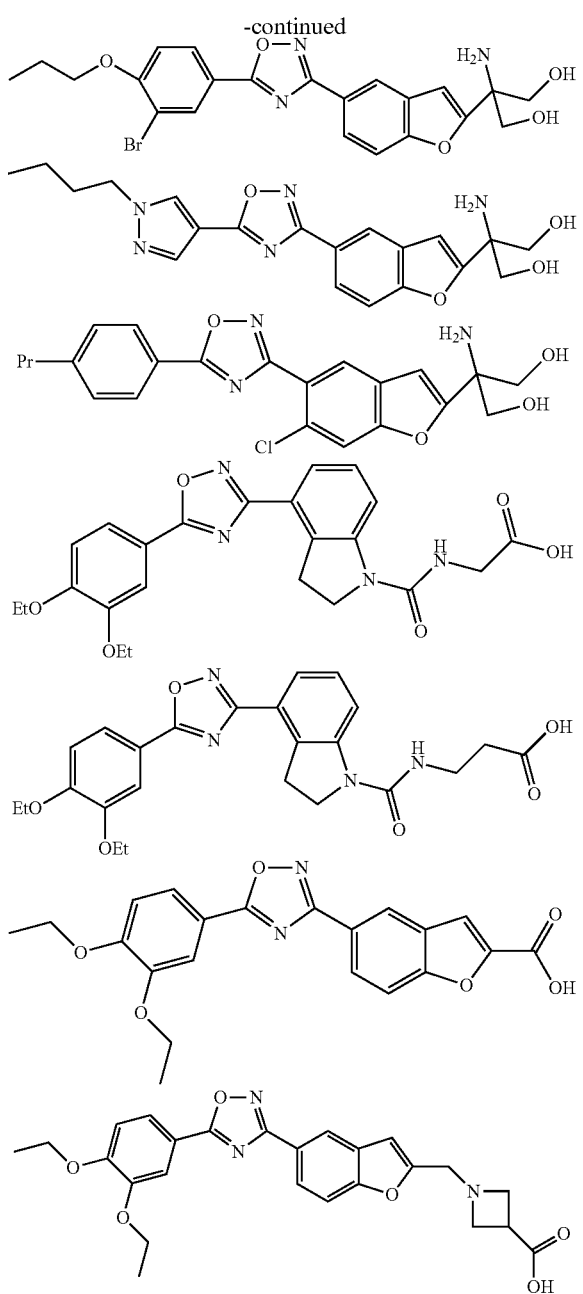

Example 1

5-(5-(3,4-Diethoxyphenyl)-1,2,4-oxadiazol-3-yl)benzofuran-2-carboxylic acid

Step A: Step A: 4-Hydroxy-3-iodobenzonitrile: To a solution of 4-hydroxybenzonitrile (0.5 g; 4.18 mmol) in 25% $NH_4OH$ (22 ml) a solution of $I_2$ (1.06 g; 4.18 mmol) and KI (3.41 g; 20.54 mmol) in $H_2O$ (5 ml) was added at once with stirring. The stirring was continued for 6 h, during which time the mixture turn from black into colourless. The precipitate formed was filtered off and filtrate was evaporated to dryness under reduced pressure. The residue was treated with $H_2O$ (3 ml). The precipitate formed was filtered off, washed with cold $H_2O$ (3×2 ml), and dried in vacuo to give the title compound (0.82 g; 80%), as colourless solid. $^1$H-NMR ($CDCl_3$) 7.96 (d, 1H, 1.9 Hz); 7.53 (dd, 1H, J=1.9 Hz, 8.5 Hz); 7.03 (d, 1H, J=8.5 Hz); 6.03 (s, 1H);

Step B: 2-(Hydroxymethyl)benzofuran-5-carbonitrile: Propargyl alcohol (0.24 ml; 5.2 mmol) was added drop wise during 30 min to a refluxed suspension of the product of Step A (0.48 g; 1.96 mmol) and $Cu_2O$ (0.28 g; 1.96 mmol) in anhydrous pyridine (4 ml) with stirring under $N_2$. After additional reflux for 15 min, the mixture was cooled to room temperature, diluted to 20 ml with ethyl acetate (EtOAc) and insoluble material was removed by filtration. The filtrate was evaporated to dryness under reduced pressure and the residue was diluted to 20 ml with EtOAc, washed with diluted HCl (10 ml). The insoluble material formed was filtered off and the organic phase was washed with $H_2O$ (5 ml), brine, dried over anhydrous $MgSO_4$, filtered and the filtrate evaporated to dryness. The residue was purified by flash column chromatography (FCC) ($SiO_2$, $CH_2Cl_2$ and EtOAc, 9:1) to give the title compound (0.23 g; 67%) as a colourless solid. $^1$H-NMR ($CDCl_3$) 7.86 (m, 1H); 7.49-7.55 (m, 2H); 6.72 (d, 1H, J=3 Hz); 4.8 (d, 2H, J=3 Hz); 2.18 (broad s, 1H);

Step C: N-Hydroxy-2-(hydroxymethyl)benzofuran-5-carboximidamide: A mixture of the product of Step B (0.22 g; 1.27 mmol) and HCl×$NH_2OH$ (0.18 g; 2.59 mmol) and N,N-diisopropylethylamine (DIPEA) (0.67 ml; 3.82 mmol) in ethanol (EtOH) (2 ml) was stirred for 3 h at ~71° C. The solvents were removed in vacuo and the residue was treated with $H_2O$ (3 ml) and the product was taken up by EtOAc (3×15 ml). The combined organic phase was washed with brine, dried over anhydrous MgSO4, filtered and filtrate evaporated to dryness to give the title compound (0.2 g; 76%), as colourless solid, which was used in the next step without further purification.

Step D: (5-(5-(3,4-Diethoxyphenyl)-1,2,4-oxadiazol-3-yl)benzofuran-2-yl)ethanol: A mixture of 3,4-diethoxybenzoic acid (0.21 g; 1 mmol), the product of Step C (0.2 g; 0.97 mmol) and hydrochloride salt of 1-ethyl-3-(3-dimethylaminopropyl) carbodiimide (EDC) (0.22 g; 1.15 mmol) in anhydrous dimethylsulfoxide (DMSO) (2 ml) was stirred for 20 min at ~40° C. under $N_2$. To it 1M tetra-n-butylammonium fluoride (TBAF) in terahydrofuran (THF) (0.4 ml) was added and the resulting mixture was stirred for 1 h at ~120° C., then overnight at room temperature. The solvents were removed in vacuo and the residue was partitioned between EtOAc (15 ml) and $H_2O$ (5 ml). The organic phase was washed with brine, dried over anhydrous $MgSO_4$ and filtered. The filtrate was evaporated to dryness under reduced pressure and the residue was purified by FCC ($SiO_2$; $CH_2Cl_2$) to give the title compound (0.13 g; 34%), as greyish solid. $^1$H-NMR ($CDCl_3$) 8.36 (d, 1H, J=3 Hz); 8.09 (dd, 1H, J=3, 9 Hz); 7.79 (dd, 1H, J=3, 9 Hz); 7.68 (d, 1H, J=3 Hz); 7.55 (d, 1H, J=9 Hz); 6.98 (d, 1H, J=9 Hz); 6.73 (s, 1H); 4.8 (s, 2H); 4.2 (m, 4H); 2.02 (s, 1H); 1.51 (m, 6H);

Step E: 5-(5-(3,4-Diethoxyphenyl)-1,2,4-oxadiazol-3-yl)benzofuran-2-carbaldehyde: A suspension of the product of Step D (0.13 g; 0.34 mmol) and $MnO_2$ (0.15 g; 1.7 mmol) in dioxane (4 ml) was refluxed for 1 h with stirring. After cooling to room temperature, the insoluble material was removed by filtration, washed with EtOAc (20 ml) and combined filtrates were evaporated to dryness to give the title compound (0.13 g; 100%), as greyish solid. $^1$H-NMR ($CDCl_3$) 9.91 (s, 1H); 8.59 (s, 1H); 8.33 (dd, 1H, J=2, 9 Hz); 7.63-7.82 (m, 4H); 6.99 (d, 1H, J=9 Hz); 4.14-4.26 (m, 4H); 1.4-1.57 (m, 6H+$H_2O$).

Step F: 5-(5-(3,4-Diethoxyphenyl)-1,2,4-oxadiazol-3-yl)benzofuran-2-carboxylic acid; To a suspension of the product of Step E (0.009 g; 0.024 mmol) and $AgNO_3$ (0.06 g; 0.14 mmol) in EtOH (0.2 ml) $H_2O$ (0.1 ml) was added at room temperature, followed by 10% KOH (0.1 ml). The resulting black suspension was stirred for 1 h at ~50° C. and cooled to room temperature and filtered. The insoluble material was washed with $H_2O$ (2×0.2 ml). The combined filtrates were acidified to pH=1 with HCl and the product was taken up by extraction with EtOAc (2×5 ml). The organic phase was washed with brine, dried over anhydrous $MgSO_4$, filtered and filtrate evaporated to dryness. The residue was purified by FCC ($SiO_2$, $CH_2Cl_2$/acetic acid (AcOH) 98/2) to give the title compound (0.00012 g; 12.8%), as a creamy solid. $^1$H-NMR ($CDCl_3$+$CD_3OD$) 8.48 (s, 1H); 8.22 (m, 1H); 7.77 (m, 1H); 7.64-7.66 (m, 2H); 7.58 (s, 1H); 6.96 (d, 1H, J=6 Hz); 4.19 (m, 4H); 1.4-1.54 (m, 6H).

Example 2

1-((5-(5-(3,4-Diethoxyphenyl)-1,2,4-oxadiazol-3-yl)benzofuran-2-yl)methyl)azetidine-3-carboxylic acid Step A: Methyl 1-((5-(5-(3,4-diethoxyphenyl)-1,2,4-oxadiazol-3-yl)benzo furan-2-yl)methyl)azetidine-3-carboxylate: A mixture the product of Example 1, Step E (0.07 g; 0.85 mmol), azetidine-3-methylcarboxylate hydrochloride (0.03 g; 0.199 mmol) and DIPEA (0.035 ml, 0.2 mmol) in 1,2-dichloroethane (1 ml) and methanol (MeOH) (3 ml) was sonicated for 30 min at room temperature, then evaporated to dryness. The yellowish residue was suspended in 1,2-dichloroethane (1 ml) and $NaBH(OAc)_3$ (0.12 g; 0.57 mmol) was added, followed by AcOH (0.01 ml). This was stirred for 1 h at room temperature and diluted to 15 ml with EtOAc, washed with 10% KOH (2×3 ml); brine, dried over anhydrous $MgSO_4$, filtered and the filtrate evaporated to dryness. The residue was purified by FCC ($SiO_2$, EtOAc) to give the title compound (0.06 g; 68%), as creamy syrup. $^1$H-NMR ($CDCl_3$) 8.33 (d, 1H, J=3 Hz); 8.06 (dd, 1H, 3, 9 Hz); 7.78 (dd, 1H, J=3, 9 Hz); 6.87 (d, 1H, J=2 Hz); 6.63 (s, 1H); 4.14-4.22 (m, 4H); 3.6-3.7 (m, 5H); 3.48-3.34 (m, 2H); 1.49 (m, 6H).

Step B: 1-((5-(5-(3,4-Diethoxyphenyl)-1,2,4-oxadiazol-3-yl)benzofuran-2-yl)methyl)azetidine-3-carboxylic acid: A mixture of the product of Step A (0.06 g; 0.126 mmol) and 10% KOH (0.1 ml) in dioxane (2 ml) was refluxed for 1 h and solvents were evaporated to dryness. The residue was treated with AcOH (0.5 ml) and evaporated to dryness in vacuo. The residue was purified by FCC ($SiO_2$, $CH_2Cl_2$ saturated with concentrated $NH_4OH$ and MeOH, 85:15) to give the title compound (0.032 g; 55%), as a colourless solid. $^1$H-NMR ($CD_3OD$+$CDCl_3$) 8.37 (d, 1H, J=3 Hz); 8.09 (dd, 1H, J=3, 6 Hz); 7.77 (dd, 1H, J=3, 9 Hz); 7.68 (s, 1H); 7.6 (d, 1H, J=9 Hz); 7.02-7.07 (m, 2H); 4.38 (s, 2H); 4.05-4.21 (m, 8H); 1.44-1.49 9m, 6H).

Example 3

N-(1H-Tetrazol-5-yl)methyl-4-octylbenzylamine

Step A: 4-n-Octylbenzaldehyde: A mixture of n-octylbenzene (1.2 g; 6.3 mmol) hexamethylenetetramine (0.97 g; 6.93 mmol) in trifluoroacetic acid (TFA) was refluxed for 4 h, cooled to room temperature and evaporated to dryness under reduced pressure. The residue was neutralized with 5% $NaHCO_3$ and extracted with diethyl ether ($Et_2O$) (3×5 ml). The combined organic phase was washed with $H_2O$, brine, dried over anhydrous $MgSO_4$ and filtered. The filtrate was evaporated under reduced pressure and the residue was purified by FCC ($SiO_2$, hexane) to give the title compound (0.4 g; 29%) as a colourless oil and starting n-octylbenzene (0.8 g; 67%). $^1$H-NMR ($CDCl_3$) 9.96 (s, 1H); 7.77 (d, 2H, J=8.1 Hz); 7.31 (d, 2H, J=8.1 Hz); 2.67 (t, 2H, J=7.9 Hz); 1.6 (m, 2H); 1.26 (m, 10H); 0.86 (t, 3H, J=6.9 Hz);

Step B: 2-(4-Octylbenzylamino)acetonitrile: T a suspension of the product of Step A (0.17 g; 0.78 mmol) and aminoacetonitrile bisulphate (0.18 g; 1.17 mmol) and $NaBH(OAc)_3$ in 1,2 dichloroethane (3 ml), DIPEA (0.2 ml; 1.17 mmol) was added at room temperature followed by AcOH (0.045 ml; 0.78 mmol). The resulting mixture was stirred over a weekend at room temperature under $N_2$ and quenched by an addition of 1M NaOH (0.5 ml). This was diluted to 15 ml with $Et_2O$, washed with $H_2O$, brine, dried over anhydrous $MgSO_4$ and filtered. The filtrate was evaporated to dryness under reduced pressure and the residue was diluted to 3 ml with anhydrous MeOH and to it $NaBH_4$ (0.1 g; 2.6 mmol) was added portion wise at room temperature with stirring. After stirring overnight, the mixture was evaporated to dryness and the residue was diluted to 15 ml with $Et_2O$, washed with 1N NaOH, $H_2O$, brine, dried over anhydrous $MgSO_4$ and filtered. The filtrate was evaporated under reduced pressure and the residue was purified by FCC ($SiO_2$, hexane/EtOAc 6:4) to give the title compound (0.07 g; 28%) as a colourless syrup. $^1$H-NMR ($CDCl_3$) 7.23 (d, 2H, J=8.01 Hz); 7.14 (d, 2H, J=8.01 Hz); 3.88 (s, 2H); 3.55 (s, 2H); 2.58 (t, 2H, J=7.94 Hz); 1.6 (m, 3H); 1.27 (m, 10H); 0.86 (t, 3H, J=6.93 Hz).

Step C: N-(1H-Tetrazol-5-yl)methyl-4-n-octylbenzylamine: A mixture of the product of Step B (0.07 g; 0.271 mmol) and $Me_3SiN_3$ (0.36 ml; 2.71 mmol) and 1M TBAF in THF (0.27 ml; 0.271 mmol) was stirred at 75±5° C. for 8 h in sealed flask. After cooling to room temperature, the mixture was diluted to 1 ml with MeOH, refluxed for 30 min under $N_2$ and left overnight in refrigerator. The precipitate formed was filtered off, washed with $Et_2O$ and dried to give a title compound (0.069 g; 84%) as colourless solid. $^1$H-NMR ($CD_3OD$) 7.32 (d, 2H, J=8.0 Hz); 7.21 (d, 2H, J=8.0 Hz); 4.72 (s, $CD_3OH$); 4.34 (s, 2H); 4.16 (s, 2H); 2.59 (t, 2H, J=7.76 Hz); 1.57 (t, 2H, J=7.19 Hz); 1.25 (m, 10H); 0.84 (t, 3H, J=6.93 Hz);

Example 4

N-((1H-Tetrazol-5-yl)methyl)-4-n-octylaniline

Step A: 2-(4-Octylphenylamino)acetonitrile: A mixture of 4-n-octylaniline (0.21 g; 1 mmol), $BrCH_2CN$ (0.156 mmol; 1.3 mmol) and $K_2CO_3$ (0.28 g; 2 mmol) in anhydrous $CH_3CN$ (3 ml) was stirred overnight at ~60° C. under $N_2$, then concentrated under reduced pressure. The residue was partitioned between $CH_2Cl_2$ (20 ml) and $H_2O$ (10 ml). The organic phase was dried over anhydrous $MgSO_4$ and filtered. The filtrate was evaporated to dryness under reduced pressure and the residue was purified by crystallization from hexane to give the title compound (0.18 g; 74%) as creamy solid. $^1$H-NMR ($CDCl_3$) 7.06 (d, 2H, J=8.48 Hz); 6.63 (d, 2H, J=8.48 Hz); 4.06 (d, 2H, J=5.75 Hz); 3.83 (broad m, 1H); 2.51 (t, 2H, J=7.92 Hz); 1.55 (m, 3H); 1.27 (m, 10H); 0.86 (t, 3H, J=6.87 Hz).

Step B: N-((1H-Tetrazol-5-yl)methyl)-4-n-octylaniline: When the product of Step A was substituted for 2-(4-octylbenzylamino)acetonitrile in Example 3, Step C, the identical process afforded the title compound in 77% yield, as creamy solid. $^1$H-NMR ($CDCl_3$) 6.94 (d, 2H, J=8.37 Hz); 6.61 (broad s, 2H); 6.49 (d, 2H, J=8.37 Hz); 4.68 (m, 2H); 2.44 (t, 2H, J=7.94 Hz); 1.49 (t, 2H, J=7.55 Hz); 1.24 (m, 10H); 0.85 (t, 3H, J=6.95 Hz).

Example 5

2-(4-Octylphenylamino)propane-1,3-diol

Step A: 2,2-Dimethyl-N-(4-octylphenyl)-1,3-dioxan-5-amine: To a mixture of 4-n-octylaniline (0.205 g; 1 mmol) and 2,2-dimethyl-1,3-dioxan-5-one (Helvetica Chimica Acta, 2003, 86, 2467; 0.13 g; 1 mmol) and NaBH(OAc)$_3$ in 1,2 dichloroethane (3.5 ml), AcOH (0.06 ml; 1 mmol) was added and the mixture was stirred for 2 h at room temperature under N$_2$, diluted to 20 ml with Et$_2$O and washed with 1N NaOH, H$_2$O, brine, dried over anhydrous MgSO$_4$ and filtered. The filtrate was evaporated under reduced pressure and the residue was purified crystallization from hexane to give the title compound (0.2 g; 63%) as a colourless solid. $^1$H-NMR (CDCl$_3$) 6.97 (d, 2H, J=8.4 Hz); 6.54 (d, 2H, J=8.4 Hz); 4.1 (dd, broad s, 3H, J=4.2, 11.9 Hz); 3.74 (dd, 2H, J=4.2, 11.9 Hz); 3.4 (m, 1H); 2.47 (t, 2H, J=7.91 Hz); 1.55 (m, 2H+H$_2$O); 1.46 (s, 3H); 1.43 (s, 3H); 1.25 (m, 10H); 0.86 (m, 3H).

Step B: 2-(4-octylphenylamino)propane-1,3-diol: To a solution of the product of Step A (0.1 g; 0.31 mmol) in MeOH (1 ml) Me$_3$SiCl (0.5 ml) was added at room temperature. After stirring for 1 h, the mixture was evaporated to dryness under reduced pressure to give a hydrochloride salt of the title compound (0.1 g; 100%) as a colourless solid. $^1$H-NMR (CDCl$_3$) 10.66 (bs, 2H); 7.53 (d, 2H, J=7.98 Hz); 7.18 (d, 2H, J=7.98 Hz); 4.82 (broad s, 2H); 3.98 (broad m, 4H); 3.51 (broad m, 1H); 2.58 (t, 2H, J=7.68 Hz); 1.56 (m, 2H); 1.43 (s, 3H); 1.27 (m, 10H); 0.86 (t, 3H, J=6.96 Hz).

Example 6

2-((4-n-Octylbenzylamino)methyl)propane-1,3-diol

Step A: 4-n-Octylbenzyl alcohol: NaBH$_4$ (0.04 g; 1.06 mmol) was added portion wise to a solution of the product of Example 3, Step A in MeOH (5 ml) at room temperature, with vigorous stirring. After 30 min of stirring, the mixture was evaporated to dryness, diluted to 10 ml with Et$_2$O and washed with 1N NaOH, H$_2$O, brine, dried over anhydrous MgSO$_4$ and filtered. The filtrate was evaporated under reduced pressure to give the title compound (0.082 g; 100%), as colourless syrup, which was used in next step without further purification. $^1$H-NMR (CDCl$_3$) 7.26 (d, 2H, J=8 Hz); 7.15 (d, 2H, J=8 Hz); 4.64 (s, 2H); 2.58 (t, 2H, J=7.9 Hz); 1.56 (m, 3H); 1.26 (m, 10H); 0.86 (t, 3H, J=6.9 Hz).

Step B: 4-n-octylbenzyl bromide: PBr$_3$ (0.23 ml) was added drop wise to a stirred solution of the product of Step A (0.082 g; 0.37 mmol) in Et$_2$O (2 ml) at −15° C. The mixture was allowed to warm up to room temperature and the stirring was continued for 4 h. This was poured onto ice (5 g) and the product was extracted with fresh Et$_2$O (2×10 ml). The combined extracts were washed with 5% NaHCO$_3$, H$_2$O, brine, dried over anhydrous MgSO$_4$ and filtered. The filtrate was evaporated under reduced pressure and the residue was purified by FCC (SiO$_2$, hexane) to give the title compound (0.04 g; 40%) as a colourless solid. $^1$H-NMR (CDCl$_3$) 7.28 (d, 2H, J=8 Hz); 7.13 (d, 2H, J=8 Hz); 4.48 (s, 2H); 2.57 (t, 2H, J=7.9 Hz); 1.57 (m, 2H); 1.26 (m, 10H); 0.86 (t, 3H, J=7 Hz).

Step C: 4-n-Octylbenzylamine: To a solution of the product of Step B (0.13 g; 0.459 mmol) in anhydrous hexamethylenedisilazane (HMDSA) 1M NaHMDSA in THF was added at room temperature under N$_2$ with stirring. After stirring overnight at room temperature solvents were removed under reduced pressure and the residue was diluted to 5 ml with MeOH and 1 drop of concentrated HCl was added. This was evaporated under reduced pressure, diluted to 15 ml with Et$_2$O and washed with 1N NaOH, brine, dried over anhydrous MgSO$_4$ and filtered. The filtrate was evaporated under reduced pressure to give the title compound (0.1 g; 100%), as colourless oil, which was used in the next step without further purification. $^1$H-NMR (CDCl$_3$) 7.2 (d, 2H, J=8 Hz); 7.13 (d, 2H, J=8 Hz); 3.82 (s, 2H); 2.57 (t, 2H, J=7.9 Hz); 1.58 (m, 2H); 1.41 (s, 2H); 1.26 (m, 10H); 0.86 (t, 3H, J=7 Hz).

Step D: (2,2-Dimethyl-1,3-dioxan-5-yl)-N-(4-octylbenzyl)methylamine: When the product of Step C was substituted for 4-n-octylaniline in Example 5, Step A, the identical process afforded the title compound in 86% yield, as a colourless syrup. $^1$H-NMR (CDCl$_3$) 7.23 (d, 2H, J=8 Hz); 7.11 (d, 2H, J=8 Hz); 3.96 (dd, 2H, J=5.57, 11.73 Hz); 11.73 Hz); 3.83 (s, 2H); 3.75 (dd, 2H, J=5.57, 2.69 (m, 1H); 2.56 (t, 2H, J=7.88 Hz); 1.81 (broad s, 1H+H$_2$O); 1.4 (m, 5H); 1.25 (m, 13H); 0.86 (t, 3H, J=6.96 Hz).

Step E: 2-((4-n-Octylbenzylamino)methyl)propane-1,3-diol: A solution of the product of Step D (0.6 g; 0.13 mmol) in 60% trifluoroacetic acid (TFA) in CH$_2$Cl$_2$ (2 ml) was stirred for 15 min at room temperature and the mixture was diluted to 5 ml with MeOH and evaporated to dryness under reduced pressure. The residue was dissolved in iso-propanol (iPrOH) (2 ml) and one drop of concentrated HCl was added. This was evaporated under reduced pressure and treated with anhydrous Et$_2$O. The precipitate formed was filtered off, dried in vacuo for 1 h to give a hydrochloride salt of the title compound (0.04 g; 85%), as a colourless solid. $^1$H-NMR (D$_2$O) 7.32 (d, 2H, J=7.56 Hz); 7.21 (d, 2H, J=7.56 Hz); 4.2 (s, 2H); 4.66 (DHO); 3.69 (s, 4H); 3.36 (s, 2H); 2.52 (t, 2H, J=7.47 Hz); 1.49 (5, 2H); 1.16 (m, 10H); 0.74 (m, 3H).

Example 7

2-((Methyl(4-octylbenzyl)amino)methyl)propane-1,3-diol

Step A: (2,2-dimethyl-1,3-dioxan-5-yl)-N-methyl-N-(4-octylbenzyl)methyl amine: When the product of Example 6, Step D is substituted for 4-n-octylaniline and 30% aqueous HCHO is substituted for 2,2-dimethyl-1,3-dioxan-5-one in Example 3, Step A, the identical process afforded the title compound in 100% yield, as a colourless syrup. $^1$H-NMR (CDCl$_3$) 7.2 (d, 2H, J=7.75 Hz); 7.11 (d, 2H, J=7.75 Hz); 3.83 (s, 2H); 3.94 (m, 4H); 3.64 (s, 2H); 2.83 (m, 1H); 2.56 (d, 2H, J=7.3 Hz); 2.29 (s, 3H); 1.58 (m, 2H+H$_2$O); 1.25-1.42 (m, 18H); 0.86 (m, 3H).

Step B: 2-((Methyl(4-octylbenzyl)amino)methyl)propane-1,3-diol: When the product of Step A is substituted for (2,2-dimethyl-1,3-dioxan-5-yl)-N-(4-octylbenzyl)methylamine in Example 6, Step E, the identical process afforded the title compound in 79% yield, as a glassy solid. $^1$H-NMR (D$_2$O) 7.3 (d, 2H, J=7.8 Hz); 6.96 (d, 2H, J=7.8 Hz); 4.66 (DHO); 4.24 (s, 2H); 3.73 (m, 4H); 3.32 (m, 1H); 2.7 (s, 3H); 2.3 (t, 2H, J=7.63 Hz); 1.36 (m, 2H); 1.15 (s, 2H); 1.15 (m, 10H); 0.73 (t, 3H, J=6.73 Hz).

Example 8

4,4-Bis(hydroxymethyl)-1-(4-octylphenyl)imidazolidin-2-one

Step A: tert-Butyl 2,2-dimethyl-5-((4-octylphenylamino)methyl)-1,3-dioxan-5-ylcarbamate: To a mixture of 4-n-octylaniline (0.21 g; 1 mmol), tert-butyl 5-formyl-2,2-dimethyl-1,3-dioxan-5-ylcarbamate (Ooii et al, J. Org. Chem., 2004, 69, 7765; 0.26 g; 1 mmol) and NaBH(OAc)$_3$ (0.3 g; 1.4 mmol) in 1,2-dichloroethane (3.5 ml) AcOH (0.06 ml; 1 mmol) was added at room temperature with stirring under $N_2$. After stirring for 2 h, the mixture was diluted to 20 ml with $Et_2O$, washed with 1.M NaOH (2×5 ml), brine and dried over anhydrous $MgSO_4$ and filtered. The filtrate was evaporated to dryness under reduced pressure. The residue was dissolved in hexane (5 ml) and kept in the freezer (−18° C.) overnight. The crystals formed were filtered off, washed with small volume of hexane and dried to give the title compound (0.32 g; 71%), as colourless crystals. $^1$H-NMR (CDCl$_3$) 6.96 (d, 2H, J=8.4 Hz); 6.58 (d, 2H, J=8.4 Hz); 4.84 (broad s, 1H); 4.01 (d, 2H, J=11.9); 3.85 (broad s, 1H); 3.8 (d, 2H, J=11.9 Hz); 3.44 (s, 2H); 2.46 (t, 2H, J=7.9 Hz); 1.5 (m, 2H); 1.45 (s, 3H); 1.43 (s, 9H); 1.42 (s, 3H); 1.26 (m, 10H); 0.86 (t, 2H, J=6.95 Hz).

Step B: 4,4-(2,2-Dimethyl-1,3-dioxanyl)-1-(4-octylphenyl)imidazolidin-2-one: A solution of the product of Step A (0.17 g; 0.38 mmol) and 60% NaH in mineral oil (0.043 g; 1.14 mmol) in anhydrous DMF (4 ml) was stirred overnight at ~55° C. under $N_2$. After removal of solvent in vacuo, the residue was diluted to 15 ml with $Et_2O$, washed with 10% citric acid, $H_2O$, brine, dried over anhydrous $MgSO_4$ and filtered. The filtrate was evaporated under reduced pressure and the residue was purified by FCC (SiO$_2$, hexane/EtOAc 8:2) to give the title compound (0.06 g; 42%) as a colourless solid and starting material (0.1 g; 58%). $^1$H-NMR (CDCl$_3$) 7.41 (d, 2H, J=8.58 Hz); 7.12 (d, 2H, J=8.58 Hz); 5.27 (broad s, 1H); 3.84 (d, 2H, J=11.3 Hz); 3.78 (d, 2H, J=11.3 Hz); 3.68 (s, 2H); 2.55 (t, 2H, J=7.83 Hz); 1.56 (m, 2H); 1.28 (m, 10H); 0.84 (t, 3H, J=6.76 Hz).

Step C: 4,4-Bis(hydroxymethyl)-1-(4-octylphenyl)imidazolidin-2-one: When the product of Step B is substituted for (2,2-dimethyl-1,3-dioxan-5-yl)-N-(4-octylbenzyl)methylamine in Example 6, Step E, the identical process afforded the title compound in 74% yield, as a colourless solid, after purification by FCC (SiO$_2$, CH$_2$Cl$_2$ saturated with concentrated NH$_4$OH/MeOH; 98:2). $^1$H-NMR (CDCl$_3$) 7.30 (d, 2H, J=8.49 Hz); 7.02 (d, 2H, J=8.49 Hz); 6.53 (s, 1H); 4.65 (broad s, 2H); 3.48-3.62 (m, 6H); 2.47 (t, 2H, J=7.94 Hz); 1.51 (m, 2H); 1.25 (m, 10H); 0.87 (t, 3H, J=6.94 Hz).

Example 9

2-(4-(4-n-Octylphenyl)piperazin-1-yl)acetic acid

Step A: 4-n-Octyliodobenzene: To a suspension of n-octylbenzene (1 g; 5.2 mmol) and CF$_3$SO$_3$Ag (1.35 g; 5.2 mmol) in anhydrous CH$_2$Cl$_2$ (15 ml) I$_2$ was added at 0° C. The resulting mixture was allowed to warm up to room temperature and stirred for additional 1 h, then filtered through a pad of Celite, washed with fresh CH$_2$Cl$_2$ (2×15 ml) and combined filtrates washed with 5% Na$_2$SO$_3$, H$_2$O, brine, dried over anhydrous MgSO$_4$ and filtered. The filtrate was evaporated under reduced pressure to give the title product and 2-iodo isomer (1.64 g; 100%), as creamy oil, which was used in the next step without further purification. $^1$H-NMR (CDCl$_3$) 7.7-7.8 (m, 0.3H); 7.56 (d, 1.7H, J=8.3 Hz); 7.29-7.16 (m, 0.6H); 6.9 (d, 1.4H, J=8.3 Hz); 6.85-6.82 (m, 0.3H); 2.68 (t, 0.6, J=8.01 Hz); 2.52 (t, 1.4H, J=7.89 Hz); 1.56 (m, 2H); 1.25 (m, 10H); 0.86 (m, 3H).

Step B: tert-Butyl 4-(benzoyloxy)piperazine-1-carboxylate: To a suspension of benzoyl peroxide+15% H$_2$O (1.47 g; 4.55 mmol) and K$_2$HPO$_4$ (1.19 g; 6.8 mmol) in DMF (11.36 ml) N-BOC piperazine (Sengmany et al, Tetrahedron, 2007, 63, 3672; 1 g; 5.4 mmol) was added and the mixture was stirred for 1 h at room temperature. To it, H$_2$O (20 ml) was added and the resulting mixture was vigorously stirred until homogenous. This was extracted with EtOAc (15 ml). The organic phase was washed with H$_2$O and combined aqueous phase was extracted with fresh EtOAc (3×10 ml). The combined organic phase was washed with H$_2$O, brine, dried over anhydrous MgSO$_4$ and filtered. The filtrate was evaporated under reduced pressure to give the title product (0.9 g; 65%), as a colourless solid. $^1$H-NMR (CDCl$_3$) 8-7.96 (m, 2H); 7.59-7.53 (m, 1H); 7.45-7.38 (m, 2H); 4.01 (m, 2H); 3.41-3.2 (m, 4H); 2.9 (m, 2H); 1.46 (s, 9H).

Step C: tert-Butyl 4-(4-octylphenyl)piperazine-1-carboxylate: To a solution of the product of Step A (0.32 g; 1.01 mmol) in anhydrous THF (2 ml) 2 M iPrMgCl in THF (0.56 ml; 1.11 mmol) was added at −15° C. under N$_2$, followed 1.27 M solution of anhydrous ZnCl$_2$ in THF (0.41 ml; 0.52 mmol), after stirring for 1 h at 0° C. The resulting mixture was stirred for 30 min on ice-bath under N$_2$ and the solution of the product of Step B (0.16 g; 0.51 mmol) and CuCl$_2$ (2.5 mol %) in anhydrous THF (10 ml) was added. The resulting mixture was allowed to warm up to room temperature and stirred for additional 10 min. This was diluted to 20 ml with Et$_2$O and washed with 5% NaHCO$_3$, H$_2$O, brine, dried over anhydrous MgSO$_4$ and filtered. The filtrate was evaporated under reduced pressure and the residue was purified by FCC (SiO$_2$, hexane/EtOAc 9:1) to give the title compound (0.06 g; 31%), as a creamy syrup. $^1$H-NMR (CDCl$_3$) 7.07 (d, 2H, J=8.6 Hz); 6.84 (d, 2H, J=8.6 Hz); 3.55 (t, 4H, J=5 Hz); 3.06 (t, 4H, J=5 Hz); 2.51 (t, 2H, J=7.94 Hz); 1.55-1.38 (m, 11H); 1.26 (m, 10H); 0.86 (t, 3H, J=6.93 Hz).

Step D: 1-(4-n-Octylphenyl)piperazine: A solution of the product of Step C (0.06 g; 0.16 mmol) in 60% TFA in CH$_2$Cl$_2$ (2 ml) was stirred for 15 min at room temperature and the mixture was diluted to 5 ml with EtOH and evaporated to dryness under reduced pressure and kept in vacuo for 1 h, to give a TFA salt of the title compound (0.07 g; 100%). $^1$H-NMR (CDCl$_3$) 9.5 (broad s, 2H); 7.29 (m, 4H); 3.8-3.16 (m, 8H); 2.6 (t, 2H, J=8 Hz); 1.58 (m, 2H); 1.26 (m, 10H); 0.86 (t, 3H, J=6.9 Hz).

Step E: tert-Butyl 2-(4-(4-octylphenyl)piperazin-1-yl)acetate: To a solution of the product of Step D (0.04 g, 0.146 mmol) and tert-butyl bromoacetate (0.026 ml; 0.16 mmol) in CH$_2$Cl$_2$ (1 ml) DIPEA (0.052 ml; 0.32 mmol) was added at room temperature under N$_2$. The mixture was stirred overnight at room temperature, diluted to 5 ml with Et$_2$O and washed with 0.1N HCl, H$_2$O, brine, dried over anhydrous MgSO$_4$ and filtered. The filtrate was evaporated under reduced pressure and the residue was purified by FCC (SiO$_2$, hexane/EtOAc 7:3) to give the title compound (0.05 g; 88%), as a colourless heavy syrup. $^1$H-NMR (CDCl$_3$) 7.05 (d, 2H, J=8.6 Hz); 6.83 (d, 2H, J=8.6 Hz); 3.32-3.15 (m, 6H); 2.73 (m, 4H); 2.5 (t, 2H, J=7.9 Hz); 1.55 (m, 2H); 1.46 (s, 9H); 1.26 (m, 10H); 0.86 (m, 3H).

Step F: 2-(4-(4-n-Octylphenyl)piperazin-1-yl)acetic acid: A solution of the product of Step E (0.05 g; 0.129 mmol) in 60% TFA in CH$_2$Cl$_2$ (5 ml) was refluxed for 2 h, cooled to room temperature then diluted to 7 ml with EtOH. The resulting mixture was evaporated to dryness under reduced pressure kept in vacuo for 1 h. The residue was treated dissolved in EtOH (2 ml) and 3 drops of concentrated NH$_4$OH was added. The resulting mixture was partially concentrated under reduced pressure and the precipitate, formed was filtered off, washed with Et$_2$O and dried to give the titled compound (0.02 g; 47%) as colourless solid. $^1$H-NMR (CD$_3$OD+CDCl$_3$) 7.07 (d, 2H, J=8.6 Hz); 6.86 (d, 2H, J=8.6 Hz); 4.63 (s, CD$_3$OH); 3.58 (s, 2H); 3.38 (m, 8H); 2.49 (t, 2H, J=7.8 Hz); 1.53 (m, 2H); 1.24 (m, 10H); 0.83 (m, 3H).

Example 10

2-(4-Octylphenethyl)propane-1,2,3-triol

Step A: 1-Ethynyl-4-octylbenzene: A mixture of Example 3, Step A (0.1 g; 0.46 mmol), dimethyl(1-diazo-2-oxoprpyl)

phosphonate (0.11 g, 0.57 mmol) and anhydrous K₂CO₃ (0.14 g, 1.01 mmol) in dry MeOH (5 ml) was stirred for 8 h under N₂. After removing solvent under reduced pressure, the residue was diluted to 15 ml with Et₂O and washed with H₂O (2×10 ml) and dried over anhydrous MgSO₄ and filtered. The filtrate was evaporated to dryness under reduced pressure and the residue was purified by FCC (SiO₂, hexane) to give the title compound (0.05 g; 51%) as colourless oil. $^1$H-NMR (CDCl₃) 7.38 (d, 2H, J=8.1 Hz); 7.11 (d, 2H, J=8.1 Hz); 3.0 (s, 1H); 2.58 (t, 2H, J=7.8 Hz); 1.58 (t, 3H, J=6.96 Hz); 1.27 (m, 10H); 0.86 (t, 3H, J=6.96 Hz).

Step B: 2,2-Dimethyl-5-((4-octylphenyl)ethynyl)-1,3-dioxan-5-ol: To a solution of the product of Step A (0.05 g; 0.233 mmol) in anhydrous THF (2 ml) 2 M n-butyllithium in cylohexane (0.13 ml; 0.26 mmol) was added drop wise at −15° C. under N₂. After stirring for 15 min at −15° C., 2,2-dimethyl-1,3-dioxan-5-one (0.034 g; 0.26 mmol) was added and the resulting mixture was allowed to warm up to room temperature, diluted to 15 ml with Et₂O and washed with H₂O (2×10 ml), brine and dried over anhydrous MgSO₄ and filtered. The filtrate was evaporated to dryness under reduced pressure and the residue was purified by FCC (SiO₂, hexane/EtOAc 95; 5) to give the title compound (0.03 g; 63%) as colourless oil. $^1$H-NMR (CDCl₃) 7.33 (d, 2H, J=8.09 Hz); 7.09 (d, 2H, J=8.09 Hz); 4.11 (d, 2H, J=11.76 Hz); 3.83 (d, 2H, J=11.76 Hz); 3.99 (s, 1H); 2.57 (t, 2H, J=7.88 Hz); 1.56 (t, 3H, J=6.94 Hz); 1.49 (s, 3H); 1.46 (s, 3H); 1.26 (m, 10H); 0.86 (t, 3H, J=6.96 Hz).

Step C: 2-(4-Octylphenethyl)propane-1,2,3-triol: A mixture of the product of Step B (0.03 g; 0.087 mmol) and 10% Pd/C (0.05 g) in 5% TFA in EtOH (10 ml) was stirred for 1 h under H₂ (balloon) at room temperature, then filtered through a pad of Celite, washed with CH₂Cl₂ (2×10 ml). To combined filtrates were evaporated to dryness under reduced pressure and dried in vacuo for 1 h to give title compound (0.027 g; 99%) as a colourless solid. $^1$H-NMR (CDCl₃) 7.05 (s, 4H); 3.66 (broad m, 7H); 2.61 (m, 2H); 2.51 (t, 2H, J=7.92 Hz); 1.73 (m 2H); 1.55 (t, 3H, J=6.93 Hz); 1.26 (m, 10H); 0.87 (t, 3H, J=6.93 Hz).

Example 11

3-(3-(4-n-Octylphenyl)ureido)propanoic acid

Step A: Ethyl 3-(3-(4-octylphenyl)ureido)propanoate: To 4-n-octylaniline (0.1 g; 0.49 mmol) ethyl 3-isocyanatopropionate (0.08 g; 0.54 mmol) was added at room temperature. The resulting mixture was diluted to 1 ml with CH₂Cl₂, refluxed for 30 min and evaporated to dryness. The residue was treated with Et₂O (5 ml) and the solid formed was filtered off and dried to give the title compound (0.15 g; 87%), as colourless crystals. $^1$H-NMR (CDCl₃) 7.22-7.07 (m, 4H); 6.34 (broad s, 1H); 5.34 (m, 1H); 4.15-4.07 (m, 2H); 3.54-3.46 (m, 2H); 2.73 (m, 4H); 2.57-2.51 (m, 4H); 1.58 (m, 2H); 1.27-1.19 (m, 13H); 0.86 (m, 3H).

Step B: 3-(3-(4-n-Octylphenyl)ureido)propanoic acid: To a solution of the product of Step A (0.05 g; 0.143 mmol) in dioxane (1 ml) 2N KOH (0.36 ml; 0.72 mmol) was added and the mixture was refluxed for 15 min, cooled to room temperature and evaporated to dryness under reduced pressure. The residue was diluted to 2 ml with H₂O and filtered. The filtrate was acidified to pH ~4 with citric acid. The solid formed was filtered off, washed with H₂O (3×2 ml), dried in vacuo to give the title compound (0.03 g; 65%), as a colourless solid. $^1$H-NMR (CD₃OD+CDCl₃) 7.16 (d, 2H, J=8.4 Hz); 7.0 (d, 2H, J=8.4 Hz); 4.21 (s, CD₃OH); 3.4 (t, 2H, J=6.7 Hz); 2.73 (m, 4H); 2.5-2.44 (m, 4H); 1.5 (m, 2H); 1.2 (m, 10H); 0.81 (m, 3H).

Example 12

3-(3-Methyl-3-(4-octylphenyl)ureido)propanoic acid

Step A: tert-Butyl 4-n-octylphenyl(methyl)carbamate: A mixture of 4-noctylaniline (0.09 g; 0.44 mmol) and di-tert-butyl dicarbonate (0.1 g; 0.46 mmol) and a few drops of triethylamine was stirred at −50° C. for 1 h under N₂, cooled to room temperature and kept in vacuo for 30 min. The residue was dissolved in anhydrous DMF (2 ml) and %60 NaH in mineral oil (0.02 g: 0.47 mmol) was added to it, followed by MeI (0.03 ml; 0.47 mmol), after stirring for 30 min under N₂. The resulting mixture was stirred for 3 h at room temperature and solvent was removed in vacuo. The residue was diluted to 15 ml with Et₂O and washed with 5% Na₂SO₃, H₂O, brine, dried over anhydrous MgSO₄ and filtered. The filtrate was evaporated under reduced pressure to give the title compound (0.14 g; 100%), as a creamy solid. $^1$H-NMR (CDCl₃) 7.14-6.99 (m, 4H); 3.22 (s, 3H); 2.55 (m, 2H); 1.56 (m, 2H); 1.43 (s, 9H); 1.26 (m, 10H); 0.86 (m, 3H).

Step B: N-Methyl-4-n-octylaniline: A solution of the product of Step A (0.14 g; 0.44 mmol) in 60% TFA in CH₂Cl₂ (5 ml) was stirred for 30 min at room temperature and the mixture was diluted to 5 ml with EtOH and a few drops of concentrated HCl was added. This was evaporated to dryness under reduced pressure, kept in vacuo for 1 h and the residue was partitioned between saturated NaHCO₃ (5 ml) and Et₂O (15 ml). The organic phase was dried over anhydrous MgSO₄ and filtered. The filtrate was evaporated under reduced pressure and the residue was purified by FCC (SiO₂, hexane/EtOAc 9:1) to give the title compound (0.055 g; 57%), as a creamy solid. $^1$H-NMR (CDCl₃) 7.01 (d, 2H, J=8.2 Hz); 6.55 (d, 2H, J=8.2 Hz); 3.55 (broad s, 1H); 2.81 (s, 3H); 2.49 (t, 2H, J=7.9 Hz); 1.56 (m, 2H); 1.28 (m, 10H); 0.88 (t, 3H, J=6.8 Hz).

Step C: Ethyl 3-(3-methyl-3-(4-octylphenyl)ureido)propanoate: When the product of Step B is substituted for 4-n-octylaniline in Example 11, Step A, the identical process afforded the title compound in 99% yield, as a colourless solid. $^1$H-NMR (CDCl₃) 7.15 (d, 2H, J=8.2 Hz); 7.05 (d, 2H, J=8.2 Hz); 4.77 (m, 1H); 4.03 (q, 2H, J=7.14 Hz); 3.54 (m, 2H); 3.37 (qr, 2H, J=6.1 Hz); 3.18 (s, 3H); 2.55 (t, 2H, J=7.5 Hz); 2.44 (t, 2H, J=6.1 Hz); 1.57 (m, 2H); 1.25 (m, 10H); 1.13 (t, 3H, J=7.14 Hz); 0.83 (t, 3H, J=6.9 Hz).

Step D: 3-(3-Methyl-3-(4-octylphenyl)ureido)propanoic acid: When the product of Step C is substituted for ethyl 3-(3-(4-octylphenyl)ureido)propanoate in Example 11, Step B, the identical process afforded the title compound in 84% yield, as a colourless solid. $^1$H-NMR (CDCl₃) 7.19 (d, 2H, J=8.3 Hz); 7.09 (d, 2H, J=8.3 Hz); 4.83 (m, 1H); 3.54 (m, 2H); 3.4 (m, 2H); 3.22 (s, 3H); 2.6-2.5 (m, 4H); 1.59 (m, 2H); 1.27 (m, 10H); 0.86 (t, 3H, J=7 Hz).

Example 13

3-(3-(4-Octylphenyl)-2-oxoimidazolidin-1-yl)propanoic acid

Step A: Ethyl 3-(3-(4-octylphenyl)-2-oxoimidazolidin-1-yl)propanoate: To a solution of the product of Example 11, Step A (0.05 g; 0.143 mmol) in anhydrous DMF (2 ml) 60% NaH in mineral oil (0.014 g; 0.344 mmol) was added at room temperature. After stirring for 1 h, to it 1,2-dibromoethane (0.172 ml; 0.2 mmol) was added. This was stirred at −50° C. for 1 h under $N_2$, cooled to room and solvents were removed in vacuo. The residue was diluted to 15 ml with $Et_2O$, washed with $H_2O$, brine, dried over anhydrous $MgSO_4$ and filtered. The filtrate was evaporated under reduced pressure and the residue was purified by FCC ($SiO_2$, hexane/EtOAc 9.5:0.5) to give the title compound (0.02 g; 37%) as a colourless solid. $^1$H-NMR ($CDCl_3$) 7.4 (d, 2H, J=8.5 Hz); 7.1 (d, 2H, J=8.5 Hz); 4.13 (q, 2H, J=7.1 Hz); 3.76 (m, 2H); 3.57 (t, 2H, J=6.7 Hz); 3.5 (m, 2H); 2.6 (t, 2H, J=6.7 Hz); 2.53 (t, 2H, J=7.9 Hz); 1.55 (m, 2H); 1.24 (m, 13H); 0.85 (t, 3H, J=6.9 Hz).

Step B: 3-(3-(4-Octylphenyl)-2-oxoimidazolidin-1-yl) propanoic acid: When the product of Step A is substituted for ethyl 3-(3-(4-octylphenyl)ureido)propanoate in Example 11, Step B, the identical process afforded the title compound in 33% yield, as a colourless solid. $^1$H-NMR ($CDCl_3$) 7.39 (d, 2H, J=8.4 Hz); 7.11 (d, 2H, J=8.4 Hz); 3.78 (t, 2H, J=7.3 Hz); 3.6-3.4 (m, 4H); 3.22 (s, 3H); 2.66 (t, 2H, J=6.5 Hz); 2.53 (t, 2H, J=7.7 Hz); 1.55 (m, 2H); 1.25 (m, 10H); 0.85 (t, 3H, J=6.9 Hz).

Example 14

2-(3-(4-Octylbenzyl)ureido)acetic acid

Step A: Ethyl 2-(3-(4-octylbenzyl)ureido)acetate: When the product of Example 6, Step C was substituted for 4-n-octylaniline and ethyl 2-isocyanatoacetate was substituted for ethyl 3-isocyanatopropionate in Example 11, Step A, the identical process afforded the title compound in 75% yield, as a colourless solid. $^1$H-NMR ($CDCl_3$) 7.18 (d, 2H, J=8 Hz); 7.11 (d, 2H, J=8 Hz); 4.86 (m, 1H); 4.78 (m, 1H); 4.32 (d, 2H, J=5.6 Hz); 4.16 (q, 2H, J=7.1 Hz); 3.97 (d, 2H, J=5.3 Hz); 2.56 (t, 2H, J=8 Hz); 1.56 (m, 2H); 1.25 (m, 13H); 0.86 (t, 3H, J=6.9 Hz).

Step B: 2-(3-(4-Octylbenzyl)ureido)acetic acid: When the product of Step A was substituted for ethyl 3-(3-(4-octylphenyl)ureido)propanoate in Example 11, Step B, the identical process afforded the title compound in 87% yield, as a colourless solid. $^1$H-NMR ($CDCl_3+CD_3OD$) 7.15 (d, 2H, J=8 Hz); 7.07 (d, 2H, J=8 Hz); 4.63 ($CD_3OH$); 4.26 (s, 2H); 3.86 (s, 2H); 2.52 (t, 2H, J=7.8 Hz); 1.54 (m, 2H); 1.22 (m, 10H); 0.83 (t, 3H, J=7 Hz).

Example 15

2-(3-(4-Octylbenzyl)-2-oxoimidazolidin-1-yl)acetic acid

Step A: tert-Butyl 2-(2-oxoimidazolidin-1-yl)acetate: To a solution of imidazolidin-2-one (0.2 g; 2.3 mmol) in anhydrous DMF (5 ml) 60% NaH in mineral oil (0.18 g; 4.6 mmol) was added at room temperature, under $N_2$. After stirring for 1 h, tert-butyl 2-bromoacetate (0.35 ml; 2.3 mmol) was added. The resulting mixture was stirred for additional 2 h and solvents were removed in vacuo. The residue was diluted to 15 ml with EtOAc, washed with $H_2O$, brine, dried over anhydrous $MgSO_4$ and filtered. The filtrate was evaporated under reduced pressure and the residue was purified by FCC ($SiO_2$, EtOAc) to give the title compound (0.12 g; 26%) as a colourless solid. $^1$H-NMR ($CDCl_3$) 4.61 (broad s, 1H); 3.83 (s, 2H); 3.58-3.41 (m, 4H); 1.44 (s, 9H).

Step B: tert-Butyl 2-(3-(4-octylbenzyl)-2-oxoimidazolidin-1-yl)acetate: To a solution of the product of Step A (0.03 g; 0.15 mmol) in anhydrous DMF (5 ml) 60% NaH in mineral oil (0.006 g; 0.15 mmol) was added at room temperature, under $N_2$. After stirring for 1 h, the product of Example 4, Step B (0.042 g; 0.15 mmol) was added. The resulting mixture was stirred for additional 4 h and solvents were removed in vacuo. The residue was diluted to 10 ml with EtOAc, washed with $H_2O$, brine, dried over anhydrous $MgSO_4$ and filtered. The filtrate was evaporated under reduced pressure and the residue was purified by FCC ($SiO_2$, hexane/EtOAc) to give the title compound (0.01 g; 16%) as a colourless solid. $^1$H-NMR ($CDCl_3$) 7.16 (d, 2H, J=8.1 Hz); 7.11 (d, 3H, J=8.1 Hz); 4.34 (s, 2H); 3.95 (s, 2H); 3.4 (m, 2H); 3.21 (m, 2H); 2.56 (t, 3H, J=7.9 Hz); 1.65 (m, 2H); 1.43 (s, 9H); 1.26 (m, 10H); 0.86 (t, 3H, J=7 Hz).

Step C: 2-(3-(4-Octylbenzyl)-2-oxoimidazolidin-1-yl) acetic acid: When the product of Step B was substituted for tert-butyl 2-(4-(4-octylphenyl)piperazin-1-yl)acetate in Example 9, Step F, the identical process afforded the title compound in 46% yield, as a colourless solid. $^1$H-NMR ($CDCl_3+CD_3OD$) 7.0 (m, 4H); 4.42 (s, 2H); 3.72 (s, 2H); 3.31 (m, 2H); 3.11 (m, 2H); 2.44 (t, 2H, J=7.8 Hz); 1.43 (m, 2H); 1.13 (m, 10H); 0.73 (t, 3H, J=7 Hz).

Example 16

2-(1-(4-Octylbenzyl)hydrazine-carboxamido)acetic acid

Step A: tert-Butyl 2-(4-octylbenzylidene)hydrazinecarboxylate: To a mixture of Example 3, Step A (0.1 g; 0.46 mmol) and tert-butyl carbazate (0.06 g; 0.46 mmol) in anhydrous $CH_2Cl_2$ (5 ml) anhydrous $MgSO_4$ was added and the resulting suspension was vigorously stirred for 2 h at room temperature and filtered. The filtrate was evaporated to dryness under reduced pressure to give the title compound (0.13 g; 87%) as yellowish solid, which was used in next step without further purification. $^1$H-NMR ($CDCl_3$) 7.8 (broad s, 1H); 7.56 (d, 2H, J=8.1 Hz); 7.15 (d, 2H, J=8.1 Hz); 2.58 (t, 2H, J=7.9 Hz); 1.59 (m, 2H); 1.52 (s, 9H); 1.26 (m, 10H); 0.86 (t, 3H, J=7 Hz).

Step B: tert-Butyl 2-(4-octylbenzyl)hydrazinecarboxylate: To a solution of the product of Step A (0.13 g; 0.391 mmol) in anhydrous THF (1 ml) and glacial AcOH (0.6 ml) $NaBH_3CN$ (0.06 g; 0.95 mmol) was added at −0° C. (ice bath). The resulting mixture was stirred overnight at room temperature then diluted to 15 ml with $Et_2O$. This was washed with 5% $NaHCO_3$ $H_2O$, brine, dried over anhydrous $MgSO_4$ and filtered. The filtrate was evaporated under reduced pressure to give the title compound (0.01 g; 16%) as a colourless syrup, which was used in the next step without further purification. $^1$H-NMR ($CDCl_3$) 7.23 (d, 2H, J=8 Hz); 7.12 (d, 3H, J=8 Hz); 6.0 (s, 1H); 4.1 (broad s, 2H); 3.94 (s, 2H); 2.57 (t, 3H, J=7.9 Hz); 1.56 (m, 2H); 1.45 (s, 9H); 1.26 (m, 10H); 0.86 (t, 3H, J=7 Hz).

Step C: tert-Butyl 2-(2-ethoxy-2-oxoethylcarbamoyl)-2-(4-octylbenzyl)-hydrazine-carboxylate: When the product of Step B was substituted for 4-n-octylbenzylamine in Example 14, Step A, the identical process afforded the title compound in 84% yield, as a colourless solid. $^1$H-NMR ($CDCl_3$) 7.14 (m, 4H); 5.95 (s, 1H); 5.87 (t, 1H, J=5 Hz); 4.5 (broad s, 1H); 4.19 (q, 2H, J=7.1 Hz); 4.03 (d, 2H, J=5 Hz); 2.57 (t, 2H, J=7.9 Hz); 1.56 (m, 2H); 1.44 (s, 9H); 1.27 (m, 13H); 0.86 (t, 3H, J=7 Hz).

Step D: Ethyl 2-(1-(4-octylbenzyl)hydrazinecarboxamido)acetate: When the product of Step C was substituted for tert-butyl 4-n-octylphenyl(methyl)carbamate in Example 12, Step B, the identical process afforded the title compound in 89% yield, as a creamy solid, which was used in the next step without further purification. $^1$H-NMR ($CDCl_3$) 7.15 (m, 4H); 6.84 (broad m, 1H); 4.66 (s, 2H); 4.2 (q, 2H, J=7.14 Hz); 4.02

(d, 2H, J=5.8 Hz); 3.42 (bs, 2H); 2.57 (t, 2H, J=7.9 Hz); 1.57 (m, 2H); 1.27 (m, 13H); 0.86 (t, 3H, J=6.9 Hz).

Step E: 2-(1-(4-Octylbenzyl)hydrazinecarboxamido)acetic acid: When the product of Step D is substituted for ethyl 3-(3-(4-octylphenyl)ureido)propanoate in Example 11, Step B, the identical process afforded the title compound in 78% yield, as a colourless solid. $^1$H-NMR (CDCl$_3$) 7.15 (m, 4H); 6.91 (t, 1H, J=5.7 Hz); 4.66 (s, 2H); 4.02 (d, 2H, J=5.7 Hz); 3.56 (bs, 3H); 2.57 (t, 2H, J=7.9 Hz); 1.58 (m, 2H); 1.26 (m, 10H); 0.86 (t, 3H, J=7 Hz).

Example 17

3-(5-Octylindoline-1-carboxamido)propanoic acid

Step A: 5-iodoindoline: To a solution of 5-iodoindole (0.2 g; 0.82 mmol) in AcOH (5 ml) NaBH$_3$CN (0.2 g; 3.8 mmol) was added at −10° C. under N$_2$. After stirring for 1 h at room temperature the solvent was removed in vacuo and the residue was diluted to 30 ml with Et$_2$O and washed with 1N NaOH (5 ml), H$_2$O (2×5 ml), brine, dried over anhydrous MgSO$_4$ and filtered. The filtrate was evaporated to dryness under reduced pressure to give the title compound (0.2 g; 99%), which was used in next step without further purification. $^1$H-NMR (CDCl$_3$) 7.35 (s, 1H); 7.25 (d, 1H, J=8.15 Hz); 6.43 (d, 1H, J=8.15 Hz); 5.21 (bs, 1H); 3.54 (t, 2H, J=8.36 Hz); 2.99 (t, 2H, J=8.36 Hz).

Step B: Ethyl 3-(5-iodoindoline-1-carboxamido)propanoate: When the product of Step A was substituted for 4-n-octylaniline in Example 11, Step A, the identical process afforded the title compound in 99% yield, as a colourless solid. $^1$H-NMR (CDCl$_3$) 7.67 (d, 1H, J=8.3 Hz); 7.4 (m, 2H); 5.34 (m, 1H); 4.14 (q, 2H, J=7.1 Hz); 3.86 (t, 2H, J=8.8 Hz); 3.56 (q, 2H, J=5.9 Hz); 3.13 (t, 2H, J=8.6 Hz); 2.58 (t, 2H, J=5.7 Hz); 1.26 (t, 3H, J=7.1 Hz).

Step C: Ethyl 3-(5-(oct-1-ynyl)indoline-1-carboxamido)propanoate: A mixture of the product of Step B (0.16 g; 0.41 mmol), 1-octyne (0.073 ml; 0.49 mmol), Cl$_2$Pd(PPh$_3$)$_2$ (0.02 g; 0.028 mmol) and CuI (0.005 g; 0.026 mmol) was degassed under reduced pressure and saturated with dry N$_2$. After addition of DIPEA (0.5 ml), the resulting mixture was stirred for 2 h at room temperature under N$_2$. The solvents were removed in vacuo and the residue was diluted to 15 ml with EtOAc and washed with 5% citric acid, 5% NaHCO$_3$, H$_2$O, brine and dried over anhydrous MgSO$_4$ and filtered. The filtrate was evaporated to dryness under reduced pressure and the residue was purified by FCC (SiO$_2$; CH$_2$Cl$_2$) to give the title compound (0.1 g; 65%) as a brownish solid. $^1$H-NMR (CDCl$_3$) 7.75 (d, 1H, J=8.4 Hz); 7.16 (d, 1H, J=8.4 Hz); 7.1 (s, 1H); 5.34 (t, 1H, J=5.8 Hz); 4.11 (q, 2H, J=7.1 Hz); 3.82 (t, 2H, J=8.8 Hz); 3.52 (m, 2H); 3.06 (t, 2H, J=8.8 Hz); 2.56 (t, 2H, J=5.8 Hz); 2.33 (t, 2H, J=7.1 Hz); 1.53 (m, 2H); 1.52 (m, 2H); 1.26 (m, 6H); 1.23 (t, 2H, J=7.1 Hz); 0.86 (t, 3H, J=6.9 Hz).

Step D: Ethyl 3-(5-octylindoline-1-carboxamido)propanoate: A mixture of the product of Step C (0.1 g; 0.27 mmol) and 10% Pd/C (0.1 g) in EtOH (15 ml) was stirred at room temperature for 1 h under H$_2$ (balloon). The catalyst was removed by filtration through the Celite pad, washed with CH$_2$Cl$_2$ (2×10 ml) and combined filtrates were evaporated to dryness under reduced pressure to give a title compound (0.09 g; 90%), as colourless solid. $^1$H-NMR (CDCl$_3$) 7.71 (d, 1H, J=8.8 Hz); 6.94 (d, 1H, J=8.8 Hz); 6.93 (s, 1H); 5.29 (m, 1H); 4.14 (q, 2H, J=7 Hz); 3.82 (t, 2H, J=8.8 Hz); 3.57 (q, 2H, J=5.9 Hz); 3.11 (t, 2H, J=8.6 Hz); 2.59 (t, 2H, J=5.7 Hz); 2.51 (t, 2H, J=7.7 Hz); 1.57 (m, 2H); 1.26 (m, 13H); 0.86 (t, 3H, J=7 Hz).

Step E: 3-(5-Octylindoline-1-carboxamido)propanoic acid: When the product of Step D was substituted for ethyl 3-(3-(4-octylphenyl)ureido)propanoate in Example 11, Step B, the identical process afforded the title compound in 84% yield, as a colourless solid. $^1$H-NMR (CDCl$_3$) 7.68 (d, 1H, J=8.7 Hz); 6.94 (m, 2H); 5.24 (t, 1H, J=5.9 Hz); 3.86 (t, 2H, J=8.7 Hz); 3.58 (q, 2H, J=5.9 Hz); 3.11 (t, 2H, J=8.5 Hz); 2.67 (t, 2H, J=5.8 Hz); 2.5 (t, 2H, J=8 Hz); 1.54 (m, 2H); 1.25 (m, 10H); 0.86 (t, 3H, J=6.8 Hz).

Example 18

4-(4-(N-(6,6-Dimethylbicyclo[3.1.1]heptan-2-yl)sulfamoyl)phenyl)butyl-dihydrogen phosphate Step A: 4-Bromo-N-(6,6-dimethylbicyclo[3.1.1]heptan-2-yl)benzene sulfonamide: To a stirred solution of 4-bromobenzenesulphonyl chloride (0.6 g, 2.34 mmol) in anhydrous CH$_2$Cl$_2$ (5 ml) and Et$_3$N (0.65 ml, excess) at 0° C. was added (−) cis-myrtanylamine (0.36 g, 2.34 mmol) and the stirring was continued overnight at room temperature. The reaction mixture was diluted with CH$_2$Cl$_2$ (15 ml) and washed with H$_2$O (2×100 ml). The organic layer was separated and dried over MgSO$_4$ and the solvent was distilled to afford the title compound (0.87 g, 100%), as pale paste, which was solidified on standing. $^1$H-NMR (CDCl$_3$) 7.70 (d, 2H, J=6.78 Hz); 6.64 (d, 2H, J=6.90 Hz); 2.91 (t, 2H, J=7.59 Hz); 2.32-2.29 (m, 1H); 2.11-2.06 (m, 1H); 1.91-1.81 (m, 6H); 1.39-1.31 (m, 1H); 1.11 (s, 3H); 0.86 (s, 3H).

Step B: N-(6,6-Dimethylbicyclo[3.1.1]heptan-2-yl)-4-(4-hydroxybut-1-ynyl)benzene sulfonamide: A solution of the product of Step A (0.37 g, 0.5 mmol) and but-3-yn-1-ol (0.12 ml, excess) in a mixture of DMF (5 ml) and DIPEA (0.5 ml) was degassed with N$_2$ and Cl$_2$Pd(PPh$_3$)$_2$ (0.07 g) was added, followed by catalytic amount of CuI and the mixture was stirred for 16 h at room temperature. The reaction was quenched with saturated NH$_4$Cl solution and diluted with H$_2$O followed by the extraction with EtOAc (100 ml). The organic layer was separated, dried over MgSO$_4$, filtered and the filtrate was evaporated to dryness and the residue was purified by FCC (SiO$_2$, hexane/EtOAc) to give the product (0.11 g, 60%), as creamy paste. $^1$H-NMR (CDCl$_3$) 7.66 (d, 2H, J=8.43 Hz); 7.51 (d, 2H, J=8.43 Hz); 3.81 (b, 2H); 3.01-2.86 (m, 2H); 2.71-2.67 (m, 4H); 2.50-2.10 (m, 2H); 1.94-1.82 (m, 5H); 1.52-1.48 (m, 1H); 1.18 (s, 3H); 1.02 (s, 3H).

Step C: N-(6,6-Dimethylbicyclo[3.1.1]heptan-2-yl)-4-(4-hydroxybutyl)benzene sulfonamide: A mixture of the product of Step B (0.11 g, 0.3 mmol) and 10% Pd/C (0.06 g) in EtOH (10 ml) was stirred for 16 h under H$_2$. The catalyst was filtered through Celite pad and the filtrate evaporated to dryness to give the title compound (0.11 g, 100%) as creamy gum. $^1$H-NMR (CDCl$_3$) 7.74 (d, 2H, J=7.89 Hz); 7.29 (d, 2H, J=8.01 Hz); 4.9 (bs, 1H, NH); 3.71-3.65 (m, 2H); 2.92-2.87 (m, 2H); 2.70 (t, 2H, J=7.74 Hz); 2.45-2.30 (m, 1H); 2.25-2.10 (m, 1H); 1.86-1.58 (m, 9H); 1.3-1.1 (m, 2H); 1.08 (s, 3H); 0.83 (s, 3H).

Step D: 4-(4-(N-(6,6-Dimethylbicyclo[3.1.1]heptan-2-yl)sulfamoyl)phenyl) butyl-dihydrogen phosphate: To a stirred solution of POCl$_3$ (0.006 ml, 0.66 mmol) in anhydrous CH$_2$Cl$_2$ (3 ml) a solution of tert-butanol (0.062 ml, 0.65 mmol) and Et$_3$N (0.09 ml, 0.65 mmol) was added drop wise at 0° C. under N$_2$. The mixture was stirred for 0.5 h and to it a solution of the product of Step C (0.08 g, 0.22 mmol) in a mixture of anhydrous CH$_2$Cl$_2$ (1 ml) and Et$_3$N (0.03 ml) was added drop wise. The mixture was stirred for 1 h at room temperature. The solvent was evaporated under reduced pressure and the residue was treated dropwise with a solution of 10% NaOH until the mixture become homogenous. This was washed with CH$_2$Cl$_2$ (2×10 ml), and the aqueous phase was acidified with 2M HCl. The product was extracted with CH$_2$Cl$_2$ (20 ml) and dried over MgSO$_4$ and filtered. The filtrate was evaporated to dryness to give the title compound (0.065 g, 65%) as pale paste. $^1$H-NMR (CDCl$_3$) 7.67 (d, 2H, J=7.13 Hz); 7.23 (d, 2H); 3.94 (bs, 1H, NH); 3.86 (d, 2H, J=7.67 Hz); 2.58 (b, 2H); 2.28 (b, 1H); 2.13 (b, 1H); 1.84-1.82 (b, 5H); 1.35 (b, 4H); 1.22-1.24 (b, 2H); 0.96 (s, 3H); 0.86 (s, 3H).

Example 19

4-(4-(3-(3-(2,2,2-trifluoroacetyl)-1H-indol-1-yl)propyl)phenyl)butyl-dihydrogen phosphate Step A: 2,2,2-Trifluoro-1-(1H-indol-3-yl)ethenone: To a stirred solution of indole (0.5 g, 4.3 mmol) in anhydrous Et$_2$O (10 ml) anhydrous pyridine (0.5 ml) was added at 0° C., followed by drop wise addition of (CF$_3$CO)$_2$O (0.87 ml, 5.16 mmol). The mixture was stirred for 15 min and the solvent was evaporated to dryness. The residue was diluted to 20 ml with EtOAc, washed with H$_2$O, dried over MgSO$_4$, filtered and the filtrate was evaporated to dryness. The residue was crystallized from CH$_3$OH to give the title compound (0.56 g; 61%), as colourless solid. $^1$H-NMR (CDCl$_3$) 9.04 (broad s, 1H); 8.40 (t, 1H, J=4.11 Hz); 8.06 (s, 1H); 7.48-7.45 (m, 1H); 7.40-7.35 (m, 2H).

Step B: 2,2,2-Trifluoro-1-(1-(prop-2-ynyl)-1H-indol-3-yl)ethanone: A mixture of product of Step A (0.55 g, 2.58 mmol), K$_2$CO$_3$ (0.43 g, 3.11 mmol) and propyrgyl bromide (2 ml) in anhydrous DMF (8 ml). was stirred for 4 h. The mixture was quenched with NH$_4$Cl solution and diluted to 50 ml with EtOAc. The organic layer separated and washed with H$_2$O, dried over MgSO$_4$ and filtered. The filtrate was evaporated to give the title compound (0.57 g, 88%), as yellow crystalline material. $^1$H-NMR (CDCl$_3$) 8.41-8.38 (b, 1H); 7.99 (s, 1H); 7.48-7.31 (m, 3H); 4.96 (d, 2H, J=2.55 Hz); 2.58 (t, 1H, J=2.55 Hz).

Step C: 2,2,2-Trifluoro-1-(1-(3-(4-iodophenyl)prop-2-ynyl)-1H-indol-3-yl)ethanone: A mixture of product of Step B (0.25 g, 1 mmol), 1,4 di-idobenzene (0.4 g, 1.2 mmol) Cl$_2$Pd(PPh$_3$)$_2$ (0.06 g) and catalytic amount of CuI in a mixture of DMF:DIPEA (10 ml: 0.5 ml) at room temperature was degassed under reduced pressure and saturated with N$_2$. This was stirred overnight at room temperature, quenched with NaHCO$_3$ solution and diluted to 50 ml with EtOAc. The organic layer was separated and washed with H$_2$O, dried over MgSO$_4$ and filtered. The filtrate was evaporated to dryness and the residue was purified by FCC (SiO$_2$, hexane/EtOAc) to give the title compound (0.28 g, 51%), as light yellow solid. $^1$H-NMR (CDCl$_3$) 8.43-8.40 (b, 1H); 8.12 (b, 1H); 7.66 (t, 2H, J=8.36 Hz); 7.55-7.51 (m, 1H); 7.44-7.38 (m, 2H); 7.14 (d, 2H, J=8.30 Hz); 5.16 (s, 2H).

Step D: 2,2,2-Trifluoro-1-(1-(3-(4-(4-hydroxybut-1-ynyl)phenyl)prop-2-ynyl)-1H-indol-3-yl)ethanone: When the product of Step C was substituted for 4-bromo-N-(6,6-dimethylbicyclo[3.1.1]heptan-2-yl)benzene sulphonamide in Example 18, Step B, the identical process afforded the title compound in 84% yield, as creamy paste. $^1$H-NMR (CDCl$_3$) 8.43-8.40 (m, 1H); 8.14 (s, 1H); 7.56-7.53 (m, 1H); 7.44-7.37 (m, 2H); 7.37 (s, 4H); 5.19 (s, 2H); 3.8 (t, 2H, J=6.24 Hz); 2.69 (t, 2H, J=6.24 Hz); 1.76 (bs, 1H).

Step E: 2,2,2-Trifluoro-1-(1-(3-(4-(4-hydroxybutyl)phenyl)propyl)-1H-indol-3-yl)ethanone: When the product of Step D was substituted for N-(6,6-dimethylbicyclo[3.1.1]heptan-2-yl)-4-(4-hydroxybut-1-ynyl)benzene sulphonamide in Example 18, Step C, the identical process afforded the title compound in 92% yield, as pale paste. $^1$H-NMR (CDCl$_3$) 8.40 (broad s, 1H); 7.86 (s, 1H); 7.37-7.32 (m, 3H); 7.11 (d, 2H, J=8.07 Hz); 7.05 (d, 2H, J=8.07 Hz); 4.19 (t, 2H, J=7.17 Hz); 3.72-3.63 (m, 4H); 2.66-2.59 (m, 4H); 1.68-1.60 (m, 4H).

Step F: 4-(4-(3-(3-(2,2,2-trifluoroacetyl)-1H-indol-1-yl)propyl)phenyl)butyl-dihydrogen phosphate: When the product of Step E was substituted for N-(6,6-dimethylbicyclo[3.1.1]heptan-2-yl)-4-(4-hydroxy butyl)benzene sulphonamide in Example 18, Step D, the similar process afforded the title compound in 73% yield, as pale paste. $^1$H-NMR (CDCl$_3$) 8.35 (broad s, 1H); 7.83 (s, 1H); 7.36-7.30 (m, 3H); 7.10-6.93 (m, 4H); 3.98 (m, 2H); 2.55-2.50 (m, 6H); 2.23-2.15 (m, 2H); 1.59 (b, 4H).

Example 20

4-(4-(2-(6,6-Dimethylbicyclo[3.1.1]heptan-2-yl)ethoxy)phenyl)butyl-dihydrogen phosphate Step A: 2-(2-(4-Iodophenoxy)ethyl)-6,6-dimethylbicyclo[3.1.1]heptane: To a stirred suspension of 4-iodophenol (0.5 g; 2.27 mmol) and 60% NaH (0.16 g, 2.3 mmol) in anhydrous DMF (5 ml) 2-(2-bromoethyl)-6,6-dimethylbicyclo[3.1.1]heptane (0.5 g, 2.2 mmol) was added the and mixture was stirred for 3 h at room temperature. After addition of more of 2-(2-bromoethyl)-6,6-dimethylbicyclo[3.1.1]heptane (0.2 g) the mixture was stirred for additional 2 h, quenched with NH$_4$Cl solution and diluted to 20 ml with EtOAc. The organic layer was separated, dried over MgSO$_4$ and filtered. The filtrate was evaporated to dryness and the residue was purified by FCC (SiO$_2$, hexane/EtOAc) to give the title compound (0.61 g, 73%), as a colourless paste. $^1$H-NMR (CDCl$_3$) 7.51 (d, 2H, J=8.91 Hz); 6.64 (d, 2H, J=8.88 Hz); 3.88 (t, 2H, J=3.21 Hz); 2.34-1.84 (m, 10H); 1.17 (s, 3H); 1.01 (s, 3H).

Step B: 4-(4-(2-(6,6-Dimethylbicyclo[3.1.1]heptan-2-yl)ethoxy)phenyl)but-3-yn-1-ol: When the product of Step A was substituted for 4-bromo-N-(6,6-dimethylbicyclo[3.1.1]heptan-2-yl)benzene sulphonamide in Example 18, Step B, the similar process afforded the title compound in 78% yield, as pale paste. $^1$H-NMR (CDCl$_3$) 7.29 (d, 2H, J=8.76 Hz); 6.78 (d, 2H, J=8.82 Hz); 3.80-3.76 (m, 2H); 3.92 (t, 2H, J=1.89 Hz); 2.65 (t, 2H, J=6.21 Hz); 1.92-1.81 (m, 10H); 1.18 (5, 3H); 1.01 (s, 3H).

Step C: 4-(4-(2-(6,6-Dimethylbicyclo[3.1.1]heptan-2-yl)ethoxy)phenyl) butan-1-ol: When the product of Step B was substituted for N-(6,6-dimethylbicyclo[3.1.1]heptan-2-yl)-4-(4-hydroxybut-1-ynyl)benzene sulphonamide in Example 18, Step C, the similar process afforded the title compound in 99% yield, as a colourless paste. $^1$H-NMR (CDCl$_3$) 7.05 (d, 2H, J=8.54 Hz); 6.78 (d, 2H, J=8.58 Hz); 3.91 (t, 2H, J=6.81 Hz); 3.64 (t, 2H, J=6.02 Hz); 2.57-2.53 (m, 2H); 1.90-1.57 (m, 14H); 1.18 (s, 3H); 1.01 (s, 3H).

Step D: 4-(4-(2-(6,6-Dimethylbicyclo[3.1.1]heptan-2-yl)ethoxy)phenyl) butyl-di-hydrogen phosphate: When the product of Step C was substituted for N-(6,6-dimethylbicyclo[3.1.1]heptan-2-yl)-4-(4-hydroxybutyl)benzene sulfonamide in Example 18, Step D, the similar process afforded the title compound in 60% yield, as pale paste. $^1$H-NMR (CDCl$_3$) 7.05 (d, 2H, J=8.31 Hz); 6.74 (d, 2H, J=8.16 Hz); 3.93-3.84 (m, 4H); 2.53-2.15 (m, 16H); 1.15 (s, 3H); 0.99 (s, 3H).

Example 21

2-(4-(2-(6-Methoxy-2,3-dihydrobenzofuran-2-yl)ethyl)phenoxy)ethanol

Step A: 4-((6-Methoxybenzofuran-2-yl)ethynyl)phenyl acetate: When 4-iodophenyl acetate and 2-ethynyl-6-methoxybenzofuran were substituted for 4-bromo-N-(6,6-dimethylbicyclo [3.1.1]heptan-2-yl)benzene sulphonamide and but-3-yn-1-ol respectively in Example 18, Step B, the similar process afforded the title compound in 56% yield, as creamy paste. $^1$H-NMR (CDCl$_3$) 7.56 (d, 2H, J=8.67 Hz); 7.41 (d, 1H, J=8.58 Hz); 7.10 (d, 2H, J=8.7 Hz); 6.97 (d, 1H, J=1.92 Hz); 6.9 (s, 1H); 6.88 (bd, 1H, J=8.61 Hz); 3.85 (5, 3H); 2.3 (s, 3H).

Step B: 4-(2-(6-Methoxy-2,3-dihydrobenzofuran-2-yl) ethyl)phenol: When the product of Step A was substituted for N-(6,6-dimethyl bicyclo[3.1.1]heptan-2-yl)-4-(4-hydroxy-but-1-ynyl)benzenesulphonamide in Example 18, Step C, the similar process (higher pressure of H$_2$) afforded the title compound in 96% yield, as creamy paste. $^1$H-NMR (CDCl$_3$) 7.25-7.19 (m, 2H); 7.02-6.97 (m, 3H); 6.38-6.35 (m, 2H); 4.81-4.72 (m, 1H); 3.75 (s, 3H); 3.24-3.16 (m, 1H); 2.83-2.73 (m, 3H); 2.27 (s, 3H); 2.13-2.07 (m, 1H); 2.06-1.92 (m, 1H).

Step C: Ethyl 2-(4-(2-(6-methoxy-2,3-dihydrobenzofuran-2-yl)ethyl)phenoxy)acetate: To a stirred solution of the product of Step A (0.05 g, 0.19 mmol) and K$_2$CO$_3$ (0.05 g, 0.36 mmol) in anhydrous DMF (5 ml) ethyl-bromo acetate (0.025 ml, 0.22 mmol) was added at room temperature. The mixture was stirred for 2 h and quenched with saturated NH$_4$Cl solution, extracted in EtOAc (100 ml) and washed with H$_2$O. The organic layer was separated and dried over MgSO$_4$ and filtered. The filtrate was evaporated to dryness to give the title compound (0.07 g; 100%), as pale oil. $^1$H-NMR (CDCl$_3$) 7.10 (d, 2H, J=8.39 Hz); 6.97 (d, 1H, J=8.46 Hz); 6.80 (t, 2H, J=8.36 Hz); 6.35-6.33 (m, 2H); 4.75-4.71 (m, 1H); 4.56 (s, 2H); 4.22 (q, 2H, J=14.36, 7.17 Hz); 3.72 (s, 3H, OMe); 3.2-3.13 (m, 1H); 2.79-2.69 (m, 3H); 2.0-1.87 (m, 2H); 1.26 (t, 3H, J=7.12 Hz).

Step D: 2-(4-(2-(6-Methoxy-2,3-dihydrobenzofuran-2-yl) ethyl)phenoxy)ethanol: To the stirred slurry of LiAlH$_4$ (0.01 g, 0.026 mmol) in anhydrous Et$_2$O (5 ml) the solution of the product of Step C (0.04 g, 0.11 mmol) in anhydrous Et$_2$O (2 ml) was added drop wise and stirring was continued for 0.5 h at room temperature. The reaction mixture was quenched with EtOAc: H$_2$O: MeOH mixture (7 ml: 3 ml: 1 ml), diluted to 20 ml with EtOAc and filtered through Celite. The filtrate was evaporated under reduced pressure and dried in vacuo to give the title compound (0.032 g, 94%), as colourless solid. $^1$H-NMR (CDCl$_3$) 7.13 (d, 2H, J=8.54 Hz); 6.99 (d, 1H, J=8.56 Hz); 6.84 (d, 2H, J=8.58 Hz); 6.38-6.34 (m, 2H); 4.79-4.74 (m, 1H); 4.65 (t, 2H, J=4.14 Hz); 3.96-3.90 (m, 2H); 3.75 (s, 3H); 3.22-3.14 (m, 1H); 2.82-2.68 (m, 2H); 2.11-1.91 (m, 3H).

Example 22

2-((4-(5-(((4-Fluorophenyl)(isopropyl)amino)methyl)thiophen-2-yl)benzyl) (methyl)amino)ethanol Step A: 4-(5-(Hydroxymethyl)thiophen-2-yl)benzaldehyde: The thiphene-5-al-2-boronic acid (0.47 g, 2.97 mmol) was reduced with NaBH$_4$ (0.15 g, 3.95 mmol) in MeOH (3 ml) and solvent was evaporated to dryness. The residue was taken in 1,4-dioxane (12 ml) and 4-bromobenzaldehyde (0.65 g, 3.5 mmol) was added. To this Pd(PPh$_3$)$_4$ (0.05 g) was added with stirring at 80° C., followed by the addition of a solution of NaHCO$_3$ (0.6 g) in H$_2$O (2 ml). The mixture was stirred at reflux for 1 h and the solvents were evaporated to dryness under reduced pressure. The residue was diluted to 100 ml with EtOAc and washed with H$_2$O. The organic layer was separated, dried over MgSO$_4$ and filtered. The filtrate was evaporated to dryness and the residue was purified by FCC (SiO$_2$, hexane/EtOAc) to give the title compound (0.61 g, 80%), as creamy paste. $^1$H-NMR (CDCl$_3$) 9.98 (s, 1H, CHO); 7.87 (d, 2H, J=8.3 Hz); 7.72 (d, 2H, J=8.31 Hz); 7.31 (d, 1H, J=3.74 Hz); 7.0 (d, 2H, J=3.7 Hz); 4.84 (s, 2H).

Step B: 4-(5-(((4-Fluorophenyl)(isopropyl)amino)methyl) thiophen-2-yl)benzaldehyde: To a stirred solution of the product of Step A (0.436 g, 2 mmol) in anhydrous CH$_2$Cl$_2$ (10 ml) and Et$_3$N (0.3 ml) mesyl chloride (0.4 ml) was added at 0° C. and stirring was continued for 1 h. The solvents were evaporated to dryness under reduced pressure and the residue was diluted to 50 ml with EtOAc and washed with H$_2$O. The organic layer was separated and dried over MgSO$_4$ and filtered. The filtrate was evaporated to give the crude product (0.63 g) as pale paste, which was taken up in anhydrous toluene and 4-fluoro-N-isopropylaniline (0.5 ml) was added to it. The mixture was stirred overnight at reflux and the solvent was evaporated. The residue was purified by FCC (SiO$_2$, hexane/EtOAc) to give the title compound (0.14 g, 20%), as light creamy paste. $^1$H-NMR (CDCl$_3$) 9.98 (s, 1H); 7.82 (d, 2H, J=8.31 Hz); 7.66 (d, 2H, J=8.31 Hz); 7.28 (d, 1H, J=3.69 Hz); 6.93-6.86 (m, 3H); 6.81-6.76 (m, 2H); 4.79 (s, 2H); 4.08-3.99 (m, 1H); 1.22 (d, 6H, J=6.6 Hz).

Step C: Methyl-2-((4-(5-(((4-fluorophenyl)(isopropyl) amino)methyl) thiophen-2-yl)benzyl)(methyl)amino) acetate: To a stirred solution of the product of Step B (0.09 g, 0.26 mmol) and sarcosine hydrochloride (0.07 g, 0.5 mmol) in 1,2-dichloroethane (5 ml) was added DIPEA (0.1 ml) and 10 drops of AcOH, followed by NaBH(OAc)$_3$ (0.11 g, 0.51 mmol). The mixture was stirred overnight at room temperature and diluted to 20 ml with CH$_2$Cl$_2$. The organic layer was washed with NaHCO$_3$ solution, H$_2$O and dried over MgSO$_4$ and filtered. The filtrate was evaporated to dryness and the residue was purified by FCC (SiO$_2$, hexane/EtOAc) to give the title compound (0.113 g, 100%) as creamy paste. $^1$H-NMR (CDCl$_3$) 7.47 (d, 2H, J=8.19 Hz); 7.28 (d, 2H, J=8.18 Hz); 7.10 (d, 1H, J=3.62 Hz); 6.88-6.85 (m, 3H); 6.85-6.77 (m, 2H); 4.44 (s, 2H); 4.07-3.98 (m, 1H); 3.69 (s, 3H); 3.24 (s, 2H); 2.37 (s, 3H); 1.21 (d, 6H, J=6.6 Hz).

Step D: 2-((4-(5-(((4-Fluorophenyl)(isopropyl)amino)methyl)thiophen-2-yl)benzyl)(methyl)amino)ethanol: When the product of Step C was substituted for ethyl-2-(4-(2-(6-methoxy-2,3-dihydrobenzofuran-2-yl)ethyl)phenoxy)acetate in Example 21, Step D, the similar process afforded the title compound in 28% yield, as light yellow paste. $^1$H NMR (CDCl$_3$) 7.47 (d, 2H, J=8.05 Hz); 7.24 (d, 2H, J=8.04 Hz); 7.10 (d, 1H, J=3.60 Hz); 6.91-6.85 (m, 3H); 6.81-6.76 (m, 2H); 4.44 (s, 2H); 4.07-3.98 (m, 1H); 3.61 (t, 2H, J=5.31 Hz); 3.53 (s, 3H); 2.58 (t, 2H, J=5.31 Hz); 2.21 (s, 3H); 1.21 (d, 6H, J=6.56 Hz).

Example 23

2-(4-(5-(((4-Fluorophenyl)(isopropyl)amino)methyl) thiophen-2-yl)benzylamino)propane-1,3-diol Step A: N-(4-(5-(((4-Fluorophenyl)(isopropyl)amino)methyl)thiophen-2-yl)benzyl)-2,2-dimethyl-1,3-dioxan-5-amine: When 2,2-dimethyl-1,3-dioxan-5-amine was substituted for sarcosine hydrochloride in Example 22, Step C, the similar process afforded the title compound in 90% yield, as creamy paste. $^1$H NMR (CDCl$_3$) 7.47 (d, 2H, J=8.2 Hz); 7.29 (d, 2H, J=8.2 Hz); 7.0 (d, 1H, J=3.61 Hz); 6.9-6.85 (m, 3H); 6.82-6.76 (m, 2H); 4.38 (s, 2H); 4.07-4.0 (m, 1H); 3.96 (dd, 2H, J=11.7, 3.5 Hz); 3.81 (s, 3H); 3.72 (dd, 2H, J=11.8, 5.34 Hz); 2.68-2.63 (m, 1H); 1.41 (s, 3H); 1.4 (s, 3H); 1.21 (d, 6H, J=6.6 Hz).

Step B: 2-(4-(5-(((4-Fluorophenyl)(isopropyl)amino)methyl)thiophen-2-yl)benzylamino)propane-1,3-diol: A solution of the product of Step A (0.025 g, 0.05 mmol) in a mixture of solvents (CH₃OH, CH₂Cl₂, 30% HCl: 1 ml, 3 ml, 15 drops) was stirred for 3 h at room temperature. The solvents were evaporated and co-evaporated with iPrOH to give the title compound (0.012 g, 48%) as creamy paste. $^1$H-NMR (CDCl₃) 7.45 (d, 2H, J=8.12 Hz); 7.23-7.33 (m, 4H); 7.16-7.09 (m, 3H); 6.88 (d, 2H, J=3.68 Hz); 4.95 (bs, 1H); 4.21 (s, 2H); 4.07-4.02 (m, 1H); 3.92-3.68 (m, 6H); 3.29-3.26 (m, 1H); 1.03 (d, 6H, J=6.6 Hz).

Example 24

2-(4-(3-((4-Fluorophenyl)(isopropyl)amino)propyl) benzylamino)propane-1,3-diol hydrochloride Step A: N-(3-(4-(Diethoxymethyl)phenyl)prop-2-ynyl)-4-fluorobenzenamine: When 4-bromo-benzene-diethylacetal and 4-fluoro-N-propyrgylaniline was substituted for 4-bromo-N-(6,6-dimethylbicyclo[3.1.1]heptan-2-yl)benzene sulphonamide and but-3-yn-1-ol, respectively, in Example 18, Step B, the similar process afforded the title compound in 36% yield, as pale paste. $^1$H-NMR (CDCl₃) 7.38 (d, 2H, J=8.7 Hz); 6.84 (d, 2H, J=8.6 Hz); 6.92 (t, 2H, J=7.8 Hz); 6.68-6.64 (m, 2H); 5.46 (s, 1H); 4.10 (s, 3H); 3.62-3.44 (m, 4H); 1.21 (t, 6H, J=7.04 Hz).

Step B: N-(3-(4-(Diethoxymethyl)phenyl)propyl)-4-fluorobenzenamine: When the product of Step A was substituted for N-(6,6-dimethylbicyclo[3.1.1]heptan-2-yl)-4-(4-hydroxybut-1-ynyl)benzene sulphonamide in Example 18, Step C, the similar process afforded the title crude product (0.195 g; 96%) as creamy paste. $^1$H-NMR (CDCl₃) 7.35 (d, 2H, J=8.01 Hz); 7.14 (d, 2H, J=8.1 Hz); 6.85 (t, 2H, J=7.54 Hz); 6.51-6.45 (m, 2H); 5.46 (s, 1H); 3.73-3.48 (m, 4H); 3.07 (t, 2H, J=6.97 Hz); 2.71 (t, 2H, 7.45 Hz); 1.96-1.85 (m, 2H); 1.22 (t, 6H, J=7.07 Hz).

Step C: 4-(3-((4-Fluorophenyl)(isopropyl)amino)propyl) benzaldehyde: A mixture of 4-(3-(4-fluorophenylamino)propyl)benzaldehyde (0.09 g, 0.35 mmol) [prepared form the product of Step B by stirring in acidifies CHCl₃] and 2-bromopropane (0.2 ml) and K₂CO₃ (0.1 g; 0.73 mmol) was stirred at reflux in anhydrous DMF (5 ml) for 6 h. The solvent was evaporated under reduced pressure and the residue was diluted to 50 ml with EtOAc and washed with H₂O. The organic layer separated and dried over MgSO₄ and filtered. The filtrate was evaporated to dryness and the residue was purified by FCC (SiO₂, hexane/EtOAc), to give the title compound (0.078 g, 83%) as creamy paste. $^1$H-NMR (CDCl₃) 10 (s, 1H); 7.78 (d, 2H, J=8.13 Hz); 7.32 (d, 2H, J=8.07 Hz); 6.93-6.86 (m, 2H); 6.82-6.66 (m, 2H); 3.07 (t, 2H, J=7.5 Hz); 2.71 (t, 2H, J=7.5 Hz); 2.71 (t, 2H, 7.62 Hz); 2.27-2.21 (m, 1H); 1.86-1.83 (m, 1H); 1.08 (d, 6H, J=6.6 Hz).

Step D: N-(4-(3-((4-Fluorophenyl)(isopropyl)amino)propyl)benzyl)-2,2-dimethyl-1,3-dioxan-5-amine: When the product of Step C and 2,2-dimethyl-1,3-dioxan-5-amine were substituted for 4-(5-(((4-fluorophenyl)(isopropyl)amino)methyl)-thiophen-2-yl)benzaldehyde and sarcosine hydrochloride in Example 22, Step C, the similar process afforded the title compound in 48% yield, as creamy paste. $^1$H-NMR (CDCl₃) 7.24 (d, 2H, J=7.92 Hz), 7.11 (d, 2H, J=7.92 Hz), 6.87 (t, 2H, J=8.9 Hz), 6.69-6.62 (m, 2H), 3.95 (dd, 2H, J=11.7, 3.6 Hz), 3.83-3.69 (m, 4H), 3.06 (t, 2H, J=7.54 Hz), 2.66-2.58 (m, 3H), 1.83-1.76 (m, 3H), 1.41 (s, 3H), 1.4 (s, 3H), 1.08 (d, 2H, 6.59 Hz).

Step E: 2-(4-(3-((4-Fluorophenyl)(isopropyl)amino)propyl)benzylamino) propane-1,3-diol hydrochloride salt: When the product of Step D was substituted for N-(4-(5-(((4-fluorophenyl)(isopropyl)amino)methyl)thiophen-2-yl)benzyl)-2,2-dimethyl-1,3-dioxan-5-amine in Example 23, Step B, the identical process afforded the title compound in 67% yield, as a creamy paste. $^1$H-NMR (CDCl₃) 7.39-7.19 (m, 6H); 7.11 (d, 2H, J=7.99 Hz); 4.21 (s, 2H); 3.94-3.67 (m, 5H); 3.4-3.7 (m, 2H); 3.3-3.26 (m, 1H); 2.56 (b, 2H); 1.68 (b, 1H); 1.22 (b, 1H); 1.04 (d, 6H, J=6.2 Hz).

Example 25

1-((4'-(N-(3-methoxyphenyl)-N-methylsulfamoyl) biphenyl-4-yl)methyl)azetidine-3-carboxylic acid Step A: 4-Bromo-N-(3-methoxyphenyl)benzenesulfonamide: To a stirred solution of 3-methoxyaniline (0.48 g, 3.92 mmol) in anhydrous pyridine (5 ml) 4-bromobenzene-sulphonyl chloride (0.5 g, 1.96 mmol) was added and the mixture was stirred for 0.5 h. The solvent was removed in vacuo and the residue was purified by FCC (SiO₂, hexane/EtOAc) to give the title compound (0.51 g, 37%) as creamy paste. $^1$H-NMR (CDCl₃) 7.65 (d, 2H, J=8.57 Hz); 7.52 (d, 2H, J=8.57 Hz); 7.10 (t, 1H, J=8.09 Hz); 6.69-6.61 (m, 2H); 4.37 (s, 2H); 3.71 (s, 3H, OMe).

Step B: 4-Bromo-N-(3-methoxyphenyl)-N-methylbenzenesulfonamide: To a stirred mixture of the product of Step A (0.5 g 1.46 mmol) and K₂CO₃ (0.5 g) in anhydrous DMF (7 ml) was added CH₃I (1 ml) and the stirring continued for 0.5 h at 50° C. The mixture was diluted to 50 ml with H₂O and extracted with EtOAc (50 ml). The organic layer was washed with H₂O and dried over MgSO₄, passed through silica gel bead and the filtrate was evaporated to dryness to give the title compound (0.5 g, 96%) as pale solid. $^1$H-NMR (CDCl₃) 7.58 (d, 2H, J=8.64 Hz); 7.40 (d, 2H, J=8.67 Hz); 7.18 (t, 1H, J=8.15 Hz); 6.80 (dd, 1H, J=8.34, 2.5 Hz); 6.69 (t, 1H, J=2.20 Hz); 6.58 (bd, 1H); 3.75 (s, 3H, OMe); 3.14 (s, 3H, N-Me).

Step C: 4'-Formyl-N-(3-methoxyphenyl)-N-methylbiphenyl-4-sulfonamide: When the product of Step B and 4-carbaldehyde-boronic acid were substituted for 4-bromobenzaldehyde and 5-(hydroxymethyl)thiophen-2-ylboronic acid, respectively, in Example 22, Step A, the similar process afforded the title compound in 73% yield, as pale solid. $^1$H-NMR (CDCl₃) 10.07 (s, 1H); 7.98 (d, 2H, J=6.56 Hz); 7.75 (d, 2H, J=8.24 Hz); 7.7 (d, 2H, J=8.82 Hz); 7.66 (d, 2H, J=8.75 Hz); 7.19 (t, 1H, J=8.13 Hz); 6.81 (dd, 1H, J=8.30, 2.45 Hz); 6.74 (t, 1H, J=2.17 Hz); 6.65 (dd, 1H, J=7.96, 1.24 Hz); 3.76 (s, 3H); 3.20 (s, 3H).

Step D: Methyl-1-((4'-(N-(3-methoxyphenyl)-N-methylsulfamoyl)biphenyl-4-yl)methyl) azetidine-3-carboxylate: When the product of Step C and azatadine 3 methylcarboxylate hydrochloride were substituted for 4-(5-(((4-fluorophenyl)(isopropyl)amino)methyl)thiophen-2-yl)benzaldehyde and sarcosine hydrochloride, respectively, in Example 22, Step C, the similar process the title compound in 69% yield, as pale paste. $^1$H-NMR (CDCl₃) 7.64 (d, 2H, J=8.8 Hz); 7.58 (d, 2H, J=8 Hz); 7.54 (d, 2H, J=8.15 Hz); 7.36 (d, 2H, J=8.12 Hz); 7.17 (t, 1H, J=8.14 Hz); 6.80 (dd, 1H, J=8.07, 2.21 Hz); 6.72 (t, 1H, J=2.10 Hz); 6.64 (dd, 1H, J=7.80, 1.67 Hz); 3.74 (s, 3H); 3.71 (s, 2H); 3.69 (s, 3H); 3.64-3.58 (m, 2H); 3.42-3.36 (m, 4H); 3.18 (s, 3H).

Step E: 1-((4'-(N-(3-methoxyphenyl)-N-methylsulfamoyl)biphenyl-4-yl)methyl)azetidine-3-carboxylic acid: To a stirred solution of the product of Step D (0.06 g, 0.13 mmol) in THF (3 ml) a solution of LiOH (0.006 g, 0.25 mmol) in H₂O (1 ml) was added at 80° C. The mixture was stirred for 0.5 h and solvents were evaporated to dryness. The residue was purified by FCC (SiO₂) to give the title compound (0.0026 g, 43%) as creamy solid. $^1$H-NMR (CDCl₃:CD₃OD) 7.58 (s, 4H); 7.58 (d, 2H, J=8 Hz); 7.56 (d, 2H, J=7.23 Hz);

7.49 (d, 2H, J=8.25 Hz); 7.13 (t, 1H, J=8.14 Hz); 6.76 (dd, 1H, J=8.33, 2.05 Hz); 6.68 (t, 1H, J=2.15 Hz); 6.58 (dd, 1H, J=7.94, 1.32 Hz); 4.25 (s, 2H); 4.21-4.02 (m, 4H); 3.70 (s, 3H); 3.38-3.32 (m, 3H); 3.13 (s, 3H).

Example 26

2-(((4'-(((4-Fluorophenyl)(isopropyl)amino)methyl)biphenyl-4-yl)methyl)(methyl)amino)acetic acid Step A: 4-Fluoro-N-isopropylaniline: A mixture of 4-fluoro-aniline (1.12 g; 10 mmol), 2-bromopropane (1.13 ml) and K$_2$CO$_3$ (1.38 g, 10 mmol) in anhydrous DMF (6 ml) was stirred for 5 h at reflux. The mixture was cooled to room temperature, diluted to 100 ml with H$_2$O and extracted with EtOAc (50 ml). The organic layer was washed with H$_2$O (2×20 ml) and dried over MgSO$_4$ and filtered. The filtrate was evaporated to dryness and the residue was purified by FCC (SiO$_2$, hexane/EtOAc) to give the title compound (0.65 g; 43%), as light yellow oil. $^1$H-NMR (CDCl$_3$) 6.89-6.82 (m, 2H); 6.53-6.47 (m, 2H); 3.58-3.49 (m, 1H); 1.18 (d, 6H, J=6.25 Hz).

Step B: N-(4-Bromobenzyl)-4-fluoro-N-isopropylbenzenamine: When the product of Step A and 4-bromobenzaldehyde were substituted for sarcosine hydrochloride salt and 4-(5-(((4-fluorophenyl)) isopropyl)amino)methyl)thiophen-2-yl)benzaldehyde, respectively, in Example 22, Step C, the similar process afforded the title compound in 93% yield, as a pale paste. $^1$H-NMR (CDCl$_3$) 7.39 (d, 2H, J=8.18 Hz); 7.14 (d, 2H, J=8.08 Hz); 6.91-6.81 (m, 2H); 6.62-6.57 (m, 2H); 4.26 (s, 2H); 4.11-4.04 (m, 1H); 1.18 (d, 2H, J=5.34 Hz).

Step C: 4'-(((4-Fluorophenyl)(isopropyl)amino)methyl)biphenyl-4-carbaldehyde: When the product of Step B and 4-carbaldehyde-boronic acid were substituted for 4-bromobenzaldehyde and 5-(hydroxymethyl) thiophen-2-ylboronic acid, respectively, in Example 22, Step A, the similar process afforded the title compound in 65% yield, as creamy gum. $^1$H-NMR (CDCl$_3$) 10.03 (s, 1H); 7.92 (d, 2H, J=7.97 Hz); 7.56 (d, 2H, J=7.95 Hz); 7.38 (d, 2H, J=8.29 Hz); 6.86 (t, 2H, J=8.46 Hz); 6.67-6.62 (m, 2H); 4.38 (s, 2H); 4.17-4.12 (m, 1H); 1.2 (d, 6H, J=6.96 Hz).

Step D: Methyl-2-(((4'-(((4-fluorophenyl)isopropyl)amino)methyl)biphenyl-4-yl)methylmethyl)amino)acetate: When the product of Step C was substituted for 4-(5-(((4-fluorophenyl))isopropyl)amino)methyl)thiophen-2-yl)benzaldehyde in Example 22, Step C, the similar process afforded the title compound in 96% yield, as a creamy paste. $^1$H-NMR (CDCl$_3$) 7.54-7.49 (m, 4H); 7.38-7.31 (m, 4H); 6.86 (t, 2H, J=8.45 Hz); 6.83-6.64 (m, 2H); 4.37 (s, 2H); 4.19-4.09 (m, 1H); 3.70 (5, 3H); 3.69 (s, 2H); 3.28 (s, 2H); 2.4 (s, 3H); 1.17 (d, 6H, J=7.71 Hz).

Step E: 2-(((4'-(((4-Fluorophenyl)(isopropyl)amino)methyl)biphenyl-4-yl)methyl)(methyl)amino)acetic acid: When the product of Step D was substituted for methyl-1-(4-((5-chlorobenzofuran-3-yl)methoxy)benzyl) azetidine-3-carboxylate in Example 25, Step E, the similar process afforded the title compound in 87% yield, as creamy solid. $^1$H-NMR (CDCl$_3$+CD$_3$OD) 7.40-7.18 (m, 8H); 6.76 (t, 2H, J=8.82 Hz); 6.61-6.56 (m, 2H); 4.25 (s, 2H); 4.16 (s, 2H); 4.07-4.01 (m, 1H); 2.59 (s, 3H); 1.11 (d, 6H, J=6.48 Hz).

Example 27

1-((4'-(((4-Fluorophenyl)(isopropyl)amino)methyl)biphenyl-4-yl)methyl)azetidine-3-carboxylic acid Step A: Methyl-1-((4'-(((4-fluorophenyl)(isopropyl)amino)methyl)biphenyl-4-yl)methyl)azetidine-3-carboxylate: When 4'-(((4-Fluorophenyl)(isopropyl)amino)methyl)biphenyl-4-carbaldehyde and azatadine 3-methylcarboxylate hydrochloride were substituted for 4-(5-(((4-fluorophenyl))isopropyl)amino)-methyl)thiophen-2-yl)benzaldehyde and sarcosine hydrochloride, respectively, in Example 22, Step C, the similar process afforded the title compound in 65% yield, as creamy paste. $^1$H-NMR (CDCl$_3$) 7.53 (d, 2H, J=8.12 Hz); 7.48 (d, 2H, J=8.2 Hz); 6.85 (t, 2H, J=9.09 Hz); 6.67-6.62 (m, 2H); 4.37 (s, 2H); 4.16-4.11 (m, 1H); 3.86 (bs, 4H); 3.69 (s, 3H); 3.58-3.51 (m, 1H); 1.19 (d, 6H, J=6.63 Hz).

Step B: 1-((4'-(((4-Fluorophenyl)(isopropyl)amino)methyl)biphenyl-4-yl)methyl)azetidine-3-carboxylic acid: When the product of Step A was substituted for methyl-1-(4-((5-chlorobenzofuran-3-yl)methoxy)benzyl)azetidine-3-carboxylate in Example 25, Step E, the similar process afforded the title compound in 60% yield, as creamy solid. $^1$H-NMR (CDCl$_3$+CD$_3$OD) 7.66 (d, 2H, J=8.13 Hz); 7.62-7.57 (m, 4H); 7.41 (d, 2H, J=8.07 Hz); 6.95-6.85 (m, 2H); 6.85-6.75 (m, 2H); 4.44 (s, 2H); 4.39 (s, 2H); 4.39-4.2 (m, 2H); 3.5-3.45 (m, 1H); 1.26 (d, 6H, J=6.54 Hz).

Example 28

1-(4-(4-oxo-4-(3,4,5-trimethoxyphenyl)but-2-en-2-yl)benzyl)azetidine-3-carboxylic acid Step A: 3-Bromo-1-(3,4,5-trimethoxyphenyl)but-2-en-1-one: 1-(3,4,5-trimethoxyphenyl) but-2-yn-1-one (0.5 g, 2.58 mmol) was dissolved in AcOH (5 ml) and 48% HBr (5 drops) was added to it. The mixture was stirred for 2 h at 50° C. This was evaporated to dryness and the residue was diluted to 50 ml with EtOAc, washed with NaHCO$_3$ solution and H$_2$O. The organic layer was dried over MgSO$_4$ and filtered. The filtrate was evaporated to dryness and dried in vacuo to give the title compound (0.53 g, 65%), as a pale solid. $^1$H-NMR (CDCl$_3$) 7.30 (s, 1H); 7.03 (s, 2H); 3.91 (s, 9H); 2.79 (s, 3H).

Step B: 4-(4-oxo-4-(3,4,5-trimethoxyphenyl)but-2-en-2-yl)benzaldehyde: When the product of Step A and 4-carbaldehyde-boronic acid were substituted for 5-(hydroxymethyl) thiophen-2-ylboronic acid and 4-bromobenzaldehyde, respectively, in Example 22, Step A, the similar process afforded the title compound in 81% yield, as creamy gum. $^1$H-NMR (CDCl$_3$) 10.05 (s, 1H); 7.92 (d, 2H, J=8.25 Hz); 7.68 (d, 2H, J=8.28 Hz); 7.23 (s, 2H); 7.10 (s, 1H); 3.91 (s, 9H); 2.55 (s, 3H).

Step C: Methyl-1-(4-(4-oxo-4-(3,4,5-trimethoxyphenyl)but-2-en-2-yl)benzyl) azetidine-3-carboxylate: When the product of Step B and azatadine 3 methylcarboxylate hydrochloride were substituted for 4-(5-(((4-fluorophenyl)) isopropyl)amino)methyl)thiophen-2-yl)benzaldehyde and sarcosine hydrochloride, respectively, in Example 22, Step-C, the similar process afforded the title compound in 66% yield, as pale paste. $^1$H-NMR (CDCl$_3$) 7.49 (d, 2H, J=8.28 Hz); 7.30 (d, 2H, J=8.29 Hz); 7.22 (s, 2H), 7.06 (s, 1H); 3.90 (s, 9H); 3.68 (s, 3H); 3.64 (s, 2H); 3.56-3.52 (m, 2H); 3.37-3.32 (m, 3H).

Step D: 1-(4-(4-oxo-4-(3,4,5-trimethoxyphenyl)but-2-en-2-yl)benzyl)azetidine-3-carboxylic acid: When the product of Step C was substituted for methyl-1-(4-((5-chlorobenzofuran-3-yl)methoxy)benzyl)azetidine-3-carboxylate in Example 25, Step E, the similar process afforded the title compound in 53% yield, as light yellow solid. $^1$H-NMR (CDCl$_3$+CD$_3$OD) 7.31 (d, 2H, J=8.18 Hz); 7.28 (d, 2H, J=8.28 Hz); 6.71 (s, 2H); 6.62 (s, 1H); 4.24 (s, 2H); 4.17-4.04 (m, 4H); 3.55-3.38 (s, 1H); 2.15 (s, 3H).

Example 29

1-((4'-(3-(3-(Trifluoromethyl)phenyl)but-2-enoyl)biphenyl-4-yl)methyl)azetidine-3-carboxylic acid Step A: 1-(4-Bromophenyl)but-2-yn-1-one: To an ice cold solution of 4-bromobenzaldehyde (1.3 g, 7 mmol) 0.5 M solution of propynyl magnesium bromide in THF (15 ml, 7.5 mmol) was added under $N_2$. The mixture was stirred for 10 min, quenched with saturated $NH_4Cl$ solution and diluted to 50 ml with EtOAc. The organic layer was washed with $H_2O$, dried over $MgSO_4$ and filtered. The filtrate was evaporated to dryness and the residue was dissolved in 1,4-dioxane (25 ml). To it $MnO_2$ (2 g) was added and the resulting suspension was stirred for 4 h at reflux. The mixture was filtered through Celite pad and the filtrate was evaporated to dryness and dried in vacuo to give the title compound (1.29 g, 83%) as a pale solid. $^1$H-NMR ($CDCl_3$) 7.97 (d, 2H, J=9 Hz); 7.61 (d, 2H, J=9 Hz); 2.14 (s, 3H).

Step B: 4'-But-2-ynoylbiphenyl-4-carbaldehyde: When the product of Step A and 4-carbaldehyde-boronic acid were substituted for 4-bromobenzaldehyde and 5-(hydroxymethyl)thiophen-2-ylboronic acid, respectively, in Example 22, Step A, the similar procedure afforded the title compound in 58% yield, as a creamy gum. $^1$H-NMR ($CDCl_3$) 10.07 (s, 1H); 8.23 (d, 2H, J=8.4 Hz); 7.98 (d, 2H, J=8.4 Hz); 7.78 (d, 2H, J=8.24 Hz); 7.72 (d, 2H, J=8.54 Hz); 2.18 (s, 3H).

Step C: 4'-(3-Bromobut-2-enoyl)biphenyl-4-carbaldehyde: When the product of Step B was substituted for 1-(3,4,5-trimethoxyphenyl)but-2-yn-1-one in Example 28, Step A, the similar process afforded the title compound in 56% yield, as pale solid. $^1$H-NMR ($CDCl_3$) 10.07 (s, 1H); 8.03-7.96 (m, 4H); 7.79-7.71 (m, 4H); 7.41 (s, 1H); 2.84 (s, 3H).

Step D: 4'-(3-(3-(Trifluoromethyl)phenyl)but-2-enoyl)biphenyl-4-carbaldehyde: When the product of Step C and 3-trifluoromethyl-boronic acid were substituted for 4-bromo benzaldehyde and 5-(hydroxymethyl)thiophen-2-ylboronic acid, respectively, in Example 22, Step A, the similar procedure afforded the title compound in 73% yield, as creamy gum. $^1$H-NMR ($CDCl_3$) 10.07 (s, 1H); 8.1 (d, 2H, J=8.5 Hz); 7.99-7.93 (m, 3H); 7.8-7.57 (m, 5H); 7.18 (s, 1H); 2.61 (s, 3H).

Step E: Methyl-1-((4'-(3-(3-(trifluoromethyl)phenyl)but-2-enoyl)biphenyl-4-yl)methyl)azetidine-3-carboxylate: When the product of Step D and azatadine 3 methylcarboxylate hydrochloride were substituted for 4-(5-(((4-fluorophenyl)) isopropyl)amino)methyl)thiophen-2-yl)benzaldehyde and sarcosine hydrochloride, respectively, in Example 22, Step C, the similar procedure afforded the title compound in 58% yield, as a pale paste. $^1$H-NMR ($CDCl_3$) 8.04 (d, 2H, J=8.4 Hz); 7.78-7.51 (m, 8H); 7.4 (d, 2H, J=8.2 Hz); 7.16 (d, 1H, J=1.21 Hz); 3.76 (s, 2H); 3.7 (s, 3H); 3.73-3.62 (m, 4H); 3.47-3.41 (m, 3H); 2.58 (bs, 3H).

Step F: 1-((4'-(3-(3-(Trifluoromethyl)phenyl)but-2-enoyl)biphenyl-4-yl)methyl)azetidine-3-carboxylic acid: When the product of Step E was substituted for methyl-1-(4-((5-chlorobenzofuran-3-yl)methoxy)benzyl)azetidine-3-carboxylate in Example 25, Step E, the similar process afforded the title compound in 62% yield, as a light yellow solid. $^1$H-NMR ($CDCl_3$+$CD_3OD$) 7.84 (d, 2H, J=8.34 Hz); 7.59-7.33 (m, 6H); 4.7 (d, 2H); 3.96-3.92 (m, 4H); 3.19-3.14 (m, 1H); 2.36 (s, 3H).

Example 30

1-(4-(4-oxo-2-phenyl-4H-chromen-6-yl)benzyl)azetidine-3-carboxylic acid

Step A: 5-Bromo-2-isopropoxybenzaldehyde: To a stirred solution of 2-isopropoxybenzaldehyde (0.51 g, 3.1 mmol), in DMF (10 ml) NBS (0.55 g, 3.1 mmol) was added and the reaction mixture was stirred overnight at room temperature. The reaction was quenched with $NaHCO_3$ solution and extracted in EtOAc (50 ml). The organic layer was washed with $H_2O$, dried over $MgSO_4$ and filtered. The filtrate was evaporated to dryness to give the title compound (0.62 g, 82%) as light yellow oil. $^1$H-NMR ($CDCl_3$) 10.37 (s, 1H); 7.89 (d, 1H, J=2.52 Hz); 7.55 (dd, 1H, J=8.85, 2.58 Hz); 6.87 (d, 1H, J=8.88 Hz); 4.67-4.58 (m, 1H); 1.35 (d, 6H, J=6.03 Hz).

Step B: 1-(5-Bromo-2-isopropoxyphenyl)-3-phenylprop-2-yn-1-one: To a stirred solution of phenyl-acetylene (0.27 ml, 2.46 mmol) in anhydrous THF (3 ml) 2M iPrMgCl in THF (1.25 ml) was added drop wise at 0° C. under $N_2$. After stirring for 15 min, the solution of product of Step A (0.5 g, 2.06 mmol) in anhydrous THF (2 ml) was added drop wise and the mixture was stirred for 1 h at room temperature. The mixture was quenched with saturated $NH_4Cl$ and extracted with EtOAc (50 ml). The organic layer was washed with $H_2O$, dried over $MgSO_4$. and filtered. The filtrate was evaporated to dryness to give a creamy paste (0.59 g; 83%). [$^1$H-NMR ($CDCl_3$) 7.68 (d, 1H, J=2.49 Hz); 7.46-7.43 (m, 2H); 7.36 (dd, 1H, J=8.75, 2.54 Hz); 7.32-7.28 (m, 3H); 6.79 (d, 1H, J=6.77 Hz); 5.79 (d, 1H, J=5.23 Hz); 4.64-4.58 (m, 1H); 3.13 (d, 1H, J=5.91 Hz); 1.37 (d, 6H)]. This was dissolved in dioxane (10 ml) and $MnO_2$ (1 g) was added to it. The resulting suspension was stirred for 6 h at reflux, then filtered through Celite and the solvent was evaporated to dryness to give the title compound (0.54 g, 76.5%), as light yellow paste. $^1$H-NMR ($CDCl_3$) 8.00 (d, 1H, J=2.61 Hz); 7.61-7.52 (m, 3H); 7.44-7.35 (m, 3H); 6.88 (d, 1H, J=8.91 Hz); 4.68-4.60 (m, 1H); 1.36 (d, 6H).

Step C: 4-(4-Oxo-2-phenyl-4H-chromen-6-yl)benzaldehyde: A solution of the product of Step B (0.3 g, 0.88 mmol), was treated with HBr/AcOH, as described in Example 28, Step A, to give a light creamy solid (0.18 g, 68%). $^1$H-NMR ($CDCl_3$) 8.36 (d, 1H, J=2.43 Hz); 7.92-7.88 (m, 2H); 7.77 (dd, 1H, J=8.88, 2.46 Hz); 7.58-7.50 (m, 3H); 7.47 (d, 1H, J=8.86 Hz); 6.83 (s, 1H)], which was reacted with 4-carbaldehyde-boronic acid in Example 22, Step A, to give the title compound (0.078 g, 48%), as creamy solid. $^1$H-NMR ($CDCl_3$) 10.07 (s, 1H); 8.5 (d, 1H, J=2.31 Hz); 8.00-7.93 (m, 2H); 7.84 (d, 2H, J=8.22 Hz); 7.71-7.63 (m, 3H); 7.56-7.48 (m, 3H); 6.87 (s, 1H).

Step D: Methyl 1-(4-(4-oxo-2-phenyl-4H-chromen-6-yl)benzyl)azetidine-3-carboxylate: When the product of Step C and azatadine 3 methylcarboxylate hydrochloride were substituted for -(5-(((4-fluorophenyl))isopropyl)amino)methyl)thiophen-2-yl)benzaldehyde and sarcosine hydrochloride, respectively, as in Example 22, Step C, the similar procedure afforded the title compound in 31% yield, as light green paste. $^1$H-NMR ($CDCl_3$) 8.43 (d, 1H, J=2.29 Hz); 7.96-7.91 (m, 3H); 7.63 (d, 3H); 7.54-7.39 (m, 3H); 7.38 (d, 2H, J=8.18 Hz); 6.85 (s, 1H); 3.73 (s, 3H); 3.71 (s, 2H); 3.71-3.62 (broad, 2H); 3.42-3.35 (b, 3H).

Step E: 1-(4-(4-oxo-2-phenyl-4H-chromen-6-yl)benzyl)azetidin e-3-carboxylic acid: When the product of Step D was substituted for methyl-1-(4-((5-chlorobenzofuran-3-yl)methoxy)benzyl)azetidine-3-carboxylate in Example 25, Step E, the similar process afforded the title compound in 36% yield, as creamy solid. $^1$H-NMR ($CDCl_3$+$CD_3OD$) 8.31 (broad s, 1H); 7.86 (broad s, 3H); 7.77-7.52 (m, 7H); 6.69 (s, 1H); 4.21 (broad s, 2H); 4.18-4.02 (m, 4H); 3.3 (s, 1H).

Example 31

3'-(1-Admantanyl)-4'methoxybiphenyl-4-yl)methyl)azetidine-3-carboxylic acid

Step A: 2-(1-Admantanyl)-4-bromophenol: To a stirred solution of 4-bromophenol (1 g; 5.8 mmol) and admant-1-ol (0.88 g; 5.8 mmol) in AcOH (5 ml) concentrated H$_2$SO$_4$ (1 ml) was added drop wise and stirring was continued for 50 h. The solvent was distilled to half of the volume and the mixture was poured onto ice cold H$_2$O (100 ml) and extracted with EtOAc (150 ml). The organic layer was washed with NaHCO$_3$ solution, dried over MgSO$_4$ and filtered. The filtrate was evaporated to dryness and the residue was purified by FCC (SiO$_2$, hexane/EtOAc) to give the title compound (0.976 g, 55%), as a colourless solid. $^1$H-NMR (CDCl$_3$) 7.27 (d, 1H, J=2.43 Hz); 7.13 (dd, 1H, J=8.4-2.43 Hz); 6.51 (d, 1H, J=8.37 Hz); 4.76 (s, 1H, OH); 2.07 (s, 10H); 1.75 (b, 5H).

Step B: 2-(1-Admantanyl)-4-bromomethoxybenzene: To a stirred mixture of the product of Step A (0.5 g; 1.62 mmol) and K$_2$CO$_3$ (0.335 g; 2.42 mmol) in danhydrous DMF (5 ml) CH$_3$I (1 ml) was added. The reaction mixture was stirred for 2 h and then diluted to 100 ml with H$_2$O and extracted with EtOAc (100 ml). The organic layer was dried over MgSO$_4$ and filtered. The filtrate was passed through silica gel bead. The filtrate was evaporated to dryness to give the title compound (0.49 g, 94%), as light yellow green solid. $^1$H-NMR (CDCl$_3$) 7.27-7.22 (m, 2H); 6.31 (d, 1H, J=6.5 Hz); 3.78 (s, 3H); 2.04 (s, 10H); 1.74 (b, 5H).

Step C: 3'-(1-Admantanyl)4'methoxy-4-carbaldehyde: When the product of Step B and 4-carbaldehyde-boronic acid were substituted for 4-bromobenzaldehyde and 5-(hydroxymethyl)thiophen-2-ylboronic acid, respectively, in Example 22, Step A, the similar process afforded the title compound in 42% yield, as pale solid. $^1$H-NMR (CDCl$_3$) 10.02 (s, 1H); 7.90 (d, 2H, J=8.22 Hz); 7.70 (d, 2H, J=8.22 Hz); 7.51 (d, 1H, J=2.31 Hz); 7.46 (dd, 1H, J=8.4-2.3 Hz); 6.95 (d, 1H, J=8.4 Hz); 3.88 (s, 3H); 2.14 (b, 6H); 2.07 (b, 3H); 1.8 (b, 6H).

Step D: Methyl-1-3'-(1-adamantyl)4'methoxybiphenyl-4-yl)methyl)azetidine-3-carboxylate: When the product of Step C and azatadine 3 methylcarboxylate hydrochloride were substituted for 4-(5-(((4-fluorophenyl)) isopropyl) amino)methyl)thiophen-2-yl)benzaldehyde and sarcosine hydrochloride, respectively in Example 22, Step C, the similar procedure afforded the title compound in 82% yield, as pale paste. $^1$H-NMR (CDCl$_3$) 7.48 (d, 2H, J=8.16 Hz); 7.42 (d, 1H, J=2.3 Hz); 7.37 (dd, 1H, J=8.4-2.3 Hz); 7.28 (d, 2H, J=8.15 Hz); 6.91 (d, 1H, J=8.4 Hz); 3.85 (s, 3H); 3.7 (s, 3H); 3.62 (s, 2H); 3.56-3.52 (m, 2H); 3.35-3.31 (m, 3H); 2.13 (b, 5H); 2.06 (b, 3H); 1.77 (b, 5H); 1.65 (b, 2H).

Step E: 3'-(1-Admantanyl)-4-methoxybiphenyl-4-yl)methyl)azetidine-3-carboxylic acid: When the product of Step D was substituted for methyl-1-(4-((5-chlorobenzofuran-3-yl) methoxy)benzyl)azetidine-3-carboxylate in Example 25, Step E, the similar procedure afforded title compound in 37% yield, as creamy solid. $^1$H-NMR (CDCl$_3$+CD$_3$OD) 7.53 (broad s, 4H); 7.36 (d, 1H, J=2.1 Hz); 7.31 (broad d, 1H, J=8.35 Hz); 6.87 (d, 2H, J=8.47 Hz); 4.3 (s, 2H); 4.19-4.15 (m, 4H); 3.81 (s, 3H); 3.54-3.51 (m, 1H); 2.07-2.00 (m, 9H); 1.73-1.71 (m, 6H).

Example 32

1-(4-(3-(1-Admantnyl)-4-methoxybenzyloxy)benzyl) azetidine-3-carboxylic acid

Step A: 3-(1-Admantanyl)-4-methoxybenzaldehyde: When 4-hydroxybenzaldehyde was substituted for 4-bromophenol in Example 31, Step A, the similar procedure afforded 3-(1-admantanyl)-4-hydroxybenzaldehyde in 56% yield, as a pale white solid. $^1$H-NMR (CDCl$_3$) 9.84 (s, 1H); 7.78 (d, 1H, J=2.07 Hz); 7.61 (dd, 1H, J=8.13, 2.01 Hz); 6.77 (d, 1H, J=8.16 Hz); 5.88 (bs, 1H); 2.12 (s, 6H); 2.09 (s, 3H); 1.78 (s, 6H). This was methylated by similar procedure as described in Example 31, Step B, to give the title compound in 64% yield, as light yellow solid. $^1$H-NMR (CDCl$_3$) 9.86 (s, 1H); 7.76 (d, 1H, J=2.07 Hz); 7.7 (dd, 1H, J=8.4, 2.1 Hz); 6.95 (d, 1H, J=8.4 Hz); 3.91 (s, 3H); 2.09 (s, 9H); 1.76 (s, 6H).

Step B: 4-(3-(1-Admantnyl)-4-methoxybenzyloxy)benzaldehyde: To a stirred suspension of product of Step A (0.09 g, 0.32 mmol) in MeOH (5 ml) NaBH$_4$ (0.018 g, 0.47 mmol) was added and the mixture was stirred for 0.5 h. The solvent was evaporated to dryness and the residue was taken in NaHCO$_3$ solution and extracted with EtOAc (25 ml). The organic layer was separated, dried over MgSO$_4$, and filtered. The filtrate was evaporated and the residue was dried in vacuo to give a relevant benzyl alcohol (0.095 g; 100%), as a creamy gum. $^1$H-NMR (CDCl$_3$) 7.21 (d, 1H, J=2.17 Hz); 7.16 (dd, 1H, J=8.21, 2.17 Hz); 6.83 (d, 1H, J=8.21 Hz); 4.59 (bd, 2H, J=4.24 Hz); 3.82 (s, 3H, OMe); 2.08 (s, 6H); 2.05 (s, 3H); 1.76 (s, 6H). To a stirred solution of above product in anhydrous CH$_2$Cl$_2$ (5 ml) CBr$_4$ (0.14 g, 0.42 mmol) was added, followed by PPh$_3$ (0.11 g, 0.42 mmol). The mixture was stirred for 1 h at room temperature and the solvent was distilled off. The residue was taken in EtOAc (10 ml) and the insoluble material was filtered off. The filtrate was evaporated to give the relevant benzyl bromide (0.14 g), which was added as a solution in DMF (2 ml) to a stirred suspension of 4-hydroxybenzaldehyde (0.069 g, 0.57 mmol) and K$_2$CO$_3$ (0.080 g, 0.58 mmol) in anhydrous DMF (3 ml) and this was stirred for 2 h at 70° C. The mixture was quenched with saturated NR$_4$Cl solution and extracted with EtOAc (50 ml). The organic layer was dried over MgSO$_4$ and filtered. The filtrate was evaporated to dryness and the residue was purified by FCC (SiO$_2$, hexane/ EtOAc) to give the title compound (0.05 g, 31.4%), as colourless solid. $^1$H-NMR (CDCl$_3$) 9.88 (5, 1H); 7.82 (d, 2H, J=8.78 Hz); 7.26-7.21 (m, 3H); 7.01 (d, 2H, J=8.7 Hz); 6.87 (d, 1H, J=8.2 Hz); 5.04 (s, 2H); 3.83 (s, 3H); 2.08 (s, 6H); 2.05 (s, 3H); 1.76 (s, 6H).

Step C: Methyl 1-(4-(3-(1-adamantyl)-4-methoxybenzyloxy)benzyl)azetidine-3-carboxylate: When the product of Step B and azatadine 3 methylcarboxylate hydrochloride were substituted for 4-(5-(((4-fluorophenyl))-isopropyl) amino)methyl)thiophen-2-yl)benzaldehyde and sarcosine hydrochloride, respectively, in Example 22, Step C, the similar procedure afforded the title compound in 69% yield, as a pale paste. $^1$H-NMR (CDCl$_3$) 7.24-7.20 (m, 2H); 7.16 (d, 2H, J=8.55 Hz); 6.91 (d, 2H, J=8.62 Hz); 6.85 (d, 1H, J=8.17 Hz); 4.92 (s, 2H); 3.82 (s, 3H); 3.69 (s, 3H); 3.52 (s, 2H); 3.49 (s, 1H); 3.47 (s, 2H); 3.31-3.24 (m, 3H); 2.08 (s, 6H); 2.04 (s, 3H); 1.75 (s, 6H).

Step D: 1-(4-(3-(1-Admantnyl)-4-methoxybenzyloxy) benzyl)azetidine-3-carboxylic acid: When the product of Step C was substituted for methyl-1-(4-((5-chlorobenzofuran-3-yl)methoxy)benzyl)azetidine-3-carboxylate in Example 25, Step E, the similar procedure afforded the title compound in 61% yield, as creamy solid. $^1$H-NMR (CDCl$_3$: CD$_3$OD) 7.33 (d, 2H, J=8.59 Hz); 7.17-7.12 (m, 2H); 6.92 (d, 2H, J=8.64 Hz); 6.79 (d, 1H, J=8.21 Hz); 4.87 (s, 2H); 4.13 (s, 2H); 4.08-4.02 (m, 4H); 2.0 (s, 6H); 1.97 (s, 3H); 1.68 (s, 6H).

Example 33

1-(4-(2-(6,6-Dimethylbicyclo[3.1.1]heptan-2-yl) ethoxy)benzyl)azetidine-3-carboxylic acid Step A: 4-(2-(6,6-Dimethylbicyclo[3.1.1]heptan-2-yl) ethoxy)benzaldehyde: (6,6-Dimethylbicyclo[3.1.1]hept-2-en-2-yl)ethanol was brominated as described in Example 32, Step B and the bromination product was used in next step without further purification, where it was treated with 4-hydroxybenzaldehyde as described in Example 32, Step B to afford the title compound in 91% yield, as creamy paste.

Step B: Methyl-1-(4-(2-(6,6-dimethylbicyclo[3.1.1]heptan-2-yl)ethoxy)benzyl)azetidine-3-carboxylate: When the product of Step A and azatadine 3 methylcarboxylate hydrochloride were substituted for 4-(5-(((4-fluorophenyl))-isopropyl)amino)methyl)thiophen-2-yl)benzaldehyde and sarcosine hydrochloride, respectively, in Example 22, Step C, the similar procedure afforded the title compound in 76% yield, as light yellow paste. $^1$H-NMR (CDCl$_3$) 7.17 (d, 2H, J=8.56 Hz); 6.81 (d, 2H, J=8.61 Hz); 3.91 (t, 2H, J=1.98 Hz); 3.71-3.65 (m, 7H); 3.44-3.41 (m, 3H); 2.03-1.17 (m, 10H); 1.17 (s, 3H); 1.01 (s, 3H).

Step C: 1-(4-(2-(6,6-Dimethylbicyclo[3.1.1]heptan-2-yl)ethoxy)benzyl) azetidine-3-carboxylic acid: When the product of Step B was substituted for methyl-1-(4-((5-chlorobenzofuran-3-yl)methoxy)benzyl)azetidine-3-carboxylate in Example 25, Step E, the similar procedure afforded the title compound in 87% yield, as creamy paste. $^1$H-NMR (CDCl$_3$+ CD$_3$OD) 7.21 (d, 2H, J=7.98 Hz); 6.79 (d, 2H, J=7.99 Hz); 3.94-3.71 (m, 8H); 3.27-3.25 (m, 1H); 2.36-1.20 (m, 10H); 1.14 (s, 3H); 0.97 (s, 3H).

Example 34

1-(4-(12-Oxo-12H-chromeno[2,3-b]quinolin-2-yl)benzyl)azetidine-3-carboxylic acid Step A: 6-Bromo-4-oxo-2-(phenylamino)-4H-chromene-3-carbaldehyde: To a stirred solution of 6-bromo-4-oxo-4H-chromene-3-carbaldehyde (2 g, 7.93 mmol) in anhydrous benzene (15 ml) phenyl-hydroxylamine (0.95 g, 8.71 mmol) was added. The solution was kept for 1 h at room temperature when the crystalline solid appeared. To this glacial AcOH (0.5 ml) was added and the mixture was stirred for 5 h at reflux. The solvent was distilled off and the residue was crystallized from MeOH to give the title compound (2.1 g, 78%), as yellow crystalline solid. $^1$H-NMR (CDCl$_3$) 12.43 (broad s, 1H); 10.28 (s, 1H); 8.34 (d, 1H, J=2.46 Hz); 7.69 (dd, 1H, J=8.76, 2.49 Hz); 7.46-7.29 (m, 6H).

Step B: 2-Bromo-12H-chromeno[2,3-b]quinolin-12-one: To the product of Step A (1 g; 2.92 mmol) concentrated H$_2$SO$_4$ (1 ml) was gently added with stirring. The mixture was kept in sealed vial for 24 h, at room temperature, than poured onto ice water and extracted with CH$_2$Cl$_2$ (50 ml). The organic layer was washed with NaHCO$_3$ solution, H$_2$O, dried over MgSO$_4$ and filtered. The filtrate was distilled off and the residue was crystallized from CH$_3$CN to give the title compound (0.73 g, 77%), as green yellow solid. $^1$H-NMR (CDCl$_3$) 9.28 (s, 1H); 8.44 (d, 1H, J=2.1 Hz); 8.1-8.06 (m, 2H); 7.94-7.84 (m, 2H); 7.63 (t, 1H, J=7.88 Hz); 7.51 (d, 1H, J=8.83 Hz).

Step C: 4-(12-Oxo-12H-chromeno[2,3-b]quinolin-2-yl)benzaldehyde: When the product of Step B and 4-carbaldehyde-boronic were substituted for 4-bromobenzaldehyde and 5-(hydroxymethyl)thiophen-2-ylboronic acid, respectively, in Example 22, Step A, the similar procedure afforded the title compound in 52% yield, as off white solid. $^1$H-NMR (CDCl$_3$) 10.08 (s, 1H); 9.33 (s, 1H); 8.6 (d, 1H, J=2.34 Hz); 8.14-8.05 (m, 3H); 8.00 (d, 2H, J=8.25 Hz); 7.96-7.89 (m, 1H); 7.85 (d, 2H, J=8.22 Hz); 7.74 (d, 1H, J=8.7 Hz); 7.64 (t, 1H, J=7.8 Hz).

Step D: Methyl-1-(4-(12-oxo-12H-chromeno[2,3-b]quinolin-2-yl)benzyl) azetidine-3-carboxylate: When the product of Step C and azatadine 3 methylcarboxylate hydrochloride were substituted for 4-(5-(((4-fluorophenyl))isopropyl)amino)methyl) thiophen-2-yl)benzaldehyde and sarcosine hydrochloride, respectively, in Example 22, Step C, the similar procedure afforded the title compound in 48% yield, as pale paste. $^1$H-NMR (CDCl$_3$) 9.32 (s, 1H); 8.53 (s, 1H); 8.12-8.07 (m, 2H); 8.00 (dd, 1H, J=8.7, 2.4 Hz); 7.91 (t, 1H, J=5.55 Hz); 7.7-7.6 (m, 4H); 7.38 (d, 2H, J=8.22 Hz); 3.71 (s, 3H); 3.67 (s, 2H); 3.57-3.53 (m, 2H); 3.39-3.35 (m, 3H).

Step E: 1-(4-(12-Oxo-12H-chromeno[2,3-b]quinolin-2-yl)benzyl)azetidine-3-carboxylic acid: When the product of Step D was substituted for methyl-1-(4-((5-chlorobenzofuran-3-yl)methoxy)benzyl)azetidine-3-carboxylate in Example 25, Step E, the similar procedure afforded the title compound in 50% yield, as yellow solid. $^1$H-NMR (CDCl+ CD$_3$OD) 9.25 (broad s, 1H); 8.44 (m, 2H); 7.76-7.54 (m, 5H); 4.31-4.07 (m, 4H); 4.27-3.95 (m, 2H).

Example 35

1-(4-((5-chlorobenzofuran-3-yl)methoxy)benzyl) azetidine-3-carboxylic acid

Step A: (5-Chlorobenzofuran-3-yl)methanol: To a mixture of 4-chloro-2-iodophenol (1 g, 3.92 mmol), tert-butyl(3-(tert-butyldimethylsilyl)prop-2-ynyloxy)-dimethylsilane (1.93 g, 6.8 mmol), LiCl (0.15 g; 3.5 mmol) and Na$_2$CO$_3$ (0.636 g; 6 mmol) in anhydrous DMF (10 ml) Pd(OAc)$_2$ (0.3 g) was added at 100° C. under N$_2$ and heating was continued for 1.5 h. The solvent was removed in vacuo and the residue was diluted to 100 ml with EtOAc, washed with H$_2$O, dried over MgSO$_4$ and filtered. The filtrate was evaporated to dryness and the residue was purified by FCC (SiO$_2$, hexane/EtOAc) to give the coupling product (0.64 g; 26%). This was dissolved in THF (5 ml) and 1M TBAF in THF (2 ml) was added to it and the mixture was stirred for 4 h at reflux. The solvent was distilled off and the residue was dilute to 50 ml with EtOAc, washed with 1M HCl, H$_2$O, dried over MgSO$_4$ and filtered. The filtrate was evaporated to dryness and the residue was purified by FCC (SiO$_2$, hexane/EtOAc) to give the title compound (0.33 g; 99%), as creamy paste. $^1$H-NMR (CDCl$_3$) 7.63 (d, 1H, J=2.11 Hz); 6.60 (b, 1H); 7.37 (d, 1H, J=8.72 Hz); 7.25 (dd, 1H, J=8.71, 2.13 Hz); 4.79 (s, 2H).

Step B: 4-((5-Chlorobenzofuran-3-yl)methoxy)benzaldehyde: When the product of Step A was substituted for 3-(1-admantanyl)-4-methoxy benzaldehyde in Example 32, Step B, the similar procedure afforded the title compound in 9% yield, as pale paste. $^1$H-NMR (CDCl$_3$) 9.89 (s, 1H); 7.84 (d, 2H, J=8.74 Hz); 7.72 (s, 1H); 7.60 (d, 1H, J=2.07 Hz); 7.41 (d, 1H, J=8.76 Hz); 7.28 (dd, 1H, J=8.75, 2.09 Hz); 7.09 (d, 2H, J=8.73 Hz); 5.23 (s, 2H).

Step C: Methyl-1-(4-((5-chlorobenzofuran-3-yl)methoxy)benzyl)azetidine-3-carboxylate: When the product of Step B and azatadine 3-methylcarboxylate hydrochloride were substituted for 4-(5-(((4-fluorophenyl)(isopropyl)amino)methyl)-thiophen-2-yl)benzaldehyde and sarcosine hydrochloride, respectfully, in Example 22, Step C, the similar procedure afforded the title compound in 45% yield, as off white solid. $^1$H-NMR (CDCl$_3$) 7.68 (s, 1H); 7.60 (bs, 1H); 7.39 (d, 2H, J=8.77 Hz); 7.28-7.18 (m, 3H); 6.93 (d, 2H, J=6.62 Hz); 5.12 (s, 2H); 3.69 (s, 3H); 3.54-3.47 (m, 5H); 3.36-3.28 (m, 4H).

Step D: 1-(4-((5-chlorobenzofuran-3-yl)methoxy)benzyl) azetidine-3-carboxylic acid: When the product of Step C was substituted for methyl-1-(4-((5-chlorobenzofuran-3-yl)methoxy)benzyl)azetidine-3-carboxylate in Example 25, Step E), the similar procedure afforded the title compound in 57% yield, as creamy solid. $^1$H-NMR (CDCl$_3$+CD$_3$OD) 7.78

(s, 1H); 7.57 (d, 2H, J=2.06 Hz); 7.53 (s, 1H); 7.39 (d, 1H, J=8.8 Hz); 7.36 (d, 2H, J=8.66 Hz); 7.24 (dd, 1H, J=8.75, 2.12 Hz); 7.04 (d, 2H, J=8.67 Hz); 5.18 (s, 2H); 4.20-4.06 (m, 6H); 3.36-3.27 (m, 1H).

Example 36

2-Amino-2-(5-(5-(3-chloro-4-propoxyphenyl)-1,2,4-oxadiazol-3-yl)benzofuran-2-yl)propane-1,3-diol Step A: N-Hydroxy-3-iodo-4-isopropoxybenzimidamide: A suspension of 3-iodo-4-isopropoxybenzonitrile (0.576 g; 2 mmol), HCl×NH$_2$OH (0.276 g; 4 mmol) and DIPEA (0.69 ml; 4 mmol) in EtOH (50 ml) was stirred for 18 h at 50° C. The solvent was distilled off and the residue was diluted to 50 ml with EtOAc and washed with H$_2$O. The organic layer was separated, dried over MgSO$_4$ and filtered. The filtrate was distilled off to give the title product (0.61 g; 95%), as colourless solid. $^1$H-NMR (CDCl$_3$) 8.0 (d, 1H, J=2.22 Hz); 7.55 (dd, 1H, J=9.54, 2.28 Hz); 6.77 (d, 1H, J=8.7 Hz); 4.95 (b, 2H); 4.69-4.63 (m, 1H); 1.42 (d, 6H).

Step B: 5-(3-Chloro-4-propoxyphenyl)-3-(3-iodo-4-isopropoxyphenyl)-1,2,4-oxadiazole: A mixture of 3-chloro-4-propoxybenzoic acid (0.298 g, 0.93 mmol), the product of Step A (0.2 g, 0.93 mmol) and EDC (0.214 g, 1.1 mmol) in anhydrous DMF (3 ml) was stirred overnight at 45° C. 1M TBAF in THF (0.3 ml) was added and this was stirred for 2.5 h at 110° C. The reaction mixture was diluted to 20 ml with H$_2$O and extracted with EtOAc (2×15 ml). The organic layer was separated, dried over MgSO$_4$ and filtered. The filtrate was distilled off and the residue was purified by FCC (SiO$_2$, hexane/EtOAc) to give the title compound (0.22 g, 47.4%), as a colourless solid. $^1$H-NMR (CDCl$_3$) 8.56 (d, 1H, J=2.04 Hz); 8.21 (d, 1H, J=2.37 Hz); 8.07-8.02 (m, 2H); 7.00 (d, 1H, J=8.73 Hz); 6.87 (d, 1H, J=8.67 Hz); 4.68-4.63 (m, 1H); 4.08 (t, 2H, J=6.45 Hz); 1.93-1.87 (m, 2H); 1.36 (d, 6H, J=6.06 Hz); 1.09 (t, 3H, J=7.44 Hz).

Step C: 4-(5-(3-Chloro-4-propoxyphenyl)-1,2,4-oxadiazol-3-yl)-2-iodophenol: To a solution of the product of Step B (0.2 g, 0.4 mmol) in anhydrous CH$_2$Cl$_2$ (2 ml) 1M BCl$_3$ in CH$_2$Cl$_2$ (3 ml) was added drop wise at rt. After 1 h, more of 1M BCl$_3$ in CH$_2$Cl$_2$ (1 ml) was added and this was stirred for 1 h. The reaction mixture was quenched with saturated NH$_4$Cl solution and extracted with CH$_2$Cl$_2$ (20 ml). The organic layer was separated, dried over MgSO$_4$ and filtered. The filtrates was evaporated to dryness and the residue was crystallized from MeOH to give the title compound (0.145 g, 79%), as colourless solid. $^1$H-NMR (CDCl$_3$) 8.47 (d, 1H, J=1.95 Hz); 8.21 (d, 1H, J=2.1 Hz); 8.06-8.04 (m, 1H); 8.03-8.02 (m, 1H); 7.07 (d, 1H, J=8.49 Hz); 7.00 (d, 1H, J=8.7 Hz); 4.08 (t, 2H, J=6.45 Hz); 1.94-1.87 (m, 2H); 1.09 (t, 3H, J=7.44 Hz).

Step D: tert-Butyl 5-(5-(5-(3-chloro-4-propoxyphenyl)-1,2,4-oxadiazol-3-yl)benzofuran-2-yl)-2,2-dimethyl-1,3-dioxan-5-ylcarbamate: A solution of the product of Step C (0.1 g; 0.22 mmol) and tert-butyl 5-ethynyl-2,2-dimethyl-1,3-dioxan-5-ylcarbamate (0.056 g; 0.22 mmol) in a mixture of DMF and DIPEA (3 ml: 0.3 ml) was degassed with N$_2$ and Cl$_2$Pd(PPh$_3$)$_4$ (0.025 g) was added, followed by catalytic amount of CuI. The mixture was stirred overnight at 45° C. under N$_2$, diluted to 20 ml with saturated NH$_4$Cl and extracted with EtOAc (40 ml). The organic layer was separated, dried over MgSO$_4$ and filtered. The filtrate was distilled off and the residue was purified by FCC (SiO$_2$, hexane/EtOAc) to give the title compound (0.11 g, 78%), as pale paste. $^1$H-NMR (CDCl$_3$) 8.34 (d, 1H, J=1.29 Hz); 8.24 (d, 1H, J=2.13 Hz); 8.08 (t, 1H, J=1.56 Hz); 8.05 (t, 1H, J=1.56 Hz); 7.53 (d, 1H, J=8.67 Hz); 7.03 (d, 1H, J=8.67 Hz); 6.75 (s, 1H); 4.26-4.19 (m, 4H); 4.06 (t, 2H, J=5.49 Hz); 1.94-1.87 (m, 2H); 1.41 (s, 9H); 1.36 (s, 6H); 1.1 (t, 3H, J=7.44 Hz).

Step E: 2-Amino-2-(5-(5-(3-chloro-4-propoxyphenyl)-1,2,4-oxadiazol-3-yl)benzofuran-2-yl)propane-1,3-diol: To a stirred solution of product of Step D (0.1 g, 0.17 mmol) in CH$_2$Cl$_2$ (0.5 ml) TFA (1 ml) was added. After stirring for 1 h at room temperature, EtOH (2 ml) was added and stirring was continued for additional 1 h. The mixture was evaporated to dryness and the residue was purified by FCC (SiO$_2$, CH$_2$Cl$_2$ saturated with concentrated NH$_4$OH/MeOH; 98:2) to give the title product (0.035 g, 46%) as colourless solid. $^1$H-NMR (DMSO-d$_6$) 8.3 (d, 1H, J=1.11 Hz); 8.15 (d, 1H, J=2.01 Hz); 8.09 (dd, 1H, J=8.67, 2.04 Hz); 7.94 (dd, 1H, J=8.58, 1.53 Hz); 7.68 (d, 1H, J=8.61 Hz); 7.37 (d, 1H, J=8.76 Hz); 6.92 (s, 1H); 4.91 (b, 2H); 4.14 (t, 2H, J=6.36 Hz); 3.69 (d, 2H, J=10.6 Hz); 3.59 (d, 2H, J=10.6 Hz); 1.83-1.72 (m, 2H); 0.97 (t, 3H, J=7.41 Hz).

Example 37

(E)-2-Amino-2-(5-(5-(4-methylstyryl)-1,2,4-oxadiazol-3-yl)benzofuran-2-yl)propane-1,3-diol Step A: (E)-3-(3-Iodo-4-isopropoxyphenyl)-5-(4-methylstyryl)-1,2,4-oxadiazole: When (E)-3-p-tolylacrylic acid was substituted for 3-chloro-4-propoxybenzoic acid in Example 36, Step B, the similar process afforded the title compound in 52% yield, as colourless solid. $^1$H-NMR (CDCl$_3$) 8.53 (d, 1H, J=2.07 Hz); 8.01 (dd, 1H, J=8.58, 2.1 Hz); 7.82 (d, 1H, J=16.35 Hz); 7.49 (d, 1H, J=8.1 Hz); 6.97 (d, 1H, J=16.38 Hz); 6.87 (d, 1H, J=8.76 Hz); 4.69-4.6 (m, 1H); 1.4 (d, 6H, J=5.85 Hz).

Step B. (E)-2-Iodo-4-(5-(4-methylstyryl)-1,2,4-oxadiazol-3-yl)phenol: When the product of Step A was substituted for 5-(3-chloro-4-propoxyphenyl)-3-(3-iodo-4-isopropoxyphenyl)-1,2,4-oxadiazole in Example 36, Step C, the similar procedure afforded the title compound in 53% yield, as colourless solid. $^1$H-NMR (CDCl$_3$) 8.44 (d, 1H, J=1.95 Hz); 8.0 (dd, 1H, J=8.49, 2.01 Hz); 7.84 (d, 1H, J=16.35 Hz); 7.49 (d, 1H, J=8.16 Hz); 7.07 (d, 1H, J=8.49 Hz); 6.98 (d, 1H, J=16.83 Hz); 5.61 (s, 1H).

Step C: (E)-tert-Butyl 2,2-dimethyl-5-(5-(5-(4-methylstyryl)-1,2,4-oxadiazol-3-yl)benzofuran-2-yl)-1,3-dioxan-5-ylcarbamate: When the product of Step B was substituted for 4-(5-(3-chloro-4-propoxy phenyl)-1,2,4-oxadiazol-3-yl)-2-iodophenol in Example 36, Step D, the similar process afforded the title compound in 68% yield, as pale paste. $^1$H-NMR (CDCl$_3$) 8.30 (d, 1H, J=1.32 Hz); 8.03 (dd, 1H, J=8.61, 1.68 Hz); 7.84 (d, 1H, J=16.38 Hz); 7.53-7.49 (m, 3H); 7.21 (d, 2H, J=5.34 Hz); 7.0 (d, 1H, J=15.15 Hz); 5.28 (s, 1H); 4.24 (b, 4H); 2.39 (s, 3H); 1.46-1.39 (m, 15H).

Step D: (E)-2-Amino-2-(5-(5-(4-methylstyryl)-1,2,4-oxadiazol-3-yl)benzofuran-2-yl)propane-1,3-diol: When the product of Step C was substituted for tert-butyl 5-(5-(5-(3-chloro-4-propoxyphenyl)-1,2,4-oxadiazol-3-yl)benzofuran-2-yl)-2,2-dimethyl-1,3-dioxan-5-yl carbamate in Example 36, Step E, the similar procedure afforded the title compound in 48% yield, as colourless solid. $^1$H-NMR (DMSO-d$_6$) 8.23 (b, 1H); 7.9-7.85 (m, 2H); 7.72-7.64 (m, 3H); 7.33 (d, 1H, J=16.2 Hz); 7.25 (d, 2H, J=6.3 Hz); 6.87 (s, 1H); 4.77 (b, 2H); 3.63 (b, 2H); 3.56 (b, 2H); 2.32 (s, 3H); 1.95 (b, 2H).

Example 38

2-Amino-2-(5-(5-(4-bromo-3-chlorophenyl)-1,2,4-oxadiazol-3-yl)benzofuran-2-yl)propane-1,3-diol Step A: 5-(4-Bromo-3-chlorophenyl)-3-(3-iodo-4-isopropoxyphenyl)-1,2,4-oxadiazole: When 4-bromo-3-chlorobenzoic acid was substituted for 3-chloro-4-propoxybenzoic acid in Example 36, Step B, the similar procedure afforded the title compound in 72% yield, as creamy solid. ¹H-NMR (CDCl₃) 8.55 (d, 1H, J=2.07 Hz); 8.27 (d, 1H, J=1.89 Hz); 8.04 (dd, 1H, J=8.61, 2.04 Hz); 7.91 (dd, 1H, J=8.34, 1.95 Hz); 7.79 (d, 1H, J=8.37 Hz); 6.87 (d, 1H, J=8.67 Hz); 4.7-4.6 (m, 1H); 1.4 (d, 6H, J=5.94 Hz).

Step B: 4-(5-(4-Bromo-3-chlorophenyl)-1,2,4-oxadiazol-3-yl)-2-iodophenol: When the product of Step A was substituted for 5-(3-chloro-4-propoxyphenyl)-3-(3-iodo-4-isopropoxyphenyl)-1,2,4-oxadiazole in Example 36, Step C, the similar procedure afforded the title compound in 86% yield, as creamy solid. ¹H-NMR (CDCl₃) 8.47 (d, 1H, J=1.98 Hz); 8.28 (d, 1H, J=1.95 Hz); 8.03 (dd, 1H, J=8.49, 1.98 Hz); 7.92 (dd, 1H, J=8.37, 1.98 Hz); 7.84 (d, 1H, J=8.37 Hz); 7.08 (d, 1H, J=8.52 Hz); 5.65 (b, 1H).

Step C: tert-Butyl 5-(5-(5-(4-bromo-3-chlorophenyl)-1,2,4-oxadiazol-3-yl)benzofuran-2-yl)-2,2-dimethyl-1,3-dioxan-5-ylcarbamate: When the product of Step B was substituted for 4-(5-(3-chloro-4-propoxyphenyl)-1,2,4-oxadiazol-3-yl)-2-iodophenol in Example 36, Step D, the similar procedure afforded the title compound in 58% yield, as pale paste. ¹H-NMR (CDCl₃) 8.34 (d, 1H, J=1.53 Hz); 8.31 (d, 1H, J=1.95 Hz); 8.06 (dd, 1H, J=8.61, 1.68 Hz); 7.94 (dd, 1H, J=8.37, 1.98 Hz); 7.8 (d, 1H, J=8.37 Hz); 7.54 (d, 1H, J=8.61 Hz); 6.76 (s, 1H); 5.34 (bs, 1H); 4.3-4.24 (m, 4H); 1.55 (s, 9H); 1.47 (s, 6H).

Step D: 2-Amino-2-(5-(5-(4-bromo-3-chlorophenyl)-1,2,4-oxadiazol-3-yl)benzofuran-2-yl)propane-1,3-diol: When the product of Step C was substituted for tert-butyl 5-(5-(5-(3-chloro-4-propoxyphenyl)-1,2,4-oxadiazol-3-yl)benzofuran-2-yl)-2,2-dimethyl-1,3-dioxan-5-ylcarbamate in Example 36, Step E, the similar procedure afforded the title compound in 39% yield, as creamy solid. ¹H-NMR (DMSO-d₆) 8.31 (b, 2H); 8.05 (d, 1H, J=8.52 Hz); 8.00 (d, 1H, J=8.49 Hz); 7.94 (d, 1H, J=8.58 Hz); 7.68 (d, 1H, J=8.46 Hz); 6.91 (s, 1H); 4.88 (bs, 1H); 3.66 (bs, 2H); 3.58 (bs, 2H).

Example 39

2-Amino-2-(5-(5-(3-chloro-4-(thiophen-3-yl)phenyl)-1,2,4-oxadiazol-3-yl)benzofuran-2-yl)propane-1,3-diol Step A: tert-Butyl 5-(5-(5-(3-chloro-4-(thiophen-3-yl)phenyl)-1,2,4-oxadiazol-3-yl)benzofuran-2-yl)-2,2-dimethyl-1,3-dioxan-5-ylcarbamate: To a stirred mixture of the product of Example 38, Step C (0.09 g, 0.15 mmol) and 3-thiopheneboronic acid (0.028 g, 0.22 mmol) in a mixture of dioxane and H₂O (5 ml:1 ml), Pd(PPh₃)₄ (0.03 g) was added at 80° C., followed by the NaHCO₃ solution (0.065 g in 1 ml H2O) and this was stirred for 2 h. The solvent was distilled off and the residue was diluted to 20 ml with EtOAc, washed with H₂O, dried over MgSO₄ and filtered. The filtrate was evaporated and the residue was purified by FCC (SiO₂, hexane/EtOAc), to give the title compound (0.065 g, 71%), as pale paste. ¹H-NMR (CDCl₃) 8.45 (d, 1H, J=1.53 Hz); 8.25-8.22 (m, 2H); 7.94 (dd, 1H, J=8.7, 1.8 Hz); 7.55-7.42 (m, 3H); 7.38-7.37 (m, 2H); 6.78 (s, 1H); 5.43 (bs, 1H); 4.29-4.13 (m, 4H); 1.46 (s, 9H); 1.27 (b, 6H).

Step B: 2-Amino-2-(5-(5-(3-chloro-4-(thiophen-3-yl)phenyl)-1,2,4-oxadiazol-3-yl)benzofuran-2-yl)propane-1,3-diol: When the product of Step A was substituted for tert-butyl 5-(5-(5-(3-chloro-4-propoxyphenyl)-1,2,4-oxadiazol-3-yl)benzofuran-2-yl)-2,2-dimethyl-1,3-dioxan-5-ylcarbamate in Example 36, Step E, the similar procedure afforded the title compound in 48% yield, as colourless solid. ¹H-NMR (DMSO-d₆) 8.42 (s, 1H); 8.28 (s, 1H); 8.2 (d, 1H, J=8.41 Hz); 8.11 (d, 1H, J=8.1 Hz); 7.82 (s, 1H); 7.64-7.61 (m, 3H); 7.4 (b, 1H); 6.92 (s, 1H); 4.9 (bs, 2H); 3.66 (b, 2H); 3.59 (b, 2H).

Example 40

2-Amino-2-(5-(5-(3,4-diethoxyphenyl)-1,2,4-oxadiazol-3-yl)benzofuran-2-yl)propane-1,3-diol Step A: 5-(3,4-Diethoxyphenyl)-3-(3-iodo-4-isopropoxyphenyl)-1,2,4-oxadiazole: When 3,4-diethoxy benzoic acid was substituted for 3-chloro-4-propoxybenzoic acid in Example 36, Step B, the similar procedure afforded the title compound in 60% yield, as colourless solid. ¹H-NMR (CDCl₃) 8.57 (d, 1H, J=2.05 Hz); 8.05 (dd, 1H, J=8.58, 2.03 Hz); 8.02 (d, 1H, J=2.07 Hz); 7.76 (dd, 1H, J=8.41, 1.94 Hz); 7.66 (d, 1H, J=1.93 Hz); 6.96 (d, 1H, J=8.5 Hz); 6.87 (d, 1H, J=8.69 Hz); 4.67-4.63 (m, 1H); 4.24-4.14 (m, 4H); 1.53-1.4 (m, 6H); 1.38 (d, 6H, J=6.64 Hz).

Step B: 4-(5-(3,4-Diethoxyphenyl)-1,2,4-oxadiazol-3-yl)-2-iodophenol: When the product of Step A was substituted for 5-(3-chloro-4-propoxyphenyl)-3-(3-iodo-4-isopropoxyphenyl)-1,2,4-oxadiazole in Example 36, Step C, the similar procedure afforded the title compound in 84% yield, as a creamy solid. ¹H-NMR (CDCl₃) 8.48 (d, 1H, J=2.05 Hz); 8.04 (dd, 1H, J=8.46, 1.98 Hz); 7.76 (dd, 1H, J=8.43, 2.0 Hz); 7.65 (d, 1H, J=1.98 Hz); 7.07 (d, 1H, J=8.5 Hz); 6.96 (d, 1H, J=8.46 Hz); 5.63 (bs, 1H); 4.24-4.09 (m, 4H); 1.56-1.42 (m, 6H).

Step C: tert-Butyl 5-(5-(5-(3,4-diethoxyphenyl)-1,2,4-oxadiazol-3-yl)benzofuran-2-yl)-2,2-dimethyl-1,3-dioxan-5-ylcarbamate: When the product of Step B was substituted for 4-(5-(3-chloro-4-propoxyphenyl)-1,2,4-oxadiazol-3-yl)-2-iodophenol in Example 36, Step D, the similar procedure afforded the title compound in 66% yield, as creamy paste. ¹H-NMR (CDCl₃) 8.35 (d, 1H, J=1.57 Hz); 8.08 (dd, 1H, J=8.62, 1.68 Hz); 7.79 (dd, 1H, J=8.44, 1.94 Hz); 7.69 (d, 1H, J=1.93 Hz); 7.52 (d, 1H, J=8.54 Hz); 6.96 (d, 1H, J=8.5 Hz); 6.75 (s, 1H); 5.32 (b, 1H); 4.36-4.15 (m, 8H); 3.95 (s, 2H); 1.54-1.47 (m, 21H).

Step D: 2-Amino-2-(5-(5-(3,4-diethoxyphenyl)-1,2,4-oxadiazol-3-yl)benzofuran-2-yl)propane-1,3-diol: When the product of Step C was substituted for tert-butyl 5-(5-(5-(3-chloro-4-propoxyphenyl)-1,2,4-oxadiazol-3-yl)benzofuran-2-yl)-2,2-dimethyl-1,3-dioxan-5-yl carbamate in Example 36, Step E, the similar procedure afforded the title compound in 61% yield, as creamy solid. ¹H-NMR (DMSO-d₆) 8.27 (s, 1H); 7.92 (d, 1H, J=8.23 Hz); 7.75-7.61 (m, 3H); 7.17 (d, 1H, J=8.34 Hz); 6.88 (s, 1H); 4.78 (b, 2H); 4.15-4.00 (b, 4H); 3.65-3.64 (b, 2H); 3.57-3.55 (b, 2H); 1.35 (b, 6H).

Example 41

2-Amino-2-(5-(5-(4-propoxy-3-methoxyphenyl)-1,2,4-oxadiazol-3-yl)benzofuran-2-yl)propane-1,3-diol Step A: 5-(4-Propoxy-3-methoxyphenyl)-3-(3-iodo-4-isopropoxyphenyl)-1,2,4-oxadiazole: When 4-propoxy-3-methoxybenzoic acid was substituted for 3-chloro-4-propoxybenzoic acid in Example 36, Step B, the similar procedure afforded the title compound in 58% yield, as creamy solid. ¹H-NMR (CDCl₃) 8.58 (d, 1H, J=2.01 Hz); 8.06 (dd, 1H, J=8.61, 2.07 Hz); 7.77 (dd, 1H, J=8.43, 1.98 Hz); 7.66 (d, 1H, J=1.92 Hz); 6.97 (d, 1H, J=8.46 Hz); 6.88 (d, 1H, J=8.7 Hz); 4.69-4.61 (m, 1H); 4.06 (t, 2H, J=6.81 Hz); 3.98 (s, 3H); 1.93-1.88 (m, 2H); 1.06 (t, 3H, J=7.38 Hz).

Step B: 4-(5-(4-Propoxy-3-methoxyphenyl)-1,2,4-oxadiazol-3-yl)-2-iodophenol: When the product of Step A was substituted for 5-(3-chloro-4-propoxyphenyl)-3-(3-iodo-4-isopropoxyphenyl)-1,2,4-oxadiazole in Example 36, Step C, the similar procedure afforded the title compound in 80% yield, as creamy solid. $^1$H-NMR (CDCl$_3$) 8.48 (d, 1H, J=1.98 Hz); 8.04 (dd, 1H, J=8.46, 1.98 Hz); 7.7 (dd, 1H, J=8.43, 2.01 Hz); 7.65 (d, 1H, J=1.95 Hz); 7.07 (d, 1H, J=8.49 Hz); 6.97 (d, 1H), J=8.46 Hz); 5.63 (s, 1H); 4.06 (t, 2H, J=6.8 Hz); 4.02 (s, 3H); 1.94-1.87 (m, 2H); 1.06 (t, 3H, J=7.41 Hz).

Step C: tert-Butyl 5-(5-(5-(4-propoxy-3-methoxyphenyl)-1,2,4-oxadiazol-3-yl)benzofuran-2-yl)-2,2-dimethyl-1,3-dioxan-5-ylcarbamate: When the product of Step B was substituted for 4-(5-(3-chloro-4-propoxyphenyl)-1,2,4-oxadiazol-3-yl)-2-iodophenol in Example 36, Step D, the similar procedure afforded the title compound in 68% yield, as pale paste. $^1$H-NMR (CDCl$_3$) 8.35 (d, 1H, J=1.23 Hz); 8.08 (dd, 1H, J=8.61, 1.68 Hz); 7.8 (dd, 1H, J=8.41, 1.98 Hz); 7.68 (d, 1H, J=1.92 Hz); 7.52 (d, 1H, J=8.64 Hz); 6.98 (d, 1H, J=8.49 Hz); 6.75 (s, 1H); 5.32 (bs, 1H); 4.26 (b, 4H); 4.06 (t, 2H, J=6.81 Hz); 3.98 (s, 3H); 1.93-1.88 (m, 2H); 1.49 (s, 9H); 1.44 (s, 6H); 1.06 (t, 3H, J=7.38 Hz).

Step D: 2-Amino-2-(5-(5-(4-Propoxy-3-methoxyphenyl)-1,2,4-oxadiazol-3-yl)benzofuran-2-yl)propane-1,3-diol: When the product of Step C was substituted for tert-butyl 5-(5-(5-(3-chloro-4-propoxyphenyl)-1,2,4-oxadiazol-3-yl)benzofuran-2-yl)-2,2-dimethyl-1,3-dioxan-5-ylcarbamate in Example 36, Step E, the similar procedure afforded the title compound in 57% yield, as colourless solid. $^1$H-NMR (DMSO-d$_6$) 8.28 (s, 1H); 7.92 (d, 1H, J=2.82 Hz); 7.61 (m, 3H); 7.16 (d, 1H, J=8.53 Hz); 6.88 (s, 1H); 4.78 (b, 2H); 4.01 (t, 2H, J=6.03 Hz); 3.99 (s, 3H); 3.77-3.57 (m, 4H); 1.78-1.71 (m, 2H); 0.96 (t, 3H, J=7.29 Hz).

Example 42

5-(3,4-Diethoxyphenyl)-3-(2-methylbenzofuran-5-yl)-1,2,4-oxadiazole

Step A: 2-Methylbenzofuran-5-carbonitrile: 2-Iodo-4-cynophenol (0.25 g, 1 mmol) and saccharin (0.1 g) in HMDSA (2 ml) was refluxed for 2 h under N$_2$, until the solution became clear. The solvent was distilled off under reduced pressure and the residue was dissolved in anhydrous THF (2 ml). This was added to a solution made by mixing anhydrous ZnCl$_2$ (0.3 g; 2.2 mmol) with 0.5 M 1-propynyl magnesium bromide in THF (7.8 ml) in anhydrous THF (5 ml) at room temperature under N$_2$. To it, Pd (PPh$_3$)$_4$ (0.15 g) was added at room temperature under N$_2$ followed by catalytic amount of CuI. The mixture was stirred at room temperature for 3 h and quenched with saturated NH$_4$Cl solution. The mixture was diluted to 50 ml with EtOAc and washed with H$_2$O. The organic layer was separated, dried over MgSO$_4$ and filtered. The filtrate was evaporated and the residue was dissolved in 1,4-dioxane (4 ml) and 1M TBAF in THF (0.3 ml) was added and this was stirred for 4 h at reflux. The solvent was distilled off and the residue was purified by FCC (SiO$_2$, hexane/EtOAc) to give the title compound (0.145 g, 91%), as colourless solid. $^1$H-NMR (CDCl$_3$) 7.78 (s, 1H); 7.46-7.44 (m, 2H); 6.41 (bs, 1H); 2.47 (s, 3H).

Step B: 5-(3,4-Diethoxyphenyl)-3-(2-methylbenzofuran-5-yl)-1,2,4-oxadiazole: The product Step A was converted to N-hydroxy-2-methylbenzofuran-5-carboximidamide by method described for Example 36, Step A. When N-hydroxy-2-methylbenzofuran-5-carboximidamide and 3,4-diethoxybenzoic acid were substituted for N-hydroxy-3-iodo-4-isopropoxybenzimidamide and 3-chloro-4-propoxybenzoic acid, respectively, in Example 36, Step B, the similar procedure afforded the title compound in 6% yield, as colourless solid. $^1$H-NMR (CDCl$_3$) 8.28 (bs, 1H); 8.00 (dd, 1H, J=8.55, 1.68 Hz); 7.8 (dd, 1H, J=8.4, 1.98 Hz); 7.68 (d, 1H, J=1.92 Hz); 7.47 (d, 1H, J=8.58 Hz); 6.97 (d, 1H, J=8.46 Hz); 6.45 (s, 1H); 4.23-4.16 (m, 4H); 2.48 (3H); 1.52-1.47 (m, 6H).

Example 43

2-Amino-2-(5-(5-(6-methoxybenzofuran-2-yl)-1,2,4-oxadiazol-3-yl)benzofuran-2-yl)propane-1,3-diol Step A: Ethyl 2-(2-formyl-5-methoxyphenoxy)acetate: A mixture of 2-hydroxy-4-methoxybenzaldehyde (1 g; 6.58 mmol), BrCH$_2$CO$_2$Et (0.806 ml; 7.24 mmol) and K$_2$CO$_3$ (1 g, 7.24 mmol) in anhydrous DMF (5 ml) was stirred overnight at room temperature. The mixture was diluted with EtOAc (100 ml) and H$_2$O (100 ml). The organic layer was separated and dried over MgSO$_4$, and filtrate evaporated, to give the product (1.29 g; 97%), as colourless solid. $^1$H-NMR (CDCl$_3$) 1.28 (tr, 3H, J=7.11 Hz); 3.84 (s, 3H); 4.25 (q, 2H, J=7.14, 14.28 Hz); 4.69 (s, 2H); 6.30 (d, 1H, J=2.16 Hz); 6.58 (dd, 1H, J=1.77, 8.73 Hz); 7.83 (d, 1H, J=8.7 Hz); 10.36 (s, 1H).

Step B: Ethyl 6-methoxybenzofuran-2-carboxylate: A mixture of the product of Step A (1.28 g, 5.37 mmol) and DBU (0.3 ml) was heated for 3 h at 160° C. with stirring, cooled to room temperature and dissolved in EtOAc: MeOH mixture (99:1). The mixture was filtered through the silica bead and the filtrate was evaporated to give the title compound (1.11 g; 77%), as colourless solid. $^1$H-NMR (CDCl$_3$) 1.40 (tr, 3H, J=7.13 Hz); 3.85 (s, 3H); 4.40 (q, 2H, J=7.13, 14.25 Hz); 4.45 (s, 1H); 6.91 (dd, 1H, J=2.25, 8.68 Hz); 7.04 (d, 1H, J=1.87 Hz); 7.51 (d, 1H, J=5.17 Hz), Step C: 6-Methoxybenzofuran-2-carboxylic acid: To a stirred solution of Product of Step B (0.25 g, 1.21 mmol) in a mixture of THF, MeOH and H$_2$O (5 ml:2 ml:1 ml), LiOH (0.145 g, 6 mmol) in H$_2$O (0.5 ml) was added and the mixture was stirred for 3 h at room temp. The solvents were distilled off and the residue was portioned between EtOAc (20 ml) and 1M HCl (2 ml). The organic layer was washed with H$_2$O, dried over MgSO$_4$ and filtered. The filtrate was evaporated to dryness to give the title compound (0.21 g, 91%), as a colourless solid. $^1$H-NMR (DMSO-d$_6$) 7.61 (d, 1H, J=8.67 Hz); 7.54 (s, 1H); 7.24 (d, 1H, J=1.59 Hz); 6.93 (dd, 1H, J=8.67, 2.4 Hz); 3.8 (s, 3H).

Step D: 3-(3-Iodo-4-isopropoxyphenyl)-5-(6-methoxybenzofuran-2-yl)-1,2,4-oxadiazole: When the product of Step C was substituted for 3-chloro-4-propoxybenzoic acid in Example 36, Step B, the similar procedure afforded the title compound in 67% yield, as colourless solid. $^1$H-NMR (CDCl$_3$) 8.6 (d, 1H, J=2.04 Hz); 8.08 (dd, 1H, J=8.58, 2.1 Hz); 7.63 (b, 1H); 7.57 (d, 1H, J=8.7 Hz); 7.13 (d, 1H, J=1.8 Hz); 6.97 (dd, 1H, J=8.7, 2.19 Hz); 6.87 (d, 1H, J=8.73 Hz); 4.69-4.59 (m, 1H); 3.88 (s, 3H); 1.4 (d, 6H, J=6.33 Hz).

Step E: 2-Iodo-4-(5-(6-methoxybenzofuran-2-yl)-1,2,4-oxadiazol-3-yl)phenol: When the product of Step D was substituted for 5-(3-chloro-4-propoxyphenyl)-3-(3-iodo-4-isopropoxyphenyl)-1,2,4-oxadiazole in Example 36, Step C, the similar procedure afforded the title compound in 65% yield, as colourless solid. $^1$H-NMR (CDCl$_3$) 8.53 (d, 1H, J=2.01 Hz); 8.06 (dd, 1H, J=8.49, 2.01 Hz); 7.64 (b, 1H); 7.6 (d, 1H, J=8.7 Hz); 7.13 (b, 1H); 7.08 (d, 1H, J=8.46 Hz); 6.98 (dd, 1H, J=8.7, 2.22 Hz); 3.89 (s, 3H).

Step F: tert-Butyl 5-(5-(5-(6-methoxybenzofuran-2-yl)-1,2,4-oxadiazol-3-yl)benzofuran-2-yl)-2,2-dimethyl-1,3-dioxan-5-ylcarbamate: When the product of Step E was substituted for 4-(5-(3-chloro-4-propoxyphenyl)-1,2,4-oxadiazol- 3-yl)-2-iodophenol in Example 36, Step D, the similar procedure afforded the title compound in 64% yield, as pale paste.

Step G: 2-Amino-2-(5-(5-(6-methoxybenzofuran-2-yl)-1,2,4-oxadiazol-3-yl)benzofuran-2-yl)propane-1,3-diol: When the product of Step F was substituted for tert-butyl 5-(5-(5-(3-chloro-4-propoxyphenyl)-1,2,4-oxadiazol-3-yl)benzofuran-2-yl)-2,2-dimethyl-1,3-dioxan-5-ylcarbamate in Example 36, Step E, the similar procedure afforded the title compound in 26% yield, as creamy green solid. $^1$H-NMR (CD$_3$OD) 8.39 (d, 1H, J=1.74 Hz); 8.08 (dd, 1H, J=8.73, 1.89 Hz); 7.68 (b, 1H); 7.63 (d, 1H, J=8.73 Hz); 7.58 (d, 1H, J=8.7 Hz); 7.14 (d, 1H, J=1.8 Hz); 7.03 (s, 1H); 6.92 (dd, 1H, J=8.7, 2.22 Hz); 3.98 (d, 2H, J=11.00 Hz); 3.88 (d, 2H, J=11.01 Hz); 3.85 (s, 3H).

Example 44

2-Amino-2-(5-(5-(4-propylphenyl)-1,2,4-oxadiazol-3-yl)benzofuran-2-yl)propane-1,3-diol Step A: 3-(3-Iodo-4-isopropoxyphenyl)-5-(4-propylphenyl)-1,2,4-oxadiazole: When 4-propylbenzoic acid was substituted for 3-chloro-4-propoxy benzoic acid in Example 36, Step B, the similar procedure afforded the title compound in 82% yield, as colourless solid. $^1$H-NMR (CDCl$_3$) 8.58 (d, 1H, J=2.04 Hz); 8.11-8.05 (m, 3H); 7.34 (d, 2H, J=8.25 Hz); 6.88 (d, 1H, J=8.73 Hz); 4.7-4.59 (m, 1H); 2.67 (t, 2H, J=7.83 Hz); 1.72-1.41 (m, 2H); 0.95 (t, 3H, J=7.29 Hz).

Step B: 2-Iodo-4-(5-(4-propylphenyl)-1,2,4-oxadiazol-3-yl)phenol: When the product of Step A was substituted for 5-(3-chloro-4-propoxyphenyl)-3-(3-iodo-4-isopropoxyphenyl)-1,2,4-oxadiazole in Example 36, Step C, the similar procedure afforded the title compound in 82% yield, as colourless solid. $^1$H-NMR (CDCl$_3$) 8.48 (d, 1H, J=1.98 Hz); 8.08 (d, 2H, J=8.25 Hz); 8.03 (dd, 1H, J=8.49, 2.01 Hz); 7.33 (d, 2H, J=8.25 Hz); 7.07 (d, 1H, J=8.49 Hz); 2.66 (t, 2H, J=7.5 Hz); 1.71-1.61 (m, 2H); 0.95 (t, 3H, J=7.29 Hz).

Step C: tert-Butyl 2,2-dimethyl-5-(5-(5-(4-propylphenyl)-1,2,4-oxadiazol-3-yl)benzo-furan-2-yl)-1,3-dioxan-5-ylcarbamate: When the product of Step B was substituted for 4-(5-(3-chloro-4-propoxyphenyl)-1,2,4-oxadiazol-3-yl)-2-iodophenol in Example 36, Step D, the similar procedure afforded the title compound in 35% yield, as pale paste. $^1$H-NMR (CDCl$_3$) 8.35 (s, 1H); 8.13-8.06 (m, 3H); 7.52 (d, 1H, J=8.64 Hz); 7.34 (d, 2H, J=8.22 Hz); 6.75 (s, 1H); 5.35 (s, 1H); 4.26 (b, 4H); 2.67 (t, 2H, J=7.41 Hz); 1.74-1.67 (m, 2H); 1.64 (s, 6H); 1.5 (s, 9H); 0.96 (t, 2H, J=7.29 Hz).

Step D: 2-Amino-2-(5-(5-(4-propylphenyl)-1,2,4-oxadiazol-3-yl)benzofuran-2-yl)propane-1,3-diol: When the product of Step C was substituted for tert-butyl 5-(5-(5-(3-chloro-4-propoxyphenyl)-1,2,4-oxadiazol-3-yl)benzofuran-2-yl)-2,2-dimethyl-1,3-dioxan-5-ylcarbamate in Example 36, Step E, the similar procedure afforded the title compound in 28% yield, as creamy solid. $^1$H-NMR (DMSO-d$_6$) 8.30 (s, 1H); 8.08 (d, 2H, J=6.6 Hz); 7.94 (d, 1H, J=7.5 Hz); 7.68 (d, 1H, J=7.5 Hz); 7.46 (d, 2H, J=7.5 Hz); 6.92 (s, 1H); 3.67 (b, 2H); 3.59 (b, 2H); 2.65 (b, 2H); 1.63-1.6 (m, 2H); 0.88 (t, 2H, J=6.3 Hz).

Example 45

2-Amino-2-(5-(5-(4-ethoxyphenyl)-1,2,4-oxadiazol-3-yl)benzofuran-2-yl)propane-1,3-diol Step A: 5-(4-Ethoxyphenyl)-3-(3-iodo-4-isopropoxyphenyl)-1,2,4-oxadiazole: When 4-ethoxybenzoic acid was substituted for 3-chloro-4-propoxy benzoic acid in Example 36, Step B, the similar procedure afforded the title compound in 53% yield, as white solid. $^1$H-NMR (CDCl$_3$) 8.57 (d, 1H, J=2.04 Hz); 8.11 (d, 2H, J=8.88 Hz); 8.05 (dd, 1H, J=8.58, 2.04 Hz); 6.99 (d, 2H, J=8.88 Hz); 6.87 (d, 1H, J=8.67 Hz); 4.69-4.61 (m, 1H); 4.11 (q, 2H, J=6.99, 13.98 Hz); 1.45 (t, 3H, J=6.99 Hz).

Step B: 4-(5-(4-Ethoxyphenyl)-1,2,4-oxadiazol-3-yl)-2-iodophenol: When the product of Step A was substituted for 5-(3-chloro-4-propoxyphenyl)-3-(3-iodo-4-isopropoxyphenyl)-1,2,4-oxadiazole in Example 36, Step C, the similar procedure afforded the title compound in 87% yield, as white solid. $^1$H-NMR (CDCl$_3$) 8.47 (d, 1H, J=1.95 Hz); 8.11 (d, 2H, J=8.94 Hz); 8.03 (dd, 1H, J=8.46, 2.01 Hz); 7.07 (d, 2H, J=8.49 Hz); 4.11 (q, 2H, J=6.96, 13.98 Hz); 1.45 (t, 3H, J=6.96 Hz).

Step C: tert-Butyl 5-(5-(5-(4-ethoxyphenyl)-1,2,4-oxadiazol-3-yl)benzofuran-2-yl)-2,2-dimethyl-1,3-dioxan-5-ylcarbamate: When the product of Step B was substituted for 4-(5-(3-chloro-4-propoxyphenyl)-1,2,4-oxadiazol-3-yl)-2-iodophenol in Example 36, Step D, the similar procedure afforded the title compound in 60% yield, as pale paste. $^1$H-NMR (CDCl$_3$) 8.34 (s, 1H); 8.14 (d, 2H, J=8.88 Hz); 8.07 (dd, 1H, J=8.61, 1.68 Hz); 7.51 (d, 1H, J=8.52 Hz); 7.00 (d, 2H, J=8.94 Hz); 6.75 (s, 1H); 5.34 (s, 1H); 4.3-4.14 (b, 4H); 4.1 (t, 2H, J=7.02 Hz); 1.44-1.39 (b, 18H).

Step D: 2-Amino-2-(5-(5-(4-ethoxyphenyl)-1,2,4-oxadiazol-3-yl)benzofuran-2-yl)propane-1,3-diol: When the product of Step C was substituted for tert-butyl 5-(5-(5-(3-chloro-4-propoxyphenyl)-1,2,4-oxadiazol-3-yl)benzofuran-2-yl)-2,2-dimethyl-1,3-dioxan-5-ylcarbamate in Example 36, Step E, the similar procedure afforded the title compound in 32% yield, as light yellow solid. $^1$H-NMR (DMSO-d$_6$) 8.09 (s, 1H); 7.96 (d, 2H, J=8.4 Hz); 7.7 (d, 1H, J=8.4 Hz); 7.15 (d, 2H, J=9 Hz); 6.98 (s, 1H); 5.1 (b, 2H); 4.13 (q, 2H, J=6.9, 13.8 Hz); 3.73 (d, 2H, J=8.1 Hz); 3.64 (d, 2H, J=8.1 Hz); 1.34 (t, 3H, J=6.9 Hz).

Example 46

2-Amino-2-(6-chloro-5-(5-(4-propyl phenyl)-1,2,4-oxadiazol-3-yl)benzofuran-2-yl)propane-1,3-diol Step A: 2-Chloro-N-hydroxy-5-iodo-4-isopropoxybenzimidamide: To a stirred solution of 2-chloro-4-isopropoxybenzonitrile (0.8 g, 4.1 mmol) and CF$_3$CO$_2$Ag (1.3 g, 5.1 mmol) in CH$_2$Cl$_2$ (50 ml) I$_2$ (1 g, 4 mmol) was added and the mixture was stirred for 6 h at reflux. This was filtered through the Celite bead and the washed with CH$_2$Cl$_2$. The combined filtrates were evaporated to dryness and the residue was purified by FCC (SiO$_2$, hexane/EtOAc) to give 2-chloro-5-iodo-4-isopropoxybenzonitrile (0.335 g, 26%), as white solid. $^1$H NMR (CDCl$_3$) 7.99 (s, 1H); 6.82 (s, 1H); 4.66-4.58 (m, 1H); 1.41 (d, 6H, J=6.03 Hz. This (0.32 g, 1 mmol) was converted to the title compound (0.335 g; 95%) according to the procedure of Example 36 Step A. $^1$H NMR (CDCl$_3$) 7.89 (s, 1H); 6.79 (s, 1H); 4.86-4.49 (m, 1H); 1.4 (d, 6H)

Step B: 3-(2-Chloro-5-iodo-4-isopropoxyphenyl)-5-(4-propylphenyl)-1,2,4-oxadiazole: When the product of Step A and 4-propylbenzoic acid were substituted for N-hydroxy-3-iodo-4-isopropoxybenzimidamide and 3-chloro-4-propoxybenzoic acid in Example 36, Step B, the similar procedure afforded the title compound in 20% yield, as white solid. $^1$H NMR (CDCl$_3$) 8.46 (s, 1H); 8.10 (d, 2H, J=8.25 Hz); 7.34 (d, 2H, J=8.28 Hz); 6.92 (s, 1H); 7.67-7.59 (m, 1H); 2.67 (t, 2H, J=7.35 Hz); 1.72-1.65 (m, 2H); 1.43 (d, 6H, J=6.06 Hz); 0.96 (t, 3H, J=7.32 Hz).

Step C: 5-Chloro-2-iodo-4-(5-(4-propylphenyl)-1,2,4-oxadiazol-3-yl)phenol: When the product of Step B was substituted for 5-(3-chloro-4-propoxy phenyl)-3-(3-iodo-4-isopropoxyphenyl)-1,2,4-oxadiazole in Example 36, Step C, the similar procedure afforded the title compound in 55% yield, as creamy solid. $^1$H NMR (CDCl$_3$) 8.37 (s, 1H); 8.10 (d, 2H, J=8.25 Hz); 7.33 (d, 2H, J=8.25 Hz); 7.16 (s, 1H); 5.78 (b, 1H); 2.67 (t, 2H, J=7.38 Hz); 1.74-1.56 (m, 2H); 0.96 (t, 3H, J=7.32 Hz).

Step D: 2-Amino-2-(6-chloro-5-(5-(4-propylphenyl)-1,2,4-oxadiazol-3-yl)benzofuran-2-yl)propane-1,3-diol: When tert-butyl 5-(5-(5-(3-chloro-4-propoxyphenyl)-1,2,4-oxadiazol-3-yl)benzofuran-2-yl)-2,2-dimethyl-1,3-dioxan-5-ylcarbamate was replaced with the tert-butyl 5-(6-chloro-5-(5-(4-propylphenyl)-1,2,4-oxadiazol-3-yl)benzofuran-2-yl)-2,2-dimethyl-1,3-dioxan-5-ylcarbamate (obtained as crude via a process as described in Example 36, Step D) the similar procedure as in Example 36, Step E gave the title compound (0.006 g, 40%) as white solid. $^1$H NMR (CD$_3$OD) 8.12 (d, 2H, J=8.28 Hz); 8.12 (s, 1H); 7.75 (s, 1H); 7.43 (d, 2H, J=8.31 Hz); 6.9 (s, 1H); 3.88 (d, 2H, J=10.9 Hz); 3.78 (d, 1H, J=10.9 Hz); 2.7 (t, 2H, J=7.41 Hz); 1.76-1.64 (m, 2H); 0.97 (t, 3H, J=7.32 Hz).

Example 47

2-Amino-2-(5-(5-(1-butyl-1H-pyrazol-4-yl)-1,2,4-oxadiazol-3-yl)benzofuran-2-yl)propane-1,3-diol Step A: 1-Butyl-1H-pyrazole-4-carboxylic acid: To a stirred suspension of 4-iodopyrazole (0.3 g, 1.55 mmol) and 60% NaH (0.08 g, 2 mmol) in anhydrous THF (1 ml) butyl bromide (0.5 ml) was added and the mixture was stirred overnight at 70° C. The mixture was quenched with saturated NH$_4$Cl and extracted with EtOAc (50 ml). The organic layer was washed with H$_2$O, dried over MgSO$_4$ and filtered. The filtrate was distilled off and the residue was dried in vacuo to give 1-butyl-4-iodo-1H-pyrazole (0.39 g, 100%), as colourless oil. $^1$H NMR (CDCl$_3$) 7.47 (s, 1H); 7.39 (s, 1H); 4.09 (t, 2H, J=7.14 Hz); 1.85-1.75 (m, 2H); 1.35-1.23 (m, 2H); 0.91 (t, 3H, J=7.32 Hz). To a stirred solution of the above product (0.36 g, 1.44 mmol) in anhydrous THF (0.5 ml) 2M iPrMgCl in THF (2 ml) was added at 0° C. and after warming up to room temperature anhydrous DMF (1 ml) was added to it. This was stirred for 1 h at room temperature, than quenched with saturated NH$_4$Cl and extracted with EtOAc (30 ml). The organic layer was washed with H$_2$O, dried over MgSO$_4$ and filtered. The filtrate was evaporated to dryness to give 1-butyl-1H-pyrazole-4-carbaldehyde (0.27 g; 100%), as pale oil. $^1$H NMR (CDCl$_3$) 9.82 (s, 1H); 7.93 (s, 1H); 7.89 (s, 1H); 4.13 (t, 2H, J=7.11 Hz); 1.9-1.8 (m, 2H); 1.4-1.22 (m, 2H); 0.92 (t, 3H, J=7.29 Hz). To a stirred solution of above aldehyde (0.22 g, 1.44 mmol) in the mixture of dioxane and H$_2$O (15 ml: 3 ml) KMnO$_4$ (0.25 g; 1.58 mmol) was added over a period of 30 min. The mixture was evaporated to dryness and the residue was treated in the mixture of EtOAc and MeOH (20 ml: 5 ml) and filtered through Celite pad. The filtrate was evaporated to dryness to give the title compound (0.24 g; 100%), as creamy crystalline solid. $^1$H NMR (CDCl$_3$) 7.8 (s, 1H); 7.56 (b, 1H); 4.05 (b, 2H); 1.7 (b, 2H); 1.18 (b, 2H); 0.83 (b, 3H).

Step B: 5-(1-Butyl-1H-pyrazol-4-yl)-3-(3-iodo-4-isopropoxyphenyl)-1,2,4-oxadiazole: When the product of Step A was substituted for 3-chloro-4-propoxybenzoic acid in Example 36, Step B the similar procedure afforded the title compound in 17% yield, as creamy gum. $^1$H NMR (CDCl$_3$) 8.53 (d, 1H, J=2.07 Hz); 8.1 (s, 1H); 8.08 (s, 1H); 8.00 (dd, 1H, J=8.61, 2.16 Hz); 8.87 (d, 1H, J=8.73 Hz); 4.68-4.6 (m, 2H); 4.2 (t, 2H, J=7.11 Hz); 2.02-1.85 (m, 2H); 1.42-1.32 (m, 2H); 0.95 (t, 3H, J=7.32 Hz).

Step C: 4-(5-(1-Butyl-1H-pyrazol-4-yl)-1,2,4-oxadiazol-3-yl)-2-iodophenol: When the product of Step B was substituted for 5-(3-chloro-4-propoxy phenyl)-3-(3-iodo-4-isopropoxy phenyl)-1,2,4-oxadiazole in Example 36, Step C, the similar procedure afforded the title compound in 72% yield, as creamy solid. $^1$H NMR (CDCl$_3$) 8.45 (d, 1H, J=1.98 Hz); 8.12 (s, 1H); 8.09 (s, 1H); 7.99 (dd, 1H, J=8.49, 2.01 Hz); 7.06 (d, 1H, J=8.49 Hz); 4.2 (t, 2H, J=7.08 Hz); 2.02-1.85 (m, 2H); 1.42-1.26 (m, 2H); 0.95 (t, 3H, J=7.29 Hz).

Step D: tert-Butyl 5-(5-(5-(1-butyl-1H-pyrazol-4-yl)-1,2,4-oxadiazol-3-yl)benzofuran-2-yl)-2,2-dimethyl-1,3-dioxan-5-ylcarbamate: When the product of Step C was substituted for 4-(5-(3-chloro-4-propoxyphenyl)-1,2,4-oxadiazol-3-yl)-2-iodophenol in Example 36, Step D, the similar procedure afforded the title compound in 68% yield, as pale paste. $^1$H NMR (CDCl$_3$) 8.3 (s, 1H); 8.13 (s, 1H); 8.01 (s, 1H); 7.51 (d, 1H, J=8.7 Hz); 6.74 (s, 1H); 5.32 (s, 1H); 4.29-4.18 (m, 6H); 2.02-1.91 (m, 2H); 1.54-1.34 (b, 17H); 0.96 (t, 3H, J=7.35 Hz).

Step E: 2-Amino-2-(5-(5-(1-butyl-1H-pyrazol-4-yl)-1,2,4-oxadiazol-3-yl)benzofuran-2-yl)propane-1,3-diol: When the product of Step D was substituted for tert-butyl 5-(5-(5-(3-chloro-4-propoxyphenyl)-1,2,4-oxadiazol-3-yl)benzofuran-2-yl)-2,2-dimethyl-1,3-dioxan-5-ylcarbamate in Example 36, Step E, the similar procedure afforded the title compound in 46% yield, as light creamy solid. $^1$H NMR (CD$_3$OD) 8.46 (broad s, 1H); 8.32 (broad s, 1H); 8.13 (broad s, 1H); 8.02 (d, 1H, J=7.98 Hz); 7.62 (d, 1H, J=8.31 Hz); 6.97 (s, 1H); 4.25 (t, 2H, J=6.21 Hz); 3.93 (b, 4H); 1.91-1.86 (m, 2H); 1.36-1.31 (m, 2H); 0.95 (t, 3H, J=7.02 Hz).

Example 48

2-Amino-2-(5-(5-(3-nitro-4-propoxyphenyl)-1,2,4-oxadiazol-3-yl)benzofuran-2-yl)propane-1,3-diol Step A: 3-Nitro-4-propoxybenzoic acid: To a stirred solution of 3-nitro-4-propoxymethylbenzoate (0.35 g, 1.46 mmol) in a mixture of THF and EtOH (3 ml:1 ml) the solution of LiOH (0.345 g; 15 mmol) in H$_2$O (1 ml) was added and the mixture was stirred for 4 h at room temperature. The solvent was distilled off and the residue was treated with 1M HCl and extracted with EtOAc (50 ml). The organic layer was washed with H$_2$O, dried over MgSO$_4$ and filtered. The filtrate was evaporated to dryness to give the title compound (0.32 g, 97%), as creamy solid. $^1$H NMR (CDCl$_3$) 8.53 (d, 1H, J=1.65 Hz); 8.21 (dd, 1H, J=8.79, 1.62 Hz); 7.12 (d, 1H, J=8.82 Hz); 4.14 (t, 2H, J=6.39 Hz); 1.94-1.82 (m, 2H); 1.07 (t, 3H, J=7.35 Hz).

Step B: 3-(3-Iodo-4-isopropoxyphenyl)-5-(3-nitro-4-propoxyphenyl)-1,2,4-oxadiazole: When the product of Step A was substituted for 3-chloro-4-propoxybenzoic acid in Example 36, Step B, the similar procedure afforded the title compound in 66% yield, as creamy solid. $^1$H NMR (CDCl$_3$) 8.64 (d, 1H, J=2.13 Hz); 8.55 (d, 1H, J=2.1 Hz); 8.3 (dd, 1H, J=8.82, 2.16 Hz); 8.2 (dd, 1H, J=8.58, 2.01 Hz); 7.2 (d, 1H, J=8.88 Hz); 6.96 (d, 1H, J=8.85 Hz); 4.7-4.62 (m, 1H); 4.16 (t, 2H, J=6.39 Hz); 1.94-1.84 (m, 2H); 1.42 (d, 6H, J=6.03 Hz); 1.08 (t, 3H, J=7.35 Hz).

Step C: 2-Iodo-4-(5-(3-nitro-4-propoxyphenyl)-1,2,4-oxadiazol-3-yl)phenol: When the product of Step B was substituted for 5-(3-chloro-4-propoxyphenyl)-3-(3-iodo-4-isopropoxyphenyl)-1,2,4-oxadiazole in Example 36, Step C, the similar procedure afforded the title compound in 77% yield, as creamy solid. $^1$H NMR (CDCl$_3$) 8.65 (d, 1H, J=2.16 Hz); 8.47 (d, 1H, J=1.95 Hz); 8.3 (dd, 1H, J=8.82, 2.19 Hz); 8.03 (dd, 1H, J=8.49, 2.01 Hz); 7.21 (d, 1H, J=8.88 Hz); 7.08 (d, 1H, J=8.49 Hz); 4.17 (t, 2H, J=6.39 Hz); 1.96-1.84 (m, 2H); 1.09 (t, 3H, J=7.38 Hz).

Step D: tert-Butyl 2,2-dimethyl-5-(5-(5-(3-nitro-4-propoxyphenyl)-1,2,4-oxadiazol-3-yl)benzofuran-2-yl)-1,3-dioxan-5-ylcarbamate: When the product of Step C was substituted for 4-(5-(3-chloro-4-propoxyphenyl)-1,2,4-oxadiazol-3-yl)-2-iodophenol in Example 36, Step D, the similar procedure afforded the title compound in 54% yield, as pale solid. $^1$H NMR (CDCl$_3$) 8.68 (d, 1H, J=2.16 Hz); 8.35-8.31 (m, 2H); 8.06 (dd, 1H, J=8.64, 1.71 Hz); 7.54 (d, 1H, J=8.64 Hz); 7.21 (d, 1H, J=8.97 Hz); 6.76 (s, 1H); 5.33 (s, 1H); 4.3-3.95 (m, 6H); 2.41-1.87 (m, 2H); 1.58-1.21 (m, 15H); 1.09 (t, 3H, J=7.44 Hz).

Step E: 2-Amino-2-(5-(5-(3-nitro-4-propoxyphenyl)-1,2,4-oxadiazol-3-yl)benzofuran-2-yl)propane-1,3-diol: When the product of Step D was substituted for tert-butyl 5-(5-(5-(3-chloro-4-propoxy phenyl)-1,2,4-oxadiazol-3-yl)benzofuran-2-yl)-2,2-dimethyl-1,3-dioxan-5-ylcarbamate in Example 36, Step E, the similar procedure afforded the title compound in 49% yield, as creamy solid. $^1$H NMR (DMSO-d$_6$) 8.6 (s, 1H); 8.37 (d, 1H, J=8.37 Hz); 8.31 (s, 1H); 7.94 (d, 1H, J=8.52 Hz); 7.68 (d, 1H, J=8.52 Hz); 7.59 (d, 1H, J=8.82 Hz); 6.91 (s, 1H); 4.87 (b, 2H); 4.23 (t, 2H, J=5.82 Hz); 3.67 (d, 2H, J=10.05 Hz); 3.58 (d, 2H, J=9.96 Hz); 1.78-1.71 (m, 2H); 0.97 (t, 3H, J=7.26 Hz).

Example 49

5-(3-(2-(2-Amino-1,3-dihydroxypropan-2-yl)benzofuran-5-yl)-1,2,4-oxadiazol-5-yl)-2-propoxybenzonitrile Step A: 3-Cyano-4-propoxybenzoic acid: To a stirred solution of 3-bromo-4-propoxybenzaldehyde (0.6 g, 2.47 mmol) in anhydrous DMF (5 ml) CuCN (0.67 g; 7.4 mmol) was added and the mixture was stirred for 4 h at reflux. After cooling to room temperature, the mixture was treated with EtOAc (50 ml) and 1M HCl (10 ml) and stirred for 15 min. The organic layer was separated, dried over MgSO$_4$ and filtered. The filtrate was evaporated to dryness to give 5-formyl-2-propoxybenzonitrile (0.41 g; 88%), as yellow oil $^1$H NMR (CDCl$_3$) 9.87 (s, 1H); 8.07 (d, 1H, J=1.95 Hz); 8.03 (dd, 1H, J=8.67, 2.1 Hz); 7.06 (d, 1H, J=8.7 Hz); 4.13 (t, 2H, J=6.45 Hz); 1.97-1.85 (m, 2H); 1.1 (t, 3H, J=7.35 Hz). The above benzaldehyde was oxidised via a similar procedure as described in Example 47 Step A, to give the title compound (0.29 g; 68%), as white solid. $^1$H NMR (CDCl$_3$) 8.3 (d, 1H, J=1.71 Hz); 8.23 (dd, 1H, J=8.88, 2.1 Hz); 7.00 (d, 1H, J=7.62 Hz); 4.12 (t, 2H, J=6.48 Hz); 1.97-1.85 (m, 2H); 1.09 (t, 3H, J=7.38 Hz).

Step B: 5-(3-(3-Iodo-4-isopropoxyphenyl)-1,2,4-oxadiazol-5-yl)-2-propoxy benzonitrile: When the product of Step A was substituted for 3-chloro-4-propoxybenzoic acid in Example 36, Step B, the similar procedure afforded the title compound in 57% yield, as creamy solid. $^1$H NMR (CDCl$_3$) 8.55 (d, 1H, J=2.1 Hz); 8.4 (d, 1H, J=2.1 Hz); 8.31 (dd, 1H, J=8.85, 2.16 Hz); 8.04 (dd, 1H, J=8.61, 2.1 Hz); 7.09 (d, 1H, J=8.94 Hz); 6.88 (d, 1H, J=8.7 Hz); 4.7-4.6 (m, 1H); 4.14 (t, 2H, J=6.48 Hz); 1.98-1.87 (m, 2H); 1.42 (d, 6H, J=6.06 Hz); 1.18 (t, 3H, J=7.38 Hz).

Step C: 5-(3-(4-Hydroxy-3-iodophenyl)-1,2,4-oxadiazol-5-yl)-2-propoxy benzonitrile: When the product of Step B was substituted for 5-(3-chloro-4-propoxyphenyl)-3-(3-iodo-4-isopropoxyphenyl)-1,2,4-oxadiazole in Example 36, Step C, the similar procedure afforded the title compound in 74% yield, as creamy solid. $^1$H NMR (CDCl$_3$) 8.46 (d, 1H, J=1.95 Hz); 8.4 (d, 1H, J=2.13 Hz); 8.31 (dd, 1H, J=8.88, 2.19 Hz); 8.02 (dd, 1H, J=8.49, 1.68 Hz); 7.1 (d, 1H, J=8.94 Hz); 7.09 (d, 1H, J=8.49 Hz); 5.64 (bs, 1H); 4.12 (t, 2H, J=6.48 Hz); 2.02-1.86 (m, 2H); 1.1 (t, 3H, J=7.38 Hz).

Step D: tert-Butyl 5-(5-(5-(3-cyano-4-propoxyphenyl)-1,2,4-oxadiazol-3-yl)benzofuran-2-yl)-2,2-dimethyl-1,3-dioxan-5-ylcarbamate: When the product of Step C was substituted for 4-(5-(3-chloro-4-propoxyphenyl)-1,2,4-oxadiazol-3-yl)-2-iodophenol in Example 36, Step D, the similar procedure afforded the title compound in 44% yield, as pale paste. $^1$H NMR (CDCl$_3$) 8.42 (d, 1H, J=2.16 Hz); 8.34 (dd, 1H, J=6.63, 2.19 Hz); 8.06 (dd, 1H, J=8.61, 1.71 Hz); 7.99 (b, 1H); 7.52 (d, 1H, J=8.58 Hz); 7.1 (d, 1H, J=8.94 Hz); 6.76 (s, 1H); 5.33 (s, 1H); 4.26 (t, 4H, J=11.4 Hz); 4.15 (t, 2H, J=11.4 Hz); 4.15 (t, 2H, J=6.48 Hz); 2.02-1.87 (m, 2H); 1.56-1.38 (m, 15H); 1.1 (t, 3H, J=7.38 Hz).

Step E: 5-(3-(2-(2-Amino-1,3-dihydroxypropan-2-yl)benzofuran-5-yl)-1,2,4-oxadiazol-5-yl)-2-propoxy benzonitrile: When product of Step D was substituted for tert-butyl 5-(5-(5-(3-chloro-4-propoxyphenyl)-1,2,4-oxadiazol-3-yl)benzofuran-2-yl)-2,2-dimethyl-1,3-dioxan-5-ylcarbamate (obtained as crude via a process as described in Example 36, Step D) in Example 36, Step E, the similar procedure afforded the title compound in 29% yield, as off white solid. $^1$H NMR (DMSO-d$_6$) 8.49 (d, 1H, J=2.22 Hz); 8.39 (dd, 1H, J=8.91, 2.22 Hz); 8.28 (d, 1H, J=1.41 Hz); 7.93 (dd, 1H, J=8.55, 1.71 Hz); 7.68 (d, 1H, J=8.58 Hz); 7.48 (d, 1H, J=9.06 Hz); 6.89 (s, 1H); 4.78 (b, 2H); 4.22 (t, 2H, J=6.42 Hz); 3.68-3.52 (m, 4H); 1.84-1.73 (m, 2H); 1.0 (t, 3H, J=7.41 Hz).

Example 50

2-Amino-2-(5-(5-(3-bromo-4-propoxyphenyl)-1,2,4-oxadiazol-3-yl)benzofuran-2-yl)propane-1,3-diol Step A: 3-Bromo-4-propoxybenzoic acid: 3-Bromo-4-propoxybenzaldehyde was oxidized by KMnO$_4$, according to the procedure as described in Example 47, Step A, to give the title compound in 96%, as white solid. $^1$H-NMR (DMSO-d$_6$) 0.98 (t, 3H, J=7.32 Hz); 1.68-1.79 (m, 2H); 4.06 (t, 2H, J=6.39 Hz); 7.14 (d, 1H, J=8.7 Hz); 7.87 (dd, 1H, J=2.07, 8.61 Hz); 8.01 (d, 1H, J=2.04 Hz); 11.2 (broad s, 1H).

Step B: 4-(5-(3-Bromo-4-propoxyphenyl)-1,2,4-oxadiazol-3-yl)-2-iodophenol: When the product of Step A was substituted for 3-chloro-4-propoxybenzoic acid in Example 36, Step B, the similar procedure afforded the title compound in 70% yield, as white solid. $^1$H NMR (CDCl$_3$) 8.47 (s, 1H); 8.38 (s, 1H); 8.08 (d, 1H, J=9.09 Hz); 8.03 (d, 1H, J=8.79 Hz); 7.7 (d, 1H, J=8.55 Hz); 6.98 (d, 1H, J=8.67 Hz); 4.08 (t, 2H, J=6.39 Hz); 1.96-1.84 (m, 2H); 1.1 (t, 3H, J=7.35 Hz).

Step C: tert-Butyl 5-(5-(5-(3-bromo-4-propoxy-phenyl)-1,2,4-oxadiazol-3-yl)benzofuran-2-yl)-2,2-dimethyl-1,3-dioxan-5-yl-carbamate: When with the product of Step C was substituted for 4-(5-(3-chloro-4-propoxyphenyl)-1,2,4-oxadiazol-3-yl)-2-iodophenol in Example 36, Step D, the similar procedure afforded the title compound in 98% yield, as pale paste.

Step D: 2-Amino-2-(5-(5-(3-bromo-4-propoxyphenyl)-1,2,4-oxadiazol-3-yl)benzofuran-2-yl)propane-1,3-diol: When the product of Step C is substituted for tert-butyl 5-(5-(5-(3-chloro-4-propoxyphenyl)-1,2,4-oxadiazol-3-yl)benzofuran-2-yl)-2,2-dimethyl-1,3-dioxan-5-ylcarbamate in Example 36, Step E, the similar procedure afforded the title compound in 10% yield, as light yellow solid. $^1$H NMR (CD$_3$OD) 8.32 (b, 2H); 8.1 (d, 1H, J=8.46 Hz); 8.00 (d, 1H, J=8.52 Hz); 7.59

(d, 1H, J=8.61 Hz); 7.18 (d, 1H, J=8.58 Hz); 6.91 (s, 1H); 4.1 (t, 2H, J=6.06 Hz); 3.91 (d, 2H, J=10.98 Hz); 3.03 (d, 2H, J=10.95 Hz); 3.32 (b, 2H); 1.9-1.8 (m, 2H); 1.1 (t, 3H, J=7.35 Hz).

Example 51

2-Amino-2-(5-octylbenzo[b]thiophen-2-yl)propane-1,3-diol

Step A: 2-Iodo-4-octylaniline: To a stirred mixture of 4-octyl aniline (0.33 g, 1.6 mmol) and $H_2O_2$ (30%, 0.5 ml) in $CH_3OH$ (1.5 ml) was added $I_2$ (0.2 g, 0.8 mmol) and the mixture was stirred overnight at room temperature. The solvent was distilled off and the residue was diluted to 10 ml with $CH_2Cl_2$, washed with $H_2O$, dried over $MgSO_4$ and filtered. The filtrate was evaporated to dryness to give the title compound (0.46 g, 86%) as yellow paste. $^1H$ NMR ($CDCl_3$) 7.44 (d, 1H, J=1.83 Hz); 6.93 (dd, 1H, J=8.07, 1.86 Hz); 6.65 (d, 1H, J=8.1 Hz); 4.1 (b, 2H); 2.43 (t, 2H, J=7.5 Hz); 1.54-1.49 (m, 2H); 1.26 (b, 10H); 0.87 (t, 3H, J=6.39 Hz).

Step B: 2-Iodo-4-octylbenzenethiol: To a stirred mixture of the product of Step A (0.4 g; 1.21 mmol) in 35% HCl (0.2 ml) an ice cold solution of $NaNO_2$ (0.1 g, 1.3 mmol) in $H_2O$ (1 ml) was added at 0° C., followed by a solution of K-ethylxanthate, freshly prepared by rapid stirring of a mixture of KOH (0.085 g, 1.5 mmol) and $CS_2$ (0.173 g, 1.5 mmol) in a mixture of EtOH and $H_2O$ (1 ml: 1.5 ml) for 2.5 h at room temperature. The resulting mixture was stirred for 5 h at 55° C., than cooled to room temperature and extracted with EtOAc (50 ml). The organic layer was separated, washed with $H_2O$, dried over $MgSO_4$ and filtered. The filtrate was evaporated and the residue was diluted to 20 ml with EtOH and KOH (0.5 g, 3.62 mmol) was added. This was stirred for 5 h at reflux and the mixture was evaporated to dryness and the residue was treated with 1M HCl and extracted with EtOAc (20 ml). The organic layer was separated, dried over $MgSO_4$ and filtered. The filtrate was evaporated and the residue was purified by FCC ($SiO_2$, hexane/EtOAc) to give the title compound (0.1 g, 24%), as a yellow paste, which was used as such in next step. $^1H$ NMR ($CDCl_3$) 7.75 (b, 1H); 7.28 (d, 1H, J=7.95 Hz); 7.00 (dd, 1H, J=7.95, 2.0 Hz); 7.02 (s, 1H); 2.51-2.45 (m, 2H); 1.53 (b, 2H); 1.25 (b, 10H); 0.86 (t, 3H, J=6.42 Hz).

Step C: tert-Butyl 2,2-dimethyl-5-(5-octylbenzo[b]thiophen-2-yl)-1,3-dioxan-5-ylcarbamate When with the product of Step B was substituted for 4-(5-(3-chloro-4-propoxyphenyl)-1,2,4-oxadiazol-3-yl)-2-iodophenol in Example 36, Step D, the similar procedure afforded the title compound in 24% yield, as white solid. $^1H$ NMR ($CDCl_3$) 7.65 (d, 1H, J=8.16 Hz); 7.47 (s, 1H); 7.1 (d, 1H, J=6.18 Hz); 7.1 (s, 1H); 5.44 (b, 1H); 4.16 (b, 4H); 2.66 (t, 2H, J=7.5 Hz); 1.6-1.1 (m, 27H); 0.86 (t, 3H, J=6.18 Hz).

Step D: 2-Amino-2-(5-octylbenzo[b]thiophen-2-yl)propane-1,3-diol: When tert-butyl 5-(5-(5-(3-chloro-4-propoxyphenyl)-1,2,4-oxadiazol-3-yl)benzofuran-2-yl)-2,2-dimethyl-1,3-dioxan-5-ylcarbamate was replaced with the product of Step C the similar procedure as described in Example 36, Step E gave the title compound (0.008 g, 38%) as light yellow solid. $^1H$ NMR ($CD_3OD$) 7.74 (d, 1H, J=8.28 Hz); 7.6 (s, 1H); 7.4 (s, 1H); 7.2 (dd, 2H, J=8.34, 1.59 Hz); 4.0 (d, 2H, J=11.46 Hz); 3.94 (d, 2H, J=11.46 Hz); 2.7 (t, 2H, J=7.53 Hz); 1.64 (b, 2H); 1.34-1.26 (b, 10H); 0.85 (t, 3H, J=4.8 Hz).

Example 52

2-Amino-2-(5-octylbenzofuran-2-yl)propane-1,3-diol

Step A: 2-Iodo-4-octylphenol: A mixture of 4-octyl phenol (0.15 g, 0.73 mmol), $CF_3CO_2Ag$ (0.25 g, 1 mmol) and $I_2$ (0.185 g, 0.73 mmol) in $CH_2Cl_2$ (10 ml) was stirred for 0.5 h at 0° C., then for 0.5 h at room temperature. The solution was filtered through Celite bead and washed with $CH_2Cl_2$ (30 ml). The filtrates were evaporated to dryness to give the title compound (0.21 g, 87%) as fawn oil. $^1H$ NMR ($CDCl_3$) 7.32 (d, 1H, J=8.34 Hz); 7.28 (d, 1H, J=1.26 Hz); 6.98 (dd, 1H, 8.37, 1.71 Hz); 6.62 (s, 1H); 4.69 (t, 2H, J=5.88 Hz); 3.62-3.38 (m, 4H); 2.59 (t, 2H, J=7.29 Hz); 1.56-1.51 (m, 2H); 1.34-1.2 (m, 10H); 0.81 (t, 3H, J=6.48 Hz).

Step B: tert-Butyl 2,2-dimethyl-5-(5-octylbenzofuran-2-yl)-1,3-dioxan-5-ylcarbamate: When with the product of Step A was substituted for 4-(5-(3-chloro-4-propoxyphenyl)-1,2,4-oxadiazol-3-yl)-2-iodophenol in Example 36, Step D, the similar procedure afforded the title compound in 53% yield, as a light yellow paste. $^1H$ NMR ($CDCl_3$) 7.33 (d, 1H, J=6.27 Hz); 7.32 (s, 1H); 7.01 (dd, 1H, J=8.4, 1.71 Hz); 6.59 (s, 1H); 5.3 (s, 1H); 4.17 (s, 4H); 2.64 (t, 2H, J=7.77 Hz); 1.62-1.24 (m, 27H); 0.86 (t, 3H, J=6.42 Hz).

Step C: 2-Amino-2-(5-octylbenzofuran-2-yl)propane-1,3-diol: When the product of Step B was substituted for tert-butyl 5-(5-(5-(3-chloro-4-propoxy phenyl)-1,2,4-oxadiazol-3-yl)benzofuran-2-yl)-2,2-dimethyl-1,3-dioxan-5-yl-carbamate in Example 36, Step E, the similar procedure afforded the title compound in 51% yield, as off white solid. $^1H$ NMR (DMSO-$d_6$) 7.44 (d, 1H, J=1.98 Hz); 7.0 (dd, 1H, J=8.28, 1.98 Hz); 6.87 (d, 1H, J=8.22 Hz); 5.11 (s, 1H); 2.47 (t, 2H, J=7.5 Hz); 1.56-1.51 (m, 2H); 1.27-1.26 (m, 10H); 0.87 (t, 3H, J=6.45 Hz).

Example 53

2-(4-(5-(3,4-Diethoxyphenyl)-1,2,4-oxadiazol-3-yl)indoline-1-carboxamido)acetic acid Step A: N-Hydroxy-1H-indole-4-carboximidamide: A mixture of 4-cyanoindole (0.64 g; 4.5 mmol), HCl×$H_2NOH$ (1.1 g; 15.8 mmol), and $Na_2CO_3$ (0.79 g; 7.43 mmol) in $H_2O$ (8 ml) and EtOH (2 ml) was gently stirred for 15 min, then refluxed for 6 h under $N_2$. After cooling most of the EtOH was removed under reduced pressure and the product was extracted with EtOAc (3×10 ml). The organic phase was separated, dried over anhydrous $MgSO_4$ and filtered. The filtrate was evaporated to dryness under reduced pressure to give the title compound (0.74 g; 94%), as a creamy foam. $^1H$-NMR (DMSO-$d_6$+$CDCl_3$+$CD_3OD$) 7.4-7.3 (m, 1H); 7.2-7.12 (m, 2H); 7.01 (t, 1H, J=7.8 Hz); 6.74 (d, 1H, J=3.1 Hz); 3.68 (HDO); 1.71 (broad s, $H_2O$).

Step B: 5-(3,4-Diethoxyphenyl)-3-(1H-indol-4-yl)-1,2,4-oxadiazole To a solution of 3,4-diethoxybenzoic acid (0.11 g; 0.52 mmol), and the product of Step A (0.09 g; 0.51 mmol) in anhydrous THF (2 ml), PyBroP (0.25 g; 0.54 mmol) was added followed by DIPEA (0.21 ml; 1.22 mmol), with stirring, at room temperature under $N_2$. After 2 h of stirring, the mixture was diluted to 15 ml with EtOAc, washed with saturated $NH_4Cl$ (2×5 ml), brine, dried over anhydrous $MgSO_4$ and filtered. The filtrate was evaporated to dryness under reduced pressure and the residue was suspended in anhydrous toluene (10 ml). To it 1M TBAF in THF (0.5 ml) was added and the reaction mixture was refluxed for 3 h under $N_2$, cooled to room temperature and solvents were removed under reduced pressure. The residue was washed with $H_2O$ (5 ml) and the solid was purified by FCC ($SiO_2$; $CH_2Cl_2$) to give the title compound (0.06 g; 34%) as colourless solid. $^1H$-NMR ($CDCl_3$) 8.42 (s, 1H); 8.06 (dd, 1H, J=2, 8.4 Hz); 7.83 (d, 1H, J=8.4 Hz); 7.74 (d, 1H, J=2 Hz); 7.54 (d, 1H, J=8.1 Hz); 7.37-7.31 (m, 3H); 6.98 (d, 1H, J=8.5 Hz); 4.26-4.16 (m, 4H); 1.5 (m, 6H).

Step C: 5-(3,4-Diethoxyphenyl)-3-(indolin-4-yl)-1,2,4-oxadiazole: To a solution of the product of Step B (0.06 g; 0.172 mmol) in 1M BH$_3$ in THF (0.35 ml; 0.35 mmol) TFA (0.4 ml) was added drop wise at 0° C. with stirring. After the addition was completed (~5 min), the reaction was quenched with H$_2$O (0.5 ml) and solvents were removed under reduced pressure. The residue was diluted to 10 ml with EtOAc and was washed with 10% NaOH (2×2 ml), brine and dried over anhydrous MgSO$_4$ and filtered. The filtrate was evaporated to dryness under reduced pressure to give the title compound (0.026 g; 43%) as a creamy foam, which was used in the next step without further purification. $^1$H-NMR (CDCl$_3$) 7.78 (dd, 1H, J=1.9, 7.2 Hz); 7.68 (d, 1H, J=1.9 Hz); 7.52 (d, 1H, J=7.2 Hz); 7.17 (t, 1H, J=7.7); 6.97 (d, 1H, J=8.5 Hz); 6.75 (d, 1H, J=7.7 Hz); 4.19 (m, 4H); 3.65 (t, 2H, J=8.9 Hz); 3.45 (tr, 2H, J=8.9 Hz); 1.7 (broad s, 1H+H$_2$O); 1.49 (m, 6H).

Step D: Ethyl 2-(4-(5-(3,4-diethoxyphenyl)-1,2,4-oxadiazol-3-yl)indoline-1-carboxamido)acetate: When the product of Step E was substituted for n-octylaniline and ethyl isocyanatoacetate was substituted for ethyl 3-isocyanatopropionate in Example 11, Step A the similar process afforded the title compound in 61%, as colourless solid. $^1$H-NMR (CDCl$_3$) 8.11 (d, 1H, J=7.4 Hz); 7.78 (dd, 2H, J=2, 7.1 Hz); 7.67 (d, 1H, J=2 Hz); 7.31 (t, 1H, J=8 Hz); 6.97 (d, 1H, J=8.5 Hz); 5.13 (t, 1H, J=5.1 Hz); 4.28-4.04 (m, 10H); 3.61 (t, 1H, J=8.6 Hz); 1.52-1.47 (m, 6H); 1.32 (t, 3H, J=7.1 Hz);

Step E: 2-(4-(5-(3,4-Diethoxyphenyl)-1,2,4-oxadiazol-3-yl)indoline-1-carboxamido)acetic acid: When the product of Step D was substituted for ethyl 3-(3-(4-octylphenyl)ureido)propanoate in Example 11, Step B the identical process afforded the title compound in 75% yield. $^1$H-NMR (DMSO-d$_6$) 8.03 (d, 1H, J=9 Hz); 7.73 (dd, 1H, J=2, 8 Hz); 7.61-7.59 (m, 2H); 7.29 (t, 1H, J=7.9 Hz); 7.17 (d, 1H, J=8.6 Hz); 7.09 (broad m, 1H); 4.17-4.0 (m, 4H); 3.98 (t, 2H, J=5.8 Hz); 3.74 (d, 2H, J=5.2 Hz); 3.47 (t, 2H, J=9 Hz); 1.38-1.32 (m, 6H).

Example 54

3-(4-(5-(3,4-Diethoxyphenyl)-1,2,4-oxadiazol-3-yl)indoline-1-carboxamido)propanoic acid Step A: Ethyl 3-(4-(5-(3,4-diethoxyphenyl)-1,2,4-oxadiazol-3-yl)indoline-1-carboxamido)propanoate: When the product of Example 16 Step C was substituted for n-octylaniline in Example 11, Step A the identical process afforded the title compound in 52% yield. $^1$H-NMR (CDCl$_3$) 8.1 (d, 1H, J=9 Hz); 7.79-7.75 (m, 2H); 7.67 (d, 1H, J=2 Hz); 7.31 (t, 1H, J=8 Hz); 6.97 (d, 1H, J=8.5 Hz); 5.38 (tr, 1H, J=5.7 Hz); 4.24-4.12 (m, 6H); 3.98 (t, 2H, J=8.6 Hz); 3.63-3.55 (m, 4H); 2.61 (t, 2H, J=5.9 Hz); 1.27 (t, 3H, J=9 Hz);

Step B: 3-(4-(5-(3,4-Diethoxyphenyl)-1,2,4-oxadiazol-3-yl)indoline-1-carboxamido)propanoic acid: When the product of Step A was substituted for ethyl 3-(3-(4-octylphenyl)ureido)propanoate in Example 11, Step B the identical process afforded the title compound in 61% yield. $^1$H-NMR (CDCl$_3$) 8.03 (d, 1H, J=9 Hz); 7.72 (dd, 1H, J=1.9, 8.4 Hz): 7.59-7.56 (m, 2H); 7.27 (t, 1H, J=7.9 Hz); 7.16 (d, 1H, J=8.6 Hz); 6.76 (t, 1H, J=5.3 Hz); 4.04-4.16 (m, 4H); 3.92 (t, 2H, J=8.6 Hz); 3.43 (tr, 2H, J=8.4 Hz); 3.36-3.28 (m, 2H+H$_2$O); 2.48-2.42 (m, 2H); 1.37-1.32 (m, 6H).

Example 55

S1P Receptors Activity Evaluation

Selected Compounds of the Examples were evaluated at Millipore Corporation, USA, using S1P1 receptor; [$^{35}$S]-GTPgamaS binding assay. A [$^{35}$S]-GTPgamaS binding assay at Millipore was conducted by GPCR Profiler™ Custom Service Laboratory, Temecula, Calif., Millipore, Inc. to monitor dose-dependent agonist selectivity for selected Examples against the S1P1 receptors. The assay was completed with sample compounds subjected to an eight-point, four-fold dose response curve with starting concentration of 10 µM. Selectivity was determined upon initial addition of compounds followed by a 30 minute incubation at 30° C. Following compound incubation, bounded [35S]-GTPgamaS was determined by filtration and scintillation counting. Percentage activation and inhibition values were determined relative to the reference agonist at S1P1 and are shown in Table 10.

Independently, selected compounds were evaluated for S1P1 and S1P3 agonistic activity. The S1P1 assay system was GTPgama-S35 binding in membranes from CHO K1 cells, expressing S1P1 human receptor. The S1P3 assay system was calcium mobilization in CHO K1 cells expressing S1P3 human receptor. There was no significant background response to S1P in the CHO K1 cells with either assay. Compounds were tested initially at a concentration of 10 µM. Those compounds with significant efficacy (Emax >0.15 relative to S1P) at either receptor type were used to generate concentration-effect (dose response) curves at that receptor. These analyses provided efficacy (Emax) and potency (EC$_{50}$) of the compounds relative to S1P, shown in Table 10.

TABLE 10

S1P1 and S1P3 agonistic activity of selected compounds of Formula (I):

| Entry Number | Example | EC$_{50}$ (µM) S1P1 | EC$_{50}$S$_1$P$_1$/ EC$_{50}$S$_1$P | Efficacy (% of maximum) | EC$_{50}$ (µM) S$_1$P$_3$ |
|---|---|---|---|---|---|
| 1 | 3 | 0.29 | 135.5 | 102.5 | ND |
| 2 | 9 | 1.63 | 761.7 | 88 | ND |
| 3 | 11 | 0.46 | 215 | 96 | ND |
| 4 | 13 | 3.21 | 1500 | 58 | ND |
| 5 | 17 | 1.76 | 542 | 97 | ND |
| 6 | 19 | 5.99 | 2799 | 130 | ND |
| 7 | 27 | 0.6 | 280.4 | 127 | ND |
| 8 | 29 | 0.2 | 93.46 | 102 | ND |
| 9 | 32 | 0.06 | 28 | 107 | ND |
| 10 | 33 | 0.14 | 65.42 | 97 | ND |
| 11 | 36 | 0.047 | 4.18 | 101 | NA |
| 12 | 37 | 1.82 | 160.8 | 40 | NA |
| 13 | 38 | 0.26 | 28.17 | 74 | NA |
| 14 | 39 | 3.46 | 305 | 16 | NA |
| 15 | 40 | 0.057 | 4.75 | 106 | 0.38 |

NA = no activity;
ND = not determined.

Example 56

Lymphopenia Assay

The study was performed at vivoPharm Pty Ltd, Adelaide, Australia, to determine the ability of the compounds of invention to induce lymphopenia in female BALB/c mice. On day 0, 27 female BALB/c mice were randomised based on body weight into nine groups of three mice each. Animals received a single i.p. administration of Test compounds and blood was collected by cardiac puncture either 6 or 24 h after administration. Treatment with 3 mg/kg of Example 40 was shown to decrease lymphocyte counts at both 6 and 24 h, compared to untreated animals (FIG. 1). Changes to other haematological parameters were not observed.

The invention claimed is:
1. A compound of formula (II) or a salt thereof:

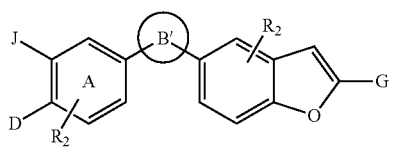

(II)

wherein
B' is a five-membered heterocyclic ring selected from one of the following:

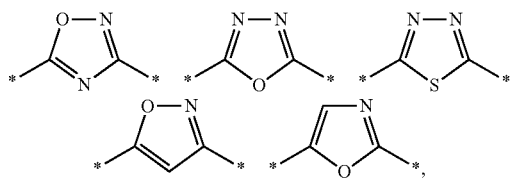

the asterisks indicating the attachment within formula (II);
G represents

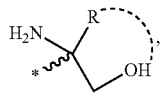

R is selected from hydrogen, deuterium, alkylamino, CH$_2$OH, alkoxy, a C$_{1-5}$ alkyl chain optionally containing one or more of deuterium, O, NR'R", S, and halogen, heterocycle, amide, sulphonamide, COOH, —OPO$_3$H$_2$, and —PO$_3$H$_2$, represents an optional bridging group;
A ring is phenyl or pyridinyl;
R$_2$ independently is selected from halogen, hydrogen, deuterium, CN, amino, alkylamino, alkoxy, CF$_3$, and a C$_{1-4}$ alkyl chain optionally containing one or more of deuterium, OH, NR'R", S, SO, SO$_2$, a carbon-carbon double bond, a carbon-carbon triple bond, a carbon-heteroatom double bond, a carbon-hetero atom triple bond, carbocycle, heterocycle, amide, and sulphonamide; and
the groups J and D each are independently selected from hydrogen, deuterium, C$_{1-6}$ alkyl, C$_{1-6}$ alkoxy, C$_{1-6}$ alkylamino, halogen, amino, hydroxy, cyano, aryl, heterocycle, carbocycle, and a C$_{1-10}$ alkyl chain optionally containing a carbon-carbon multiple bond or a carbon-hetero multiple bond wherein one or more carbon atoms are optionally independently replaced with oxygen, sulphur, SO, SO$_2$, NR', carbocycle or heterocycle; and
R' and R" each are independently selected from alkyl, cycloalkyl, aryl, and heterocycle.
2. The compound of claim 1,
wherein
D is selected from C$_{1-6}$ alkyl, C$_{1-6}$ alkoxy, C$_{1-6}$ alkylamino, aryl, heterocycle and carbocycle or a C$_{1-7}$ alkyl chain optionally containing a carbon-carbon multiple bond or a carbon-hetero multiple bond wherein one or more carbon atoms are optionally independently replaced with oxygen, sulphur, SO, SO$_2$, NR', carbocycle and heterocycle;
J is selected from H, deuterium, C$_{1-4}$ alkyl, C$_{1-4}$ alkoxy, C$_{1-4}$ alkylamino, halogen, amino, hydroxy, cyano or a C$_{1-5}$ alkyl chain optionally containing a carbon-carbon multiple bond or a carbon-hetero multiple bond wherein one or more carbon atoms are optionally independently replaced with oxygen, sulphur, SO, SO$_2$, NR', carbocycle and heterocycle; and
R' is selected from alkyl, cycloalkyl, aryl, and heterocycle.
3. A compound selected from the group consisting of:
1-((5-(5-(3,4-diethoxyphenyl)-1,2,4-oxadiazol-3-yl)benzofuran-2-yl)methyl)azetidine-3-carboxylic acid,
2-amino-2-(5-(5-(3-chloro-4-propoxyphenyl)-1,2,4-oxadiazol-3-yl)benzofuran-2-yl)propane-1,3-diol,
2-amino-2-(5-(5-(4-bromo-3-chlorophenyl)-1,2,4-oxadiazol-3-yl)benzofuran-2-yl)propane-1,3-diol,
2-amino-2-(5-(5-(3-chloro-4-(thiophen-3-yl)phenyl)-1,2,4-oxadiazol-3-yl)benzofuran-2-yl)propane-1,3-diol,
2-amino-2-(5-(5-(3,4-diethoxyphenyl)-1,2,4-oxadiazol-3-yl)benzofuran-2-yl)propane-1,3-diol,
2-amino-2-(5-(5-(4-propoxy-3-methoxyphenyl)-1,2,4-oxadiazol-3-yl)benzofuran-2-yl)propane-1,3-diol,
2-amino-2-(5-(5-(6-methoxybenzofuran-2-yl)-1,2,4-oxadiazol-3-yl)benzofuran-2-yl)propane-1,3-diol,
2-amino-2-(5-(5-(4-propylphenyl)-1,2,4-oxadiazol-3-yl)benzofuran-2-yl)propane-1,3-diol,
2-amino-2-(5-(5-(4-ethoxyphenyl)-1,2,4-oxadiazol-3-yl)benzofuran-2-yl)propane-1,3-diol,
2-amino-2-(6-chloro-5-(5-(4-propylphenyl)-1,2,4-oxadiazol-3-yl)benzofuran-2-yl)propane-1,3-diol,
2-amino-2-(5-(5-(1-butyl-1H-pyrazol-4-yl)-1,2,4-oxadiazol-3-yl)benzofuran-2-yl)propane-1,3-diol,
2-amino-2-(5-(5-(3-nitro-4-propoxyphenyl)-1,2,4-oxadiazol-3-yl)benzofuran-2-yl)propane-1,3-diol,
5-(3-(2-(2-amino-1,3-dihydroxypropan-2-yl)benzofuran-5-yl)-1,2,4-oxadiazol-5-yl)-2-propoxybenzonitrile,
2-amino-2-(5-(5-(3-bromo-4-propoxyphenyl)-1,2,4-oxadiazol-3-yl)benzofuran-2-yl)propane-1,3-diol,
2-amino-2-(5-(2-(2-(4-fluorophenyl)-4-methyloxazol-5-yl)ethyl)benzofuran-2-yl)propane-1,3-diol,
2-amino-2-(5-(2-(2-(4-fluorophenyl)-4-methylthiazol-5-yl)ethyl)benzofuran-2-yl)propane-1,3-diol,
2-amino-2-(5-(2-(methyl(pyridin-2-yl)amino)ethoxy)benzofuran-2-yl)propane-1,3-diol,
2-amino-2-(5-(2-(2-(4-fluorophenyl)-5-methyloxazol-4-yl)ethyl)benzofuran-2-yl)propane-1,3-diol,
2-amino-2-(5-(3-(methyl(pyridin-2-yl)amino)propyl)benzofuran-2-yl)propane-1,3-diol,
2-amino-2-(5-(5-(2-cyclopropylbenzofuran-5-yl)-1,2,4-oxadiazol-3-yl)benzofuran-2-yl)propane-1,3-diol,
2-amino-2-(5-(5-(4-isobutoxyphenyl)-1,2,4-oxadiazol-3-yL)benzofuran-2-yl)-1,3-diol,
2-amino-2-(6-chloro-5-(5-(3,4-diethoxyphenyl)-1,2,4-oxadiazol-3-yl)benzofuran-2-yl)propane-1,3-diol,
2-amino-2-(5-(5-(3-chloro-4-methoxyphenyl)-1,2,4-oxadiazol-3-yl)benzofuran-2-yl)propane-1,3-diol,
2-amino-2-(5-(5-(3,4-dimethoxyphenyl)-1,2,4-oxadiazol-3-yl)benzofuran-2-yl)propane-1,3-diol,
2-amino-2-(5-(5-(3-chloro-4-ethoxyphenyl)-1,2,4-oxadiazol-3-yl)benzofuran-2-yl)propane-1,3-diol,
5-(3-(2-(2-amino-1,3-dihydroxypropan-2-yl)benzofuran-5-yl)-1,2,4-oxadiazol-5-yl)-2-ethoxybenzonitrile, 2-amino-2-(5-(5-(3-chloro-4-ethoxyphenyl)-1,2,4-oxadiazol-3-yl)-7-methyl-benzofuran-2-yl)propane-1,3-diol, 2-amino-2-(5-(5-(3,4-diethoxyphenyl)-1,2,4-oxadiazol-3-yl)-7-methylbenzofuran-2-yl)propane-1,3-diol, 5-(3-(2-(2-amino-1,3-dihydroxypropan-2-yl)-7-methyl-benzofuran-5-yl)-1,2,4-oxadiazol-5-yl)-2-propoxybenzonitrile, N-(5-(3-(2-(2-amino-1,3-dihydroxypropan-2-yl)benzofuran-5-yl)-1,2,4-oxadiazol-5-yl)-2-ethoxyphenyl)methanesulfonamide, 2-amino-2-(5-(5-(3,4-diethoxyphenyl)-1,2,4-oxadiazol-3-yl)furo[2,3-b]pyridin-2-yl)propane-1,3-diol, 2-amino-2-(5-(5-(4-ethoxy-3-methoxyphenyl)-1,2,4-oxadiazol-3-yl)benzofuran-2-yl)propane-1,3-diol, 2-amino-2-((5-(5-(3,4-diethoxyphenyl)-1,2,4-oxadiazol-3-yl)benzofuran-2-yl)methylamino)propane-1,3-diol, 2-amino-2-(5-(5-(4-propoxy-3-(trifluormethyl)phenyl)-1,2,4-oxadiazol-3-yl)benzofuran-2-yl)propane-1,3-diol.

4. A pharmaceutical composition, comprising at least one compound as claimed in claim 1 in any of its stereoisomeric and/or isotopic forms and/or physiologically tolerable and/or therapeutically effective salts or mixtures thereof in any ratio together with a pharmaceutically acceptable carrier(s) or excipient(s).

\* \* \* \* \*